(12) United States Patent
Levine

(10) Patent No.: US 6,964,480 B2
(45) Date of Patent: *Nov. 15, 2005

(54) OPHTHALMIC INSTRUMENT HAVING ADAPTIVE OPTIC SUBSYSTEM WITH MULTIPLE STAGE PHASE COMPENSATOR

(75) Inventor: Bruce M. Levine, Arcadia, CA (US)

(73) Assignee: Metrologic Instruments, Inc., Blackwood, NJ (US)

( * ) Notice: Subject to any disclaimer, the term of this patent is extended or adjusted under 35 U.S.C. 154(b) by 113 days.

This patent is subject to a terminal disclaimer.

(21) Appl. No.: 09/944,053

(22) Filed: Aug. 31, 2001

(65) Prior Publication Data

US 2003/0053030 A1 Mar. 20, 2003

(51) Int. Cl.[7] ............................... A61B 3/10
(52) U.S. Cl. ............... 351/211; 351/205; 351/221
(58) Field of Search ........................ 351/205, 206, 351/209, 210, 211, 212, 213–216, 220, 221, 246, 247, 200, 222, 232, 233, 237, 239; 600/558

(56) References Cited

U.S. PATENT DOCUMENTS

| | | | |
|---|---|---|---|
| 4,399,356 A | 8/1983 | Feinleib et al. | |
| 4,500,180 A | 2/1985 | Stevens | |
| 4,579,430 A | 4/1986 | Bille | |
| 4,725,138 A | 2/1988 | Wirth et al. | |
| H615 H | 4/1989 | Feinleib et al. | |
| 4,848,340 A | 7/1989 | Bille et al. | |
| 4,881,808 A | 11/1989 | Bille et al. | |

(Continued)

FOREIGN PATENT DOCUMENTS

| WO | WO 97/21989 | 6/1997 | ............ G01J/9/00 |
|---|---|---|---|
| WO | WO 01/58339 A2 | 2/2001 | |
| WO | WO 01/28408 A2 | 4/2001 | |
| WO | WO 01/28410 A1 | 4/2001 | |
| WO | WO 01/71411 A2 | 9/2001 | |
| WO | WO 01/78585 A2 | 10/2001 | |
| WO | WO 01/82228 A2 | 11/2001 | |
| WO | WO 01/85016 A2 | 11/2001 | |
| WO | WO 01/87201 A1 | 11/2001 | |

OTHER PUBLICATIONS

Spectral Configuration Guide for DuncanTech 3–CCD Cameras by, http://www.duncantech.com/spepctral_ configuration_ guide.htm, Aug. 30, 2001.

Plate Beamsplitters by , www.edmundoptics.com/IOD/DisplayProduct.cfm?productid–2035#Technical%20Images, Aug. 30, 2001.

Tech Spec Polarizing Cube BeamSplitters by http://www.edmundoptics.com/IOD/DisplayProduct.cfm?productid=1925#Technical%20Im, Aug. 30, 2001.

(Continued)

Primary Examiner—Francis Jaworski
Assistant Examiner—John R. Sanders
(74) Attorney, Agent, or Firm—Thomas J. Perkowski, Esq., P.C.

(57) ABSTRACT

An improved ophthalmic instrument for estimating aberrations in the eyes of a patient and providing the patient with a view of optical correction of the aberrations so as to provide instant feedback as to the accuracy of the estimated aberrations. The ophthalmic instrument comprises an adaptive optic subsystem for sensing and correcting estimated aberrations in a patient's eye, and a fixation target providing a view of correction of the estimated aberrations. The adaptive optics subsystem includes a wavefront sensor and a multi-stage phase compensator. The multi-stage phase compensator includes a first stage for compensating for a defocus component of the estimated aberrations, and at least one other additional stage for compensating other higher order components of estimated aberrations. Preferably, the first stage comprises a variable focus lens for defocus correction, and the additional stage(s) comprises a deformable mirror for correction of higher order aberrations estimated in the eye.

12 Claims, 36 Drawing Sheets

U.S. PATENT DOCUMENTS

| | | | |
|---|---|---|---|
| 4,943,709 A * | 7/1990 | Grinberg et al. ............ | 356/121 |
| 5,062,702 A | 11/1991 | Bille | |
| 5,258,791 A | 11/1993 | Penney et al. | |
| 5,360,424 A | 11/1994 | Klopotek | |
| 5,473,392 A | 12/1995 | Klopotek | |
| 5,521,657 A | 5/1996 | Klopotek | |
| 5,629,765 A | 5/1997 | Schumtz | |
| 5,777,719 A * | 7/1998 | Williams et al. ............ | 351/212 |
| 5,822,035 A | 10/1998 | Bille | |
| 5,865,832 A | 2/1999 | Knopp et al. | |
| 5,920,373 A | 7/1999 | Bille | |
| 5,949,521 A | 9/1999 | Williams et al. | |
| 6,000,800 A | 12/1999 | Webb et al. | |
| 6,007,202 A | 12/1999 | Apple et al. | |
| 6,007,204 A | 12/1999 | Fahrenkrug et al. | |
| 6,050,687 A | 4/2000 | Bille et al. | |
| 6,084,227 A | 7/2000 | Rhoads | |
| 6,086,204 A | 7/2000 | Magnante | |
| 6,095,651 A | 8/2000 | Williams et al. | |
| 6,142,630 A | 11/2000 | Koester | |
| 6,153,760 A | 11/2000 | Kunzler | |
| 6,155,684 A | 12/2000 | Bille et al. | |
| 6,193,369 B1 | 2/2001 | Valint et al. | |
| 6,193,710 B1 | 2/2001 | Lemberg | |
| 6,199,986 B1 | 3/2001 | Williams et al. | |
| 6,270,221 B1 | 8/2001 | Liang et al. | |
| 6,305,802 B1 | 10/2001 | Roffman et al. | |
| 6,394,605 B1 * | 5/2002 | Campin et al. ............ | 351/246 |
| 6,406,146 B1 * | 6/2002 | Lai ............................ | 351/206 |
| 6,460,997 B1 * | 10/2002 | Frey et al. ................ | 351/211 |
| 2001/0016695 A1 | 8/2001 | Bradley | |
| 2002/0159029 A1 * | 10/2002 | Ross et al. ................ | 351/212 |
| 2003/0003295 A1 * | 1/2003 | Dreher et al. ............. | 351/159 |
| 2003/0038921 A1 * | 2/2003 | Neal et al. ................ | 351/212 |

OTHER PUBLICATIONS

TechSpec Dichroic Cube Beamsplitters by Edmund Optics, http://www.edmundoptics.com/IOD/DisplayProduct.cfm?productid=2037, Aug. 30, 2001.

Dichroic Prism Assembly by www.techexpo.com/WWW/richter/prisms.html, Jul. 10, 2001.

Visions by Welch Allyn, Inc., Skaneateles Falls NY, circa Aug. 2001.

WelchAllyn SureSight Autorefractor by WelchAllyn, Skaneateles Falls NY, 2001, p. i–26, circa Aug. 2001.

Clinical Applications of the Shack–Hartmann Aberrometer by Larry N. Thibos, School of Optometry, Indiana Univ., Bloomington IN, 2001, p. 1–15, Jun. 5, 2001.

Slit Lamps by www.nidek.com/sl.html, Jun. 4, 2001.

Autorefractometer and AutoRef/Keratometer by www.nidek.com/arark.html, Jun. 4, 2001.

Fundus Camera by http://www.nidek.com/fundus.html, Jun. 4, 2001.

Corneal Topography and Imaging by Peter Fedor, et. al., eMedicine Journal, Dec. 10, 2001, p. 1–9.

About Axial PointSource Optics by http://panoptic.welchallyn.com/showme.html, May 16, 2001.

CF–60UD 60 Degree Fundus Camera by Opto Electronica, 2001, p. 1–4, May 10, 2001.

37–channel adaptive system based on micromachined AM: dummy technical passport by, OKO Technologies, 2001, p. 1–8, Jun. 25, 2002.

Nidek—OPD Sean by Nidek, www.nidek.com, Jun. 4, 2001.

Germany's 20/10 perfect Vision Reports Wavefront Custom Ablation Results of Wave by VisionMonday.com, VisionMonday.com, 2001, May 8, 2001.

Supervision by Joyce Gramza, Popular Science, Mar. 2001.

Application Note by E. Herijgers, et. al., Philips Semiconductors, p. 1–2. Feb. 18, 2000.

Wavescope Products from Adaptive Optics, Sections 1, 4, 5, 8 by Karen Signorelli, Adaptive Optics, Jun. 4, 2001.

Are You Ready for the Next Wave? by Brian R. Will, et. al., Opthalmology Management, Oct. 2000.

A Quick Method for Analyzing Hartmann–Shack Patterns: Application to Refractive by Hamam, et. al., Journal of Refractive Surgery, vol. 16, Sep./Oct. 2000, p. S636–S642.

Eye on Industry: Demand Surges for New Wavefront Diagnostic Devices by Marilyn Haddrill, EW Opthalmology News, Sep. 2000, p. 1–5.

The History and Methods of Ophthalmic Wavefront Sensing by Howard C. Howland, et. al., Journal of Refractive Surgery, vol. 16, Sep./Oct. 2000, p. S552–S553.

Understanding Aberrations by Using Double–Pass Techniques by Pablo Artal, et. al., Journal of Refractive Surgery, vol. 16, Sep./Oct. 2000, p. S560–S562.

Principles of Tscherning Aberrometry by Michael Mrochen, et. al., Journal of Refractive Surgery, vol. 16, Sep./Oct. 2000, p. S570–S57.

The Spatially Resolved Optometer for Human Eyes by Larry N. Thibos, Small Business Technology Transfer Program, Phase 1 Grant Application, Nov. 1998.

* cited by examiner

Ideal Eye

Aberrated Eye

OPHTHALMIC INSTRUMENT HAVING ADAPTIVE OPTIC SUBSYSTEM WITH MULTIPLE STAGE PHASE COMPENSATOR

CROSS-REFERENCE TO RELATED APPLICATIONS

The present Application is related to the following United States Patent Applications: copending application Ser. No. 09/944,056, filed concurrently herewith, entitled "Ophthalmic Instrument With Adaptive Optic Subsystem That Measures Aberrations (Including Higher Order Aberrations) Of A Human Eye And That Provides A View Of Compensation Of Such Aberrations To The Human Eye," by Bruce M. Levine, Allan Wirth, and C. Harry Knowles; copending application Ser. No. 09,944,047, filed concurrently herewith, entitled "Ophthalmic Instrument Having Wavefront Sensor With Multiple Imaging Devices that Simultaneously Capture Multiple Images Of An Array Of Spots Produced By A Lenslet Array," by Allan Wirth, U.S. Pat. No. 6,669,341; copending application Ser. No. 09/944,054 entitled "Ophthalmic Instrument Having Hartmann Wavefront Sensor With Extended Source" by Allan Wirths, U.S. Pat. No. 6,595,642; copending application Ser. No. 09/943,759 entitled "Ophthalmic Instrument Having Hartmann Wavefront Sensor Deriving Location Of Spots With Spot Fitting Techniques" by Allan Wirth, U.S. Pat. No. 6,631,991; copending application Ser. No. 09/874,403, filed Jun. 5, 2001, entitled "Ophthalmic Imaging Instrument Having An Adaptive Optical Subsystem That Measures Phase Aberrations in Reflections Derived From Light Produced By An Imaging Light Source And That Compensates For Such Phase Aberrations When Capturing Images of Reflections Derived From Light Produced By The Same Imaging Light Source," by Bruce M. Levines, U.S. Pat. No. 6,595,643; copending application Ser. No. 09/874,401, filed Jun. 5, 2001, entitled "Modular Adaptive Optical Subsystem for Integration With A Fundus Camera Body and CCD Camera Unit and Improved Fundus Camera Employing Same," by Bruce M. Levines, U.S. Pat. No. 6,582,078; copending application Ser. No. 09/874,404, filed Jun. 5, 2001, entitled "Ophthalmic Instrument Having An Integral Wavefront Sensor and Display Device That Displays A Graphical Representation of High Order Aberrations of the Human Eye Measured by the Wavefront Sensor," by Bruce M. Levines, U.S. Pat. No. 6,576,230; and copending application Ser. No. 09/874,903, filed Jun. 5, 2001, entitled "Ophthalmic Instrument Having An Integral Wavefront Sensor and Display Device That Displays A Graphical Representation of High Order Aberrations of the Human Eye Measured by the Wavefront Sensor," by Bruce M. Levine, U.S. Pat. No. 6,609,794; each being assigned to Adaptive Optics Associates, Inc., and incorporated herein by reference in its entirety.

BACKGROUND OF THE INVENTION

1. Field of the Invention

The present invention relates to ophthalmic instruments that are used to examine or treat the eye, including ophthalmic examination instruments (such as phoropters and autorefractors) that measure and characterize the aberrations of the human eye in order to prescribe compensation for such aberrations via lens (such as glasses or contact lens) or surgical procedure (such as laser refractive surgery), in addition to ophthalmic imaging instruments (such as fundus cameras, corneal topographers, retinal topographers, corneal imaging devices, and retinal imaging devices) that capture images of the eye.

2. Summary of the Related Art

The optical system of the human eye has provided man with the basic design specification for the camera. Light comes in through the cornea, pupil and lens at the front of the eye (as the lens of the camera lets light in). This light is then focused on the inside wall of the eye called the retina (as on the film in a camera). This image is detected by detectors that are distributed over the surface of the retina and sent to the brain by the optic nerve which connects the eye to the brain (as film captures the image focused thereon).

FIG. 1 shows a horizontal cross section of the human eye. The eye is nearly a sphere with an average diameter of approximately 20 mm. Three membranes—the cornea and sclera outer cover, the choroid and the retina—enclose the eye. The cornea 3 is a though transparent tissue that covers the anterior surface of the eye. Continuous with the cornea 3, the sclera 5 is an opaque membrane that encloses the remainder of the eye. The choroid 7 lies directly below the sclera 5 and contains a network of blood vessels that serves as the major source of nutrition to the eye. At its anterior extreme, the choroid 7 includes a ciliary body 9 and an iris diaphragm 11. The pupil of the iris diaphragm 11 contracts and expands to control the amount of light that enters the eye. Crystalline lens 13 is made up of concentric layers of fibrous cells and is suspended by fibers 15 that attach to the ciliary body 9. The crystalline lens 13 changes shape to allow the eye to focus. More specifically, when the ciliary muscle in the ciliary body 9 relaxes, the ciliary processes pull on the suspensory fibers 15, which in turn pull on the lens capsule around its equator. This causes the entire lens 13 to flatten or to become less convex, enabling the lens 13 to focus light from objects at a far away distance. Likewise, when the ciliary muscle works or contracts, tension is released on the suspensory fibers 15, and subsequently on the lens capsule, causing both lens surfaces to become more convex again and the eye to be able to refocus at a near distance. This adjustment in lens shape, to focus at various distances, is referred to as "accommodation" or the "accommodative process" and is associated with a concurrent constriction of the pupil.

The innermost membrane of the eye is the retina 17, which lies on the inside of the entire posterior portion of the eye. When the eye is properly focused, light from an object outside the eye that is incident on the cornea 3 is imaged onto the retina 17. Vision is afforded by the distribution of receptors (e.g., rods and cones) over the surface of the retina 17. The receptors (e.g., cones) located in the central portion of the retina 17, called the fovea 19 (or macula), are highly sensitive to color and enable the human brain to resolve fine details in this area. Other receptors (e.g., rods) are distributed over a much larger area and provides the human brain with a general, overall picture of the field of view. The optic disc 21 (or the optic nerve head or papilla) is the entrance of blood vessels and optic nerves from the brain to the retina 17. The inner part of the posterior portion of the eye, including the optic disc 21, fovea 19 and retina 17 and the distributing blood vessels in called the ocular fundus 23. Abnormalities in the cornea and crystalline lens and other portions of the eye contribute to refractive errors (such as defocus, astigmatism, spherical aberrations, and other high order aberrations) in the image captured by the retina.

A phoropter (or retinoscope) is an ophthalmic instrument that subjectively measures the refractive error of the eye. A typical phoropter consists of a pair of housings in which are positioned corrective optics for emulating the ophthalmic prescription required to correct the vision of the patient whose eyes are being examined. Typically, each housing contains sets of spherical and cylindrical lenses mounted in rotatable disks. The two housings are suspended from a stand or wall bracket for positioning in front of the patient's eyes. Further, in front of each refractor housing a number of accessories are mounted, typically on arms, so that they may be swung into place before the patient's eyes. Typically, these accessories include a variable power prism known as a Risley prism, Maddox rods, and a cross cylinder for performing the Jackson cross cylinder test. In determining a patient's distance prescription, the patient views a variety of alpha numeric characters of different sizes through various combinations of the spherical and/or cylindrical lenses supported in the refractor housings until the correct prescription is emulated. The characters, which are typically positioned 6 meters away, may be on a chart or may be projected on a screen by an acuity projector. For near vision testing the same procedure is repeated, expect that the alpha numeric characters viewed by the patient are positioned on a bracket 20 to 65 centimeters in front of the refractor housing. The cross cylinder is used to refine the power and axis position of the cylindrical component of the patient's prescription. The cross cylinder is a lens consisting of equal power plus and minus cylinders with their axes 90 degrees apart. It is mounted in a loupe for rotation about a flip axis which is midway between the plus and minus axes.

An autorefractor is an ophthalmic instrument that quantitatively measures the refractor errors of the eye. Light from an illumination source (typically an infra-red illumination source) is directed into the eye of the patient being examined. Reflections are collected and analyzed to quantitatively measure the refractive errors of the eye.

Conventional phoropters and autorefractors characterize the refractive errors of the eye only in terms of focal power (typically measured in diopter) required to compensate for such focal errors; thus, such instruments are incapable of measuring and characterizing the higher order aberrations of the eye, including astigmatism and spherical aberration. Examples of such devices are described in the following U.S. Pat. Nos. 4,500,180; 5,329,322; 5,455,645; 5,629,747; and 5,7664,561.

Instruments have been proposed that utilize wavefront sensors to measure and characterize the high order aberrations of the eye. For example, U.S. Pat. No. 6,007,204, to Fahrenkrug et al. discloses an apparatus for determining refractive aberrations of the eye wherein a substantially collimated beam of light is directed to the eye of interest. This collimated light is focused as a secondary source on the back of the eye, thereby producing a generated wavefront that exits the eye along a return light path. A pair of conjugate lenses direct the wavefront to a microoptics array of lenslet elements, where incremental portions of the wavefront are focuses onto an imaging substrate. Deviation of positions of the incremental portions relative to a known zero or "true" position (computed by calculating the distance between the centroids of spots formed on the imaging substrate by the lenslet array) can be used to compute refractive error relative to a known zero or ideal diopter value. Because the optical power at the lenslet does not equal the optical power of the measured eye, the optical power of the lenslet is corrected by the conjugate lens mapping function to interpolate the power of the eye. This refractive error is reported to the user of the apparatus through an attached LCD.

In U.S. Pat. Nos. 5,777,719; 5,949,521; and 6,095,651, Williams and Liang disclose a retinal imaging method and apparatus that produces a point source on a retina by a laser. The laser light reflected from the retina forms a distorted wavefront at the pupil, which is recreated in the plane of a deformable mirror and a Shack-Hartmann wavefront sensor. The Shack-Hartmann wavefront sensor includes an array of lenslets that produce a corresponding spot pattern on a CCD camera body in response to the distorted wavefronts. Phase aberrations in the distorted wavefront are determined by measuring spot motion on the CCD camera body. A computer, operably coupled to the Shack-Hartmann wavefront sensor, generates a correction signal which is fed to the deformable mirror to compensate for the measured phase aberrations. After correction has been achieved via the wavefront sensing of the reflected retinal laser-based point source, a high-resolution image of the retina can be acquired by imaging a krypton flash lamp onto the eye's pupil and directing the reflected image of the retina to the deformable mirror, which directs the reflected image onto a second CCD camera body for capture. Examples of prior art Shack-Hartmann wavefront sensors are described in U.S. Pat. Nos. 4,399,356; 4,725,138, 4,737,621, and 5,529,765; each herein incorporated by reference in its entirety.

Notably, the apparatus of Fahrenkrug et al. does not provide for compensation of the aberrations of the eye. Moreover, the apparatus of Fahrenkrug et al. and the apparatus of Williams and Liang do not provide a view of the compensation of the aberrations to the eye. Thus, the patient cannot provide immediate feedback as to the accuracy of the measurement; and must wait until compensating optics (such as a contact lens or glasses that compensate for the measured aberrations) are provided in order to provide feedback as to the accuracy of the measurement. This may lead to repeat visits, thereby adding significant costs and inefficiencies to the diagnosis and treatment of the patient.

In addition, the wavefront sensing apparatus (i.e., the lenslet array and imaging sensor) of Fahrenkrug et al. and of Williams and Liang are susceptible to a dot crossover problem. More specifically, in a highly aberrated eye, the location of spots produced on the imaging sensor may overlap (or cross). Such overlap (or crossover) introduces an ambiguity in the measurement that must be resolved, or an error will be introduced.

In addition, the signal-to-noise ratio provided by traditional Hartmann sensing techniques in measuring the aberrations of the human eye is limited, which restricts the potential usefulness of ophthalmic instruments that embody such techniques in many real-world ophthalmic applications. More specifically, the basic measurement performed by any Hartmann wavefront sensor is the determination of the locations of the Hartmann spots. Traditionally, this has been done by calculating the centroid of the illumination in a pixel subaperture defined around each spot.

Centroid calculation is conceptually very simple. To calculate the centroid of the light distribution in the x-direction, weights are assigned to each column of pixels in the pixel subaperture and the measured intensity for each pixel in the pixel subaperture is multiplied by the weight corresponding to the column of the given pixel and summed together. If the weights vary linearly with the distance of the column from the center of the pixel subaperture, this sum will be a measure of the x-position of the light distribution. The sum needs to be normalized by dividing by the sum of the unweighted intensities. To calculate the centroid of the light distribution in the y-direction, weights are assigned to each row of pixels in the pixel subaperture and the measured intensity for each pixel in the pixel subaperture is multiplied by the weight corresponding to the row of the given pixel and summed together. If the weights vary linearly with the distance of the column from the center of the pixel subaperture, this sum will be a measure of the y-position of the light distribution. The sum needs to be normalized by dividing by the sum of the unweighted intensities. Such centroid calculation may be represented mathematically as follows:

$$x_c = \frac{\sum_i \sum_j w_j * I_{ij}}{\sum_i \sum_j I_{ij}}$$

$$y_c = \frac{\sum_i \sum_j w_i * I_{ij}}{\sum_i \sum_j I_{ij}}$$

where i and j identify the rows and columns, respectively, of the pixel subaperture; $w_i$ and $w_j$ are the weights assigned to given rows and columns, respectively, of the pixel subaperture; and $I_{ij}$ is the intensity of a given pixel in row i and column j of the pixel subaperture.

This "center-of-light" measurement is analogous to the usual center-of-mass calculation. FIG. 2 shows a one dimensional representation of the intensity distribution on a row of detector pixels and a set of weights. These weights are simply the distance of the center of the pixel from the center of the pixel subaperture in units of pixel spacing.

However, centroid calculation is disadvantageous because it is susceptible to background noise and thus may be unacceptable in many real-world environments where background noise is present. FIG. 2 reveals these shortcomings. Note that the highest weights are applied to pixels farthest from the center. Note also that, typically, there is very little light in these regions. This means that the only contribution to these highly weighted pixels comes from background light and noise. Because of the high weight, these pixels adversely affect the accuracy of the measurement. As the size of the pixel region of that measures such spot motion is increased to provide greater tilt dynamic range, the noise problem is made worse by increasing the number of pixels that usually have no useful signal.

An even larger problem stems from the centroid algorithms sensitivity to residual background signal. Consider a pixel region that is 10×10 pixels in size. Typically, a given spot will occupy less than 10 of those pixels. Suppose there is a residual background signal that produces, per pixel, 1% of the signal from the given spot. Because it is present in all 100 pixels, its contribution to the total signal is equal to that of the spot. Even if this background is perfectly uniform, when the centroid is normalized by the total signal, that divisor will be twice its true size. This will make the calculated centroid half is correct value. If the background is not uniform, its effect on the centroid can easily overwhelm that of the spot. Thus, the susceptibility of the centroid algorithm to background noise makes it unacceptable in many real-world environments where such background noise is present.

Thus, there is a great need in the art for improved ophthalmic instruments that measure and characterize the aberrations of the human eye in a manner that avoids the shortcomings and drawbacks of prior art ophthalmic instruments.

SUMMARY OF THE INVENTION

Accordingly, a primary object of the present invention is to provide improved ophthalmic instruments that measure and characterize the aberrations of the human eye in a manner free of the shortcomings and drawbacks of prior art ophthalmic instruments.

Another object of the present invention is to provide an ophthalmic instrument that measures the aberrations (including higher order aberrations) of the eye(s) of a patient and provides the patient with a view of correction (e.g., compensation) of the measured aberrations such that the patient can provide instant feedback as to the accuracy of the measurement.

Another object of the present invention is to provide an ophthalmic instrument that includes an adaptive optic subsystem that measures the aberrations (including higher order aberrations) of the eye(s) of a patient, and an internal fixation target, operably coupled to the adaptive optic subsystem, to provide the patient with a view of correction (e.g., compensation) of the measured aberrations such the patient can provide instant feedback as to the accuracy of the measurement.

Another object of the present invention is to provide an ophthalmic instrument that includes a wavefront sensor that measures the aberrations (including higher order aberrations) of the eye(s) of a patient, an internal fixation target and phase compensator that provides the patient with a view of correction (e.g., compensation) of the measured aberrations, and high resolution image capture capabilities.

Another object of the present invention is to provide an ophthalmic instrument that provides more efficient and effective prescription of corrective optics (e.g., classes or contact lens) by measuring the aberrations (including higher order aberrations) of the eye(s) of a patient, identifying a set of prescriptions that correspond to the measured aberrations of the eye(s), and providing the patient with a view of correction (e.g., compensation) provided by the prescriptions in the set to thereby enable instant patient feedback and patient selection of the best prescription (if necessary).

Another object of the present invention is to provide an ophthalmic instrument that provides more efficient and effective dispensing of corrective optics (e.g., classes or contact lens) by: measuring the aberrations (including higher order aberrations) of the eye(s) of a patient, identifying a set of corrective optics that correspond to the measured aberrations of the eye(s), and providing the patient with a view of correction (e.g., compensation) provided by the corrective optics in the set to thereby enable the patient to select the best corrective optic (if necessary) with minimal assistance.

Another object of the present invention is to provide a system that provides for efficient dispensing of glasses whose frame is optimally fitted to the dimension of the head and face of the patient and whose corrective lens elements optimally compensate for the aberrations of eyes. The system measures the aberrations (including higher order aberrations) of the eyes of a patient, identifies a set of lens elements that correspond to the measured aberrations of the eyes, and provides the patient with a view of correction (e.g., compensation) provided by the lens elements in the set to enable the patient to select the optimal corrective lens element (if necessary). In addition, the system performs imaging and dimensioning analysis on the head and face of the patient to generate a profile of the dimensions of the head and face of the patient, and identifies a set of frames that correspond to the patient's profile to enable the patient to select one of the frames in the set. The patient selected corrective lens elements and frame (which may be custom built) are integrated into glasses and provided to the patient.

Another object of the present invention is to provide an ophthalmic instrument that includes a wavefront sensor that estimates the aberrations (including higher order aberrations) of the eye(s) and a multi-stage phase compensator (such as the variable focus lens (VFL) and a deformable mirror) having multiple stages that compensate for different parts of the aberrations of the eye as estimated by the wavefront sensor.

Another object of the present invention is to provide an ophthalmic instrument that includes a wavefront sensor that estimates the aberrations (including higher order aberrations) of the eye(s) and a multi-stage phase compensator comprising a variable focus lens (VFL) and a deformable mirror, wherein the variable focus lens compensates for the defocus component of such aberrations, and the deformable mirror compensates for other higher order components of such aberrations.

Another object of the present invention is to provide an ophthalmic instrument that includes a Hartmann style wavefront sensor that estimates the aberrations (including higher order aberrations) of the eye(s) in real time in order to minimize the adverse effects of eye movement and/or accommodation on the accuracy of such estimates, thereby capable of avoiding immobilization of the eye and/or paralysis of the eye via drugs.

Another object of the present invention is to provide an ophthalmic instrument that includes a Hartmann style wavefront sensor that estimates the aberrations (including higher order aberrations) of the eye(s) by calculating one or more of the following data items in real time in order to minimize the adverse effects of eye movement and/or accommodation on the accuracy of such estimates, the data items including: the geometric reference of nominal null of the sensor, position and shape of the pupil of the eye in the local coordinate system of the sensor, and the pixel subapertures of the imaging device of the sensor that avoid dot crossover.

Another object of the present invention is to provide an ophthalmic instrument that includes a Hartmann style wavefront sensor that estimates the aberrations (including higher order aberrations) of the eye(s), wherein the wavefront sensor is equipped with an improved technique for determining the location of the Hartmann spot in a given pixel subaperture defined around that spot in a manner that provides better performance (e.g., a lower threshold signal-to-noise ratio) under such real-world conditions.

Another object of the present invention is to provide an ophthalmic instrument that includes a Hartmann style wavefront sensor that estimates the aberrations (including higher order aberrations) of the eye(s), wherein the wavefront sensor utilizes an extended source in a manner that improves the signal-to-noise ratio of the wavefront measurements calculated therein.

Another object of the present invention is to provide an ophthalmic instrument that includes a Hartmann style wavefront sensor that projects an image of an extended source onto the retina of the eye(s), captures a plurality of images derived from the retinal reflections of the projected extended source, and applies image correlation techniques in the digital domain to image data derived from the plurality of captured images in order to estimate the local tilt of such retinal reflections. The local tilt estimates are reconstructed to form data representative of the aberrations (including defocus, spherical aberration, coma, astigmatism in addition to other higher order aberrations) of such retinal reflections, which are characteristic of the aberrations of the eye(s) of the patient.

These and other objects of the present invention will become apparent hereinafter and in the claims to Invention.

BRIEF DESCRIPTION OF THE DRAWINGS

For a more complete understanding of the present invention, the following Detailed Description of the Illustrative Embodiment should be read in conjunction with the accompanying Drawings.

DETAILED DESCRIPTION OF THE BEST MODE EMBODIMENTS OF THE INVENTION

Figure 1:
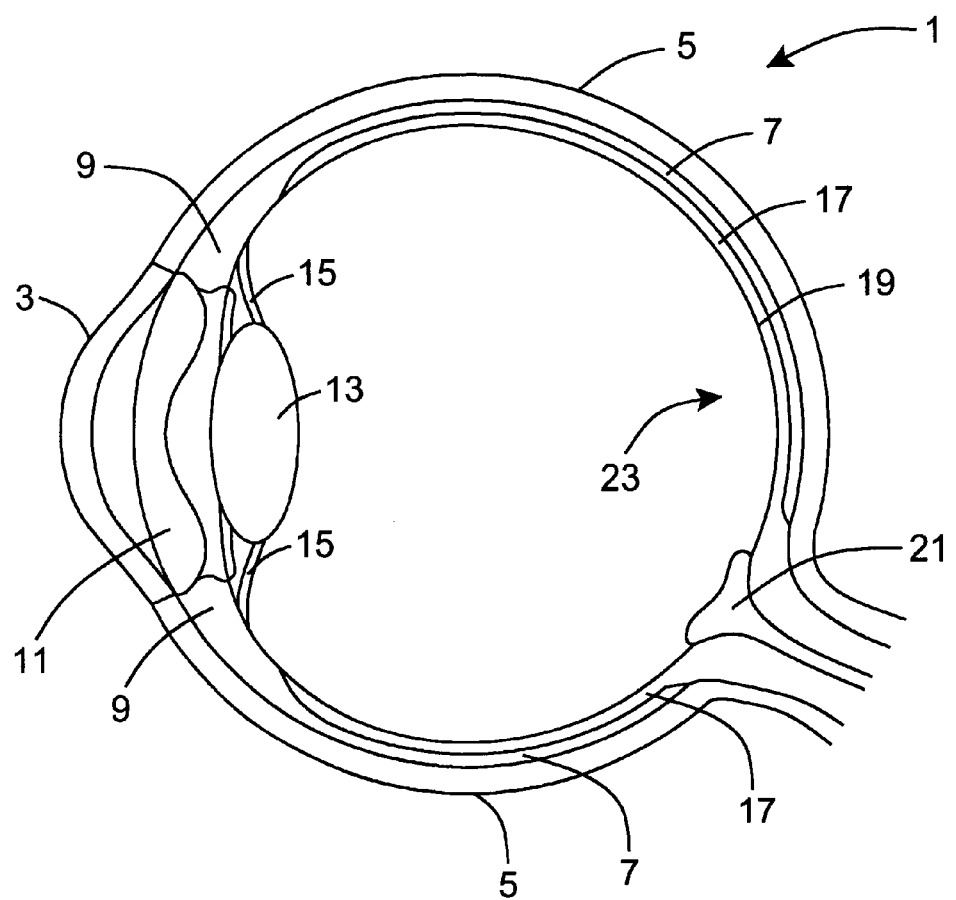
FIG. 1 is a pictorial illustration of a horizontal cross section of the human eye.
Figure 2:
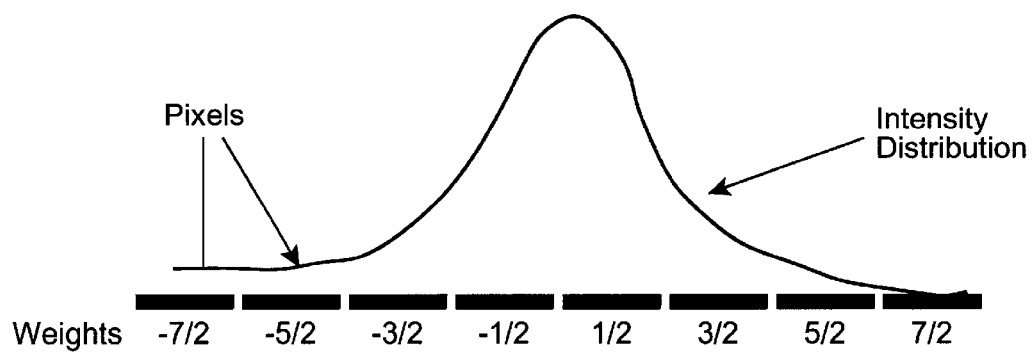
FIG. 2 is one dimensional representation of the intensity distribution on a row of detector pixels and a set of weights for use in prior art techniques for determining the centroid of such detector pixels.

Referring to the figures in the accompanying Drawings, the preferred embodiments of the ophthalmic instruments of the present invention will be described in greater detail, wherein like elements will be indicated using like reference numerals.

According to the present invention, an ophthalmic instrument includes an adaptive optic subsystem that forms an image of a wavefront sensing illumination source on the retina of the eye under examination, which is reflected (thereby exiting the pupil of the eye as distorted wavefronts) and directed back to the instrument. An image of the reflected wavefronts (which represent retroreflection of the image formed on the retina and exit the pupil of the eye as distorted wavefronts) is created on a phase compensator (which preferably comprises a variable focus lens and a deformable mirror) and recreated at a wavefront sensor. The phase compensator operates to spatially modulate the phase of the image of the distorted wavefronts incident thereon. The wavefront sensor measures the phase aberrations in the wavefronts incident thereon and operates in a closed-loop fashion with a controller to control the phase compensator to compensate for such phase aberrations to restore the distorted wavefronts to phase-aligned wavefronts, which are directed to the wavefront sensor (for further wavefront measurement and compensation if required). In this manner, the wavefront sensor and phase compensator compensate for the phase aberrations of the eye under examination. The aberrations of the distorted wavefront measured by the wavefront sensor are characteristic of the aberrations of the eye. The wavefront sensor is preferably operably coupled to a display device that generates a graphical representation (such as a wavefront map that depicts the OPD over the pupil, e.g., subapertures, of the wavefront sensor, or a graphical display of the coefficients of the OPD function) of the aberrations of the eye as measured by the wavefront sensor.

Concurrently therewith, an image of an internal fixation target is created at the phase compensator, which operates to spatially modulate the phase of the image of the fixation target incident thereon to compensate for the aberrations of the eye under examination. The phase compensated image of the fixation target produced by the phase compensator is created at the pupil of the eye under examination. This operation provides the patient with a view of correction (e.g., compensation) of the aberrations of the eye under examination, such the patient can provide instant feedback as to the accuracy of the measurement.

In addition, the ophthalmic instrument may perform imaging operations whereby light from an imaging illumination source is directed onto the pupil of the eye, which is reflected and directed back to the instrument. An image of these reflections is created on the phase compensator, which operates to spatially modulate the phase of this image to compensate for the aberrations of the eye under examination. An imaging device captures an image of the phase-aligned reflections output from the phase compensator. This operation provides the capture (and subsequent processing and display) of high-resolution images of the eye under examination.

As described herein, the present invention is broadly applicable to (and can be embodied within) ophthalmic examination instruments that characterize the optical aberrations of the eye, such as phoropters and autorefractors. In addition, other aspects of the present invention are broadly applicable to (and can be embodied within) any ophthalmic instrument that is used to examine or treat the eye, including ophthalmic examination instruments (such as phoropters and autorefractors) and ophthalmic imaging instruments that capture images of the eye (such as fundus cameras, corneal topographers, retinal topographers, corneal imaging devices, and retinal imaging devices).

Figure 3A:
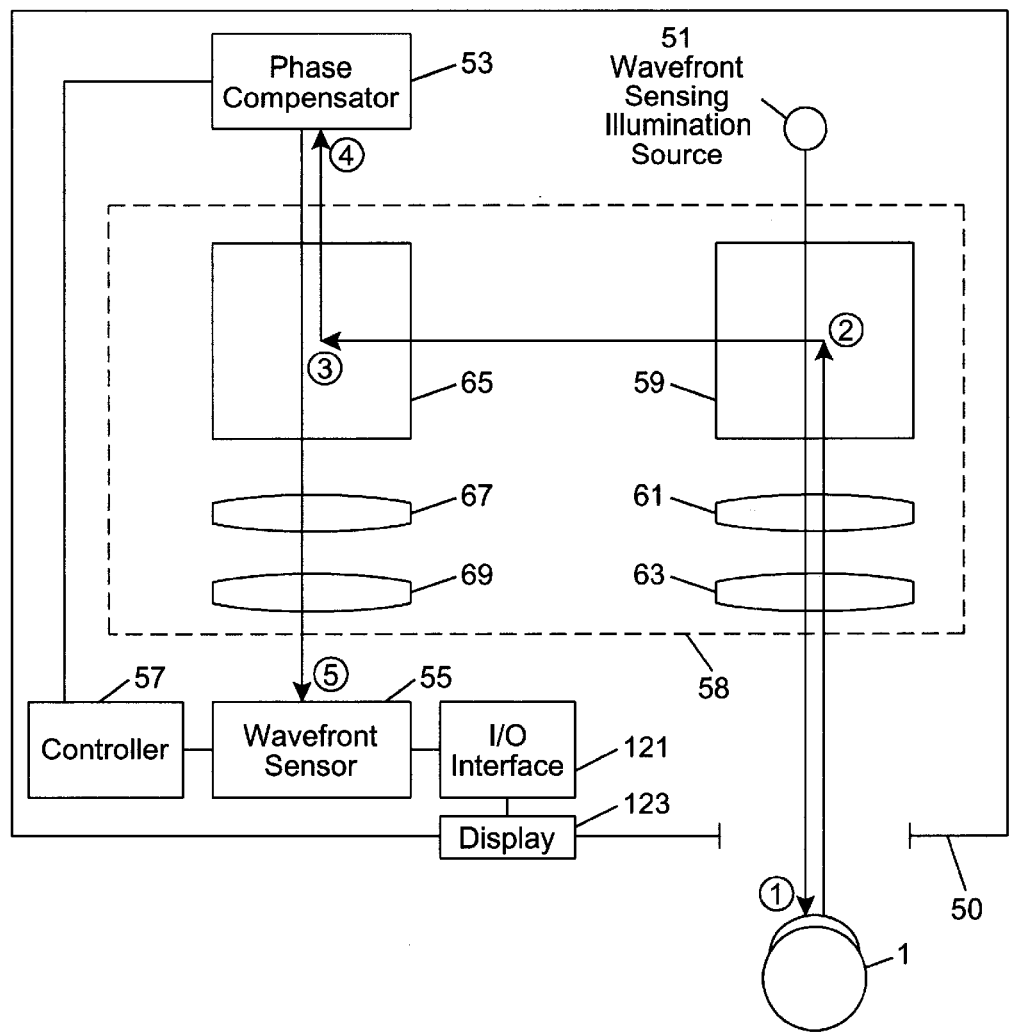
FIG. 3A is a schematic representation of the wavefront sensing components of an exemplary ophthalmic instrument according to the present invention.

Referring now to FIG. 3A, there is shown, in schematic form, the wavefront sensing components of ophthalmic instrument according to the present invention. As shown, the wavefront sensing components include a wavefront sensing illumination source 51 (e.g., a ring of infrared laser diodes with a characteristic wavelength, for example, of 780 nm) that cooperates with optical elements 59 to form an image of the wavefront sensing illumination source 51 on the retina of the eye 1, which is reflected (and exits the pupil of the eye as distorted wavefronts) and directed back to the instrument.

The light produced from the wavefront sensing illumination source 51 forms substantially planar (e.g., phase-aligned) wavefronts that are directed to the pupil of the eye. These planar wavefronts are imaged onto the retina of the eye by the crystalline lens. The image formed on the retina may be a point source image. Alternatively, as described below with respect to FIGS. 25B, 26, 27A and 27B, the image formed on the retina may be an extended source image.

Figure 3B:
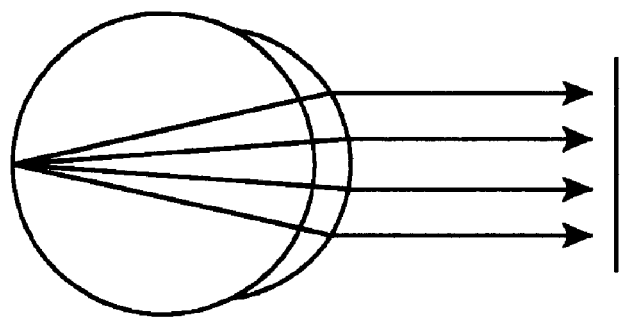
FIG. 3B is a schematic representation depicting the planar wavefront and distorted wavefront produced via reflection of a point source imaged onto the retina of an ideal eye and an aberrated eye, respectively.
Figure 3B:
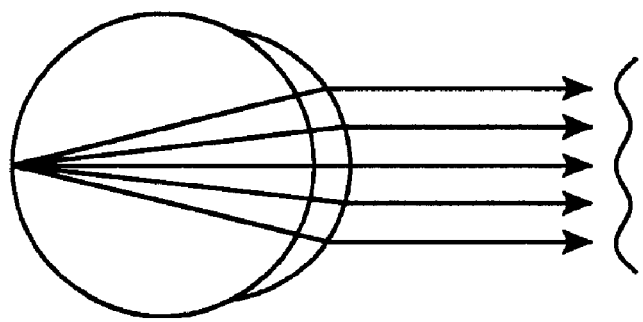

As illustrated in FIG. 3B, the light reflected from the retina of an ideal eye forms planar wavefronts at the pupil of the human eye as it leaves the human eye, while the light reflected from the retina of an aberrated eye forms distorted wavefronts at the pupil of the human eye as it leaves the human eye. The human eye is not ideal and has some form of aberrations such as defocus (which may be myopia (near-sightedness) or hyperopia (far-sightedness)) and astigmatism as well has many other higher order optical aberrations.

The optical elements 59 of the instrument 50 create an image of the reflected wavefronts (which represent retroreflection of the image formed on the retina and exit the pupil of the eye as distorted wavefronts) on a phase compensator 53, which spatially modulates the phase of the image of the reflected wavefronts incident thereon to produce a compensated image of such reflected wavefronts. The optical elements 59 recreate this compensated image at the wavefront sensor 55. The wavefront sensor 55 measures the phase aberrations in the wavefronts incident thereon and operates in a closed-loop fashion with a controller 57 to control the phase compensator 53 to compensate for such phase aberrations to restore the distorted wavefronts to phase-aligned wavefronts, which are directed to the wavefront sensor 55 (for further wavefront measurement and compensation if required). Exemplary control schemes that may be implemented by the controller 57 to control the phase compensator 53 to compensate for such phase aberrations are described by Tyson in "Introduction to Adaptive Optics," SPIE Press, 2000, pgs. 93–109.

The aberrations of the distorted wavefront measured by the wavefront sensor 55 are characteristic of the aberrations of the eye 1. The wavefront sensor 55 is preferably operably coupled (for example, via I/O interface 121) to a display device 123 that generates a graphical representation (such as a wavefront map that depicts the OPD over the pupil, e.g., subapertures, of the wavefront sensor, or a graphical display of the coefficients of the OPD function) of the aberrations of the eye 1 as measured by the wavefront sensor 55.

As shown in FIG. 3A, the optical elements 59 of the instrument 50 preferably include a first polarizing beam splitter 59 and relay lens pair 61/63 that: i) form the image of a wavefront sensing illumination source 51 on the retina of the eye 1, which is reflected (and exits the pupil of the eye as distorted wavefronts) and directed back to the instrument; and ii) direct the reflected wavefronts to a second polarizing beam splitter 65 to create an image of the reflected wavefronts at a phase compensator 53. The phase compensator 53, under control of controller 57, operates to spatially modulate the phase of the image of the reflected wavefronts incident thereon to produce a compensated image of such reflected wavefronts that compensate for the aberrations of the eye under examination. The second polarizing beam splitter 65 and relay lens pair 67/69 recreate this compensated image produced by the phase compensator 53 at the wavefront sensor 55 for wavefront sensing.

Figure 4:
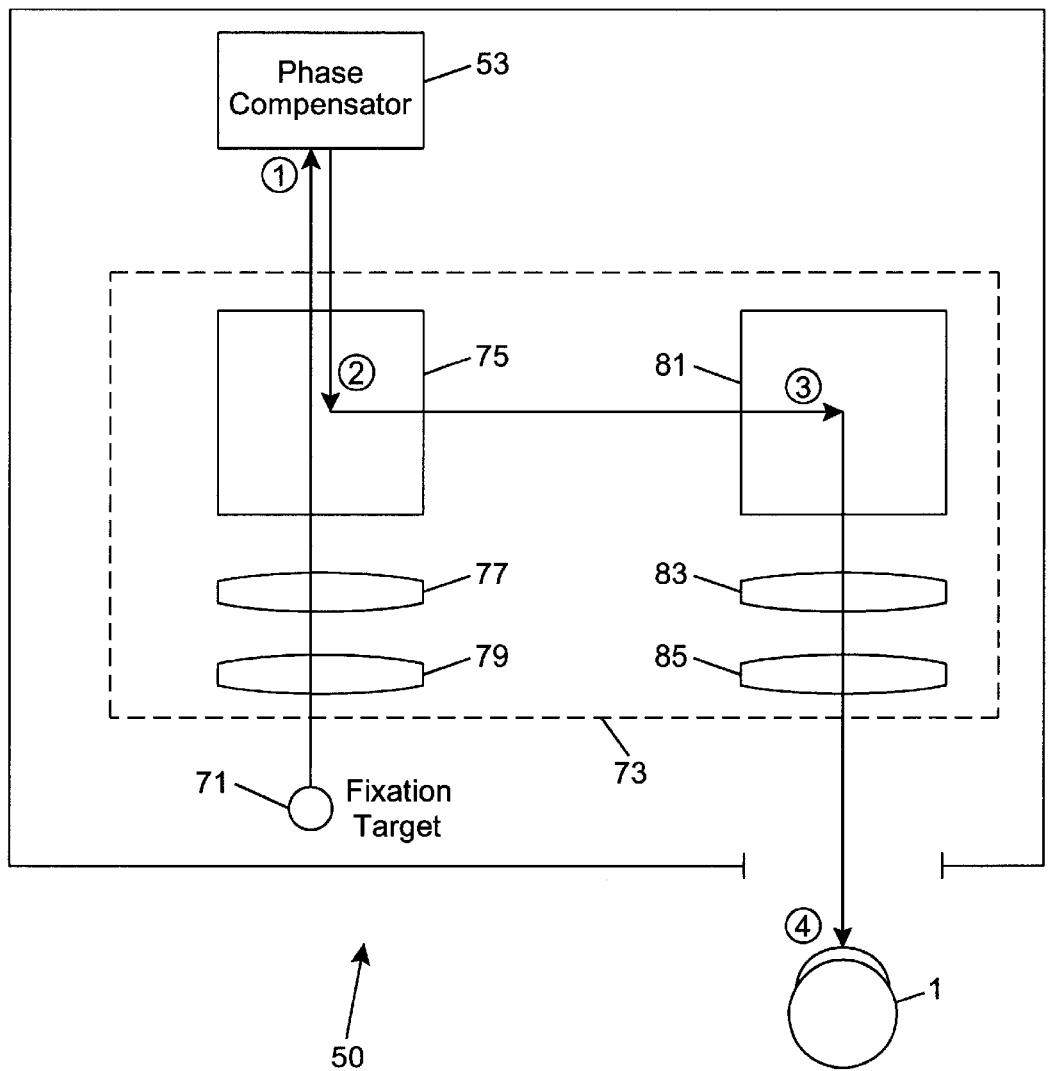
FIG. 4 is a schematic representation of the fixation target components of an exemplary ophthalmic instrument according to the present invention.

Referring now to FIG. 4, there is shown, in schematic form, the fixation target components of an exemplary ophthalmic instrument according to the present invention. As shown, the fixation target components include an internal fixation target 71 (e.g., a visible image source) that cooperates with optical elements 73 to create an image of the internal fixation target 71 at the phase compensator 53. The phase compensator 53, under control of controller 57, operates to spatially modulate the phase of the image of the fixation target 71 incident thereon to compensate for the aberrations of the eye under examination as measured by the wavefront sensor 55. The optical elements 73 recreate the phase compensated image of the fixation target 71 produced by the phase compensator 53 at the pupil of the eye 1 under examination. This operation provides the patient with a view of correction (e.g., compensation) of the aberrations of the eye 1 under examination such the patient can provide instant feedback as to the accuracy of the measurement.

As shown in FIG. 4, the optical elements 73 of the instrument 50 preferably include a relay lens pair 77/79 and first polarizing beam splitter 79 that: i) form an image of the fixation target 71 at the phase compensator 53; and ii) direct the phase compensated image of the fixation target 71 as produced by the phase compensator 53 to a second polarizing beam splitter 81. The second polarizing beam splitter 81 and relay lens pair 83/83 create an image of the phase compensated fixation target at the pupil of the eye 1 under examination.

Figure 5:
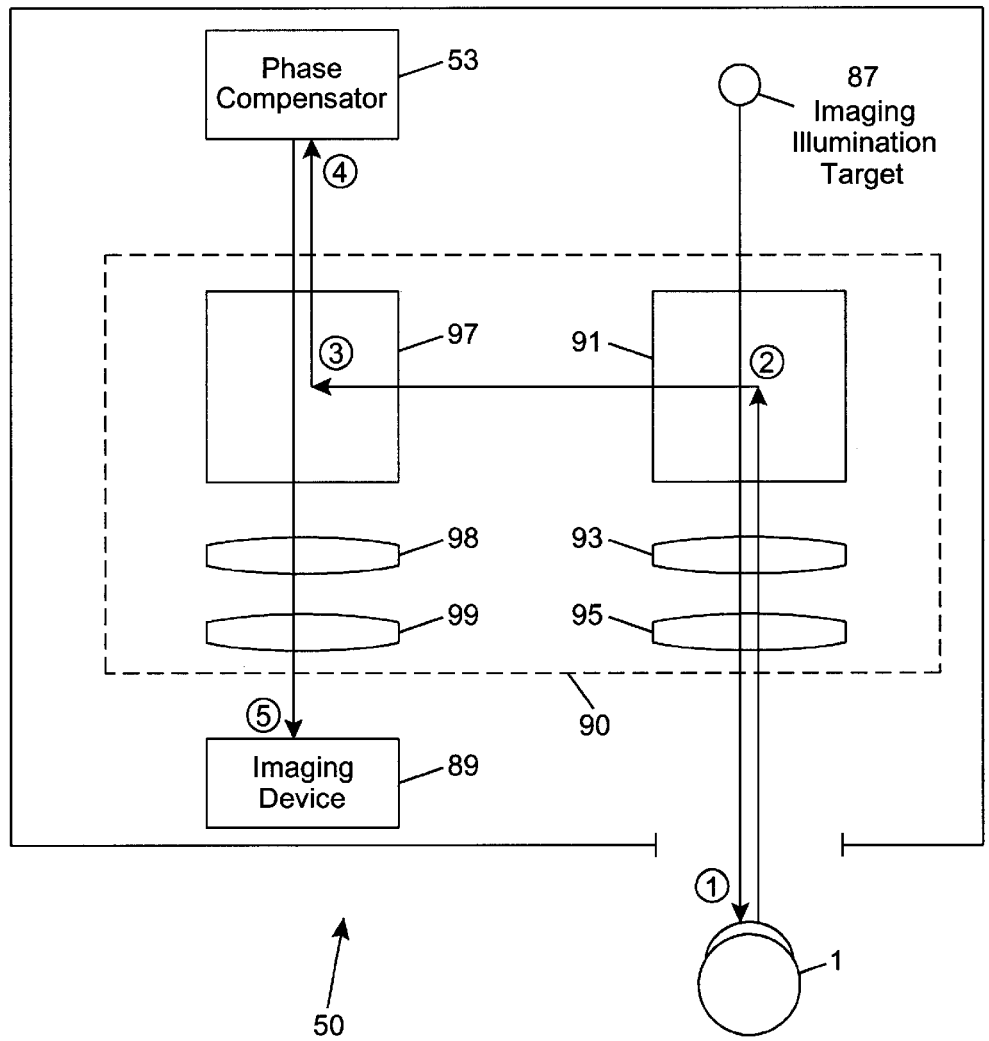
FIG. 5 is a schematic representation of the imaging components of an exemplary ophthalmic instrument according to the present invention.

Referring now to FIG. 5, there is shown, in schematic form, the imaging components of an exemplary ophthalmic instrument according to the present invention. As shown, the imaging components include an imaging illumination source 87 (e.g., halogen flash lamp or xenon flash lamp) that cooperates with optical elements 90 to: i) direct light produced from the imaging illumination source 87 onto the pupil of the eye 1, which is reflected and directed back to the instrument; and ii) create an image of these reflections on the phase compensator 53. The phase compensator 53, under control of controller 57, operates to spatially modulate the phase of such images to compensate for the aberrations of the eye 1 as measured by the wavefront sensor 55. The optical elements 90 recreate these phase compensated images produced by the phase compensator 53 at imaging device 89 (such as a CCD camera body, 3-CCD camera body, CMOS camera body and/or a photographic film unit) for capture. This operation provides the user with the capability of acquiring high-resolution images of the eye. An image storage and output device (not shown) may be operably coupled to the imaging device 89 to thereby store the image data captured by the imaging device 89. In addition, the image storage and output device may communicate (for example, over a high speed serial link such as a USB bus) with an image processing and/or display apparatus (not shown) to output the image data stored therein for display, printing and image processing operations performed by the image processing and display apparatus.

As shown in FIG. 5, the optical elements 90 of the instrument 50 preferably include a first polarizing beam splitter 91 and relay lens pair 93/95 that: i) direct light produced from the imaging illumination source 87 onto the pupil of the eye 1, which is reflected and directed back to the instrument; and ii) direct the reflected wavefronts to a second polarizing beam splitter 97 to thereby create an image of the reflected wavefronts on a phase compensator 53. In addition, the second polarizing beam splitter 97 and relay lens pair 98/99 recreate the phase compensated image produced by the phase compensator 53 at imaging device 89 for capture.

Figure 6A:
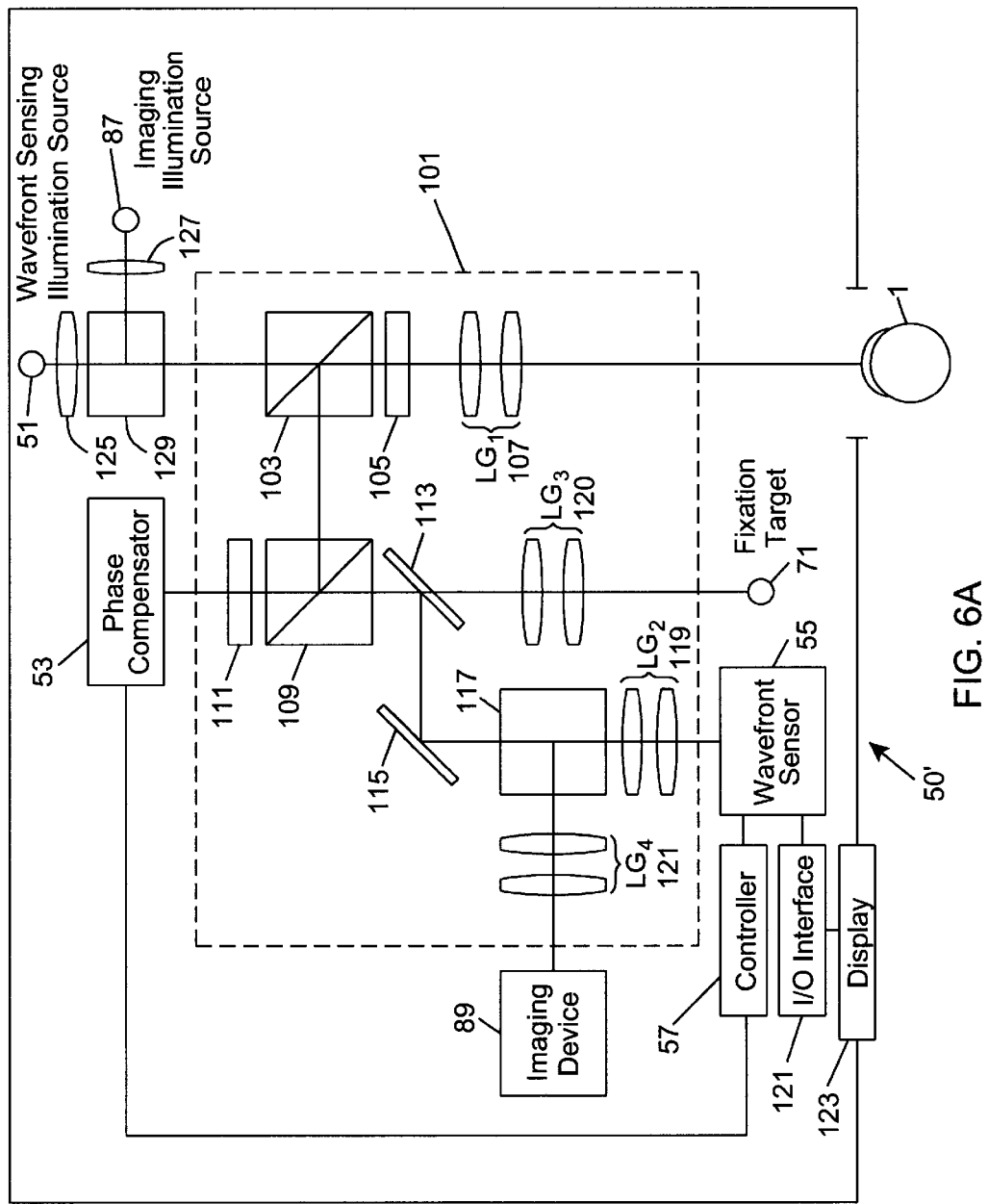
FIGS. 6A and 6B are schematic representations of exemplary embodiments of ophthalmic instruments according to the present invention, including wavefront sensing, an internal fixation target and high resolution image capture capabilities.

Referring now to FIG. 6A there is shown, in schematic form, an exemplary embodiment of an ophthalmic instrument 50' according to the present invention, that provides wavefront sensing, an internal fixation target and high resolution image capture capabilities.

Wavefront sensing is provided by a wavefront sensing illumination source 51 (e.g., a ring of infrared laser diodes with an characteristic wavelength, for example, of 780 nm) that cooperates with lens 125, beam combiner 129, first polarizing beam splitter/quarter wave plate 103/105 and first relay lens group $LG_1$ to form an image of the wavefront sensing illumination source 51 on the retina of the eye 1, which is reflected (and exits the pupil of the eye as distorted wavefronts) and directed back to the instrument. The first relay lens group $LG_1$, first polarizing beam splitter/quarter wave plate 103/105 and second polarizing beam splitter/quarter wave plate 109/111 create an image of these distorted wavefronts on phase compensator 53. The phase compensator 53 operates to spatially modulate the phase of the image of the wavefronts incident thereon. The second polarizing beam splitter/quarter wave plate 109/111, dielectric filter 113, beam folding mirror 117, beam splitter 117 and second relay lens group $LG_2$ recreate the compensated wavefronts produced by the phase compensator 53 at wavefront sensor 55. The dielectric filter 113 operates to selectively reflect the band of light (e.g., infrared light with an characteristic wavelength, for example, of 780 nm) provided by the wavefront sensing illumination source 51 (and used for wavefront sensing) in addition to the band of light provided by the imaging illumination source 97 (and used for image capture), while passing the band of light provided by the fixation target 71. The wavefront sensor 55 measures the phase aberrations in the wavefronts incident thereon (which are derived from retinal reflections of the wavefront sensing illumination source 51) and operates in a closed-loop fashion with controller 57 to control the phase compensator 53 to spatially modulate the phase of the image of the wavefronts incident thereon to compensate for such phase aberrations thereon to thereby restore the distorted wavefronts to phase-aligned wavefronts, which are directed to the wavefront sensor 55 (for further wavefront measurement and compensation if required).

The wavefront sensor 55 is preferably operably coupled (for example, via I/O interface 121) to a display device 123 that generates a graphical representation of the aberrations of the eye 1 as measured by the wavefront sensor 55. For example, the graphical representation of the aberrations of the eye 1 displayed by the display device 123 may be a wavefront map that depicts the OPD over the pupil, e.g., subapertures, of the wavefront sensor, or a graphical display of the coefficients of the OPD function as illustrated in FIG. 6C.

An internal fixation target 71 (e.g., a visible image source) cooperates with a third relay lens group $LG_3$, dielectric filter 113, and second polarizing beam splitter/quarter wave plate 109/111 to create an image of a fixation target 71 at the phase compensator 53. The phase compensator 53, under control of controller 57, operates to spatially modulate the phase of the image of the fixation target 71 to compensate for the aberrations of the eye under examination as measured by the wavefront sensor 55. The second polarizing beam splitter/quarter wave plate 109/111, first polarizing beam splitter/quarter wave plate 103/105, and first lens group $LG_1$ recreate the phase compensated image of the fixation target 71 produced by the phase compensator 53 at the pupil of the eye 1 under examination. This operation provides the patient with a view of correction (e.g., compensation) of the aberrations of the eye 1 under examination such the patient can provide instant feedback as to the accuracy of the measurement.

Image capture is provided by an imaging illumination source 87 (e.g., halogen or xenon flash lamp) that cooperates with lens 127, beam combiner 129, first polarizing beam splitter/quarter wave plate 103/105, and first lens group $LG_1$ to direct light produced from the imaging illumination source 87 onto the pupil of the eye 1, which is reflected and directed back to the instrument. The first lens group $LG_1$, first polarizing beam splitter/quarter wave plate 103/105, and second polarizing beam splitter/quarter wave plate 109/111 create an image of these reflections on the phase compensator 53. The phase compensator 53, under control of controller 57, operates to spatially modulate the phase of such images to compensate for the aberrations of the eye 1 as measured by the wavefront sensor 55. The second polarizing beam splitter/quarter wave plate 109/111, dielectric filter 113, beam folding mirror 117, beam splitter 117 and fourth relay lens group $LG_4$ recreate the compensated image of such reflected wavefronts as produced by the phase compensator 53 at imaging device 89 (such as a CCD camera body, integrating CCD camera body, CMOS camera body and/or a photographic film unit) for capture. This operation provides the user with the capability of acquiring high resolution images of the eye 1.

As is well known in the art, spectral filters that are tuned to the wavelength of the wavefront sensing illumination source 51 and/or imaging illumination source 87 may be disposed along the optical path between the beam splitter 117 and the wavefront sensor 55 and imaging device 89, respectively, in order to reduce background noise and noise from the other illumination sources of the instrument.

Figure 6B:
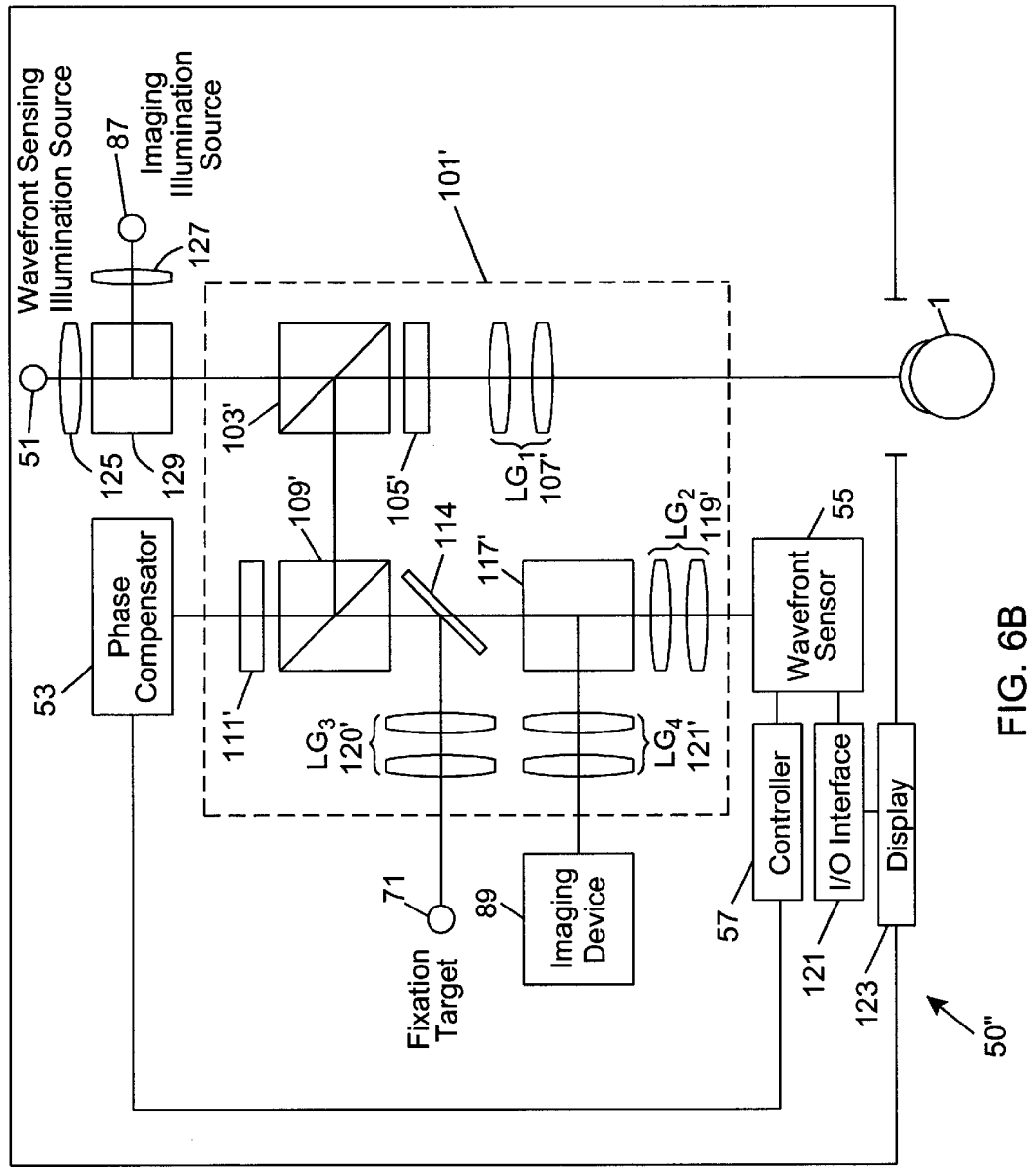
Figure 6C:
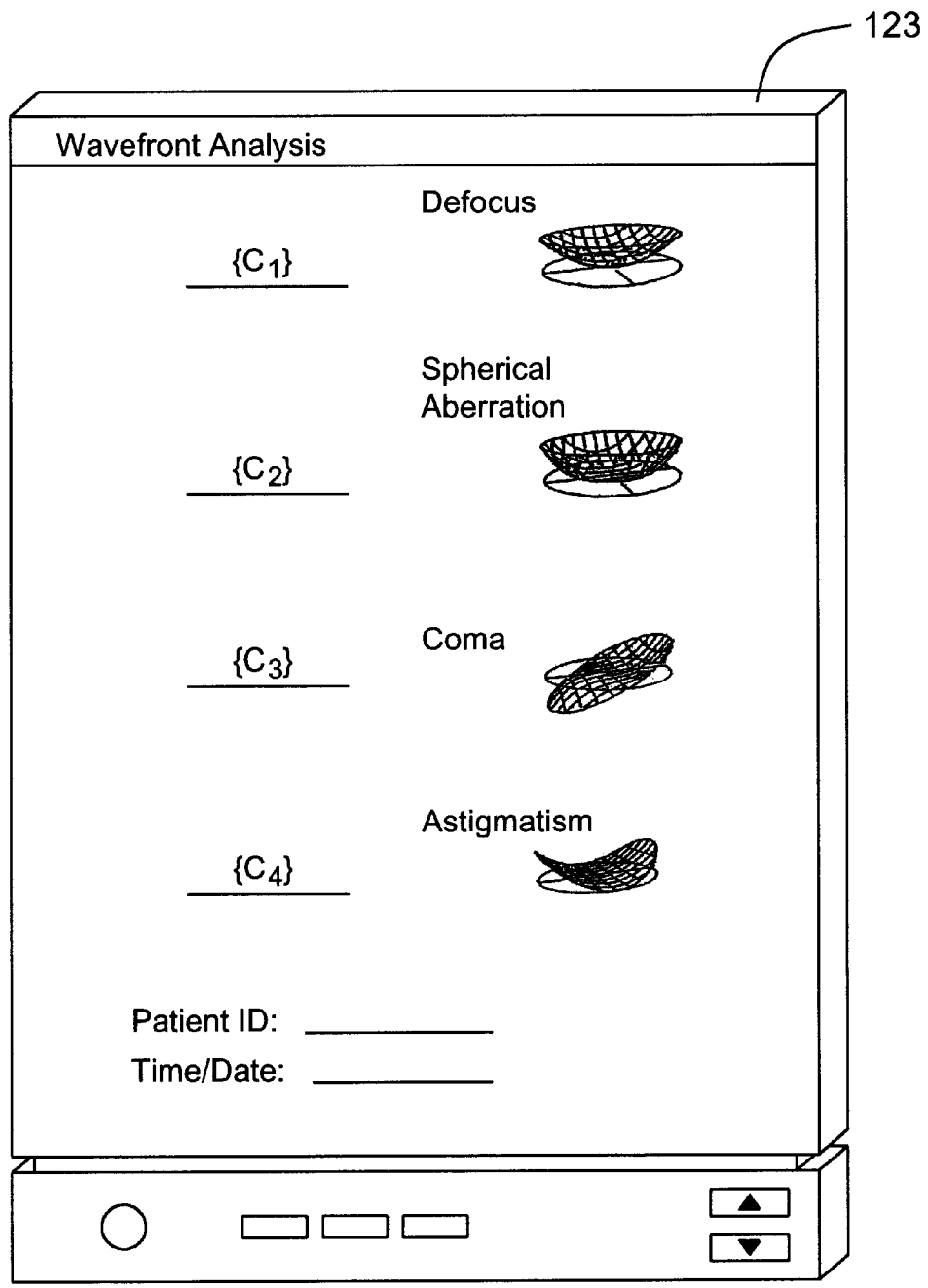
FIG. 6C is a schematic representation of a display viewable on the display device (in addition to a keypad) of the ophthalmic instruments of FIGS. 6A and 6B, wherein the display includes a graphical representation of the aberrations of the human eye (including high order aberrations of the human eye) as measured by the wavefront sensor of the ophthalmic instrument.

Referring now to FIG. 6B there is shown, in schematic form, an exemplary embodiment of an ophthalmic instrument 50" according to the present invention, that provides wavefront sensing, a fixation target and high resolution image capture capabilities.

Wavefront sensing is provided by a wavefront sensing illumination source 51 (e.g., a ring of infrared laser diodes with an characteristic wavelength, for example, of 780 nm) that cooperates with lens 125, beam combiner 129, first polarizing beam splitter/quarter wave plate 103'/105' and first relay lens group $LG_1$ to form an image of a wavefront sensing illumination source 51 on the retina of the eye 1, which is reflected (and exits the pupil of the eye as distorted wavefronts) and directed back to the instrument. The first relay lens group $LG_1$, first polarizing beam splitter/quarter wave plate 103'/105' and second polarizing beam splitter/quarter wave plate 109'/111' create an image of the distorted wavefronts on a phase compensator 53. The phase compensator 53 operates to spatially modulate the phase of the wavefronts incident thereon. The second polarizing beam splitter/quarter wave plate 109'/111', dielectric filter 114, beam splitter 117' and second relay lens group $LG_2$ recreate the image of such compensated wavefronts at wavefront sensor 55. The dielectric filter 114 operates to selectively reflect the band of light provided by the fixation target 71, while passing the band of light (e.g., infrared light with an characteristic wavelength, for example, of 780 nm) provided by the wavefront sensing illumination source 51 (and used for wavefront sensing) in addition to the band of light provided by the imaging illumination source 97 (and used for image capture). The wavefront sensor 55 measures the phase aberrations in the wavefronts incident thereon (which are derived from retinal reflections of the wavefront sensing illumination source 51) and operates in a closed-loop fashion with a controller 57 to control the phase compensator to spatially modulate the phase of the wavefronts incident thereon to compensate for such phase aberrations (by warping it's surface to form the complex conjugate of the measured errors) to thereby restore the distorted wavefronts to phase-aligned wavefronts, which are directed to the wavefront sensor 55 (for further wavefront measurement and compensation if required).

The wavefront sensor 55 is preferably operably coupled (for example, via I/O interface 121) to a display device 123 that generates a graphical representation of the aberrations of the eye 1 as measured by the wavefront sensor 55. For example, the graphical representation of the aberrations of the eye 1 displayed by the display device 123 may be a wavefront map that depicts the OPD over the pupil, e.g., subapertures, of the wavefront sensor, or a graphical display of the coefficients of the OPD function as illustrated in FIG. 6C.

The fixation target is provided by an internal fixation target 71 (e.g., a visible image source) that cooperates with a third relay lens group $LG_3$, dielectric filter 114, and second polarizing beam splitter/quarter wave plate 109'/111' to create an image of the internal fixation target 71 at the phase compensator 53. The phase compensator 53, under control of controller 57, operates to spatially modulate the phase of the image of the fixation target 71 to compensate for the aberrations of the eye under examination as measured by the wavefront sensor 55. The second polarizing beam splitter/quarter wave plate 109'/111', first polarizing beam splitter/quarter wave plate 103'/105,' and first lens group $LG_1$ recreate the phase compensated image of the fixation target 71 produced by the phase compensator 53 at the pupil of the eye 1 under examination. This operation provides the patient with a view of correction (e.g., compensation) of the aberrations of the eye 1 under examination such the patient can provide instant feedback as to the accuracy of the measurement.

Image capture is provided by an imaging illumination source 87 (e.g., halogen or xenon flash lamp) that cooperates with lens 127, beam combiner 129, first polarizing beam splitter/quarter wave plate 103'/105', and first lens group $LG_1$ to direct light produced from the imaging illumination source 87 onto the pupil of the eye 1, which is reflected and directed back to the instrument pupil. The first lens group $LG_1$, first polarizing beam splitter/quarter wave plate 103'/105', and second polarizing beam splitter/quarter wave plate 109'/111' create an image of these reflections on the phase compensator 53. The phase compensator 53, under control of controller 57, operates to spatially modulate the phase of such images to compensate for the aberrations of the eye 1 as measured by the wavefront sensor 55 The second polarizing beam splitter/quarter wave plate 109'/111', dielectric filter 114, beam splitter 117' and fourth relay lens group $LG_4$ recreate the compensated image of such reflected wavefronts as produced by the phase compensator 53 at imaging device 89 (such as a CCD camera body, 3-CCD camera body, CMOS camera body and/or a photographic film unit) for capture. This operation provides the user with the capability of acquiring high resolution images of the eye 1.

As is well known in the art, spectral filters that are tuned to the wavelength of the wavefront sensing illumination source 51 and/or imaging illumination source 87 may be disposed along the optical path between the beam splitter 117' and the wavefront sensor 55 and imaging device 89, respectively, in order to reduce background noise and noise from the other illumination sources of the instrument.

In addition, the ophthalmic instrument of the present invention preferably includes the following components (which, while not shown in the Figures in order to simplify the diagram, are assumed provided in the system described herein):

Headband and chinrest: the patient is positioned at the instrument with his forehead against the band and his chin in the chinrest.

Chinrest adjusting knob: the vertical distance between the forehead band and the chinrest is adjusted with this knob.

Fixation Target Control knob(s): controls the working distance (and possibly lateral movement in the plane perpendicular to the optical axis) of the instrument, and possibly size (i.e., scale)) of the internal fixation target 71.

Typically, the working distance of the internal fixation target 71 is set to infinity in order to limit the accommodation of the eye during wavefront sensing, and/or imaging operations.

The wavefront sensor 55 of the ophthalmic instrument of the present invention preferably comprises a Shack-Hartmann wavefront sensor, which includes an array of small lenslets disposed in front of an imaging device (such as a CCD camera body, integrating CCD camera body or CMOS camera body). The lenslets partition the incident wavefront into a large number of smaller wavefronts, each of which is focused to a small spot on the imaging device. The spatial location of each spot is a direct measure of the local tilt (sometimes referred to as local slope or local gradient) of the incident wavefront. The Shack-Hartmann wavefront sensor includes signal processing circuitry (for example, a digital signal processor) that samples the output of the imaging device and processes the data output there from to track the spatial positions of these spots to derive the local tilt (e.g., local gradients) of the incident wavefronts. These local gradients are reconstructed to form data representative of the aberrations of the distorted wavefronts (including defocus, spherical aberration, coma, astigmatism in addition to other higher order aberrations of the distorted wavefronts). For example, the local gradients may be reconstructed into an optical path difference (OPD) array, which stores a scalar value that represents the optical path difference at each lenslet. Alternatively, the local gradients may be reconstructed into an OPD function, for example, by minimizing the difference between the derivatives of an analytical function (such as a set of Zernike polynomials, Seidel polynomials, Hermites polynomials, Chebychev polynomials, and Legendre polynomials) and the measured local gradients. A more detailed description of exemplary Shack-Hartman wavefront sensor configurations are described below. Alternate wavefront sensing techniques are described in detail in Geary, "Introduction to Wavefront Sensors", SPIE Optical Engineering Press, 1995, pp. 53–103.

Alternatively, the wavefront sensor 55 may comprise a Tscherning wavefront analyzer that illuminates the eye with a dot pattern formed by a laser source and dot pattern mask. The reflected dot pattern is captured by the imaging device and the image data is analyzed to derive deviations in the dot pattern from its ideal locations. From the resulting deviations, aberrations in the distorted wavefronts produced from the subject eye are mathematically reconstructed. A more detailed description of a Tscherning wavefront analyzer is described by Mierdel et al. in "A measuring device for the assessment of monochromatic aberrations of the eye," Ophthamologe, 1997, Vol. 94, pgs. 441–445, and Mrochen et al., "Principles of Tscherning Aberrometry," J of Refractive Surgery, Vol. 16, September/October 2000.

Alternatively, the wavefront sensor 55 may comprise a spatially resolved refractometer as described in detail by He et al. in "Measurement of the wave-front aberration of the eye by fast psychophysical procedure," J Opt Soc Am A, 1998, Vol. 15, pgs. 2449–2456 and in U.S. Letters Pat. No. 5,258,791 and 6,000,800, each incorporated herein by reference in its entirety.

Alternatively, the wavefront sensor 55 may comprise any one of the improved wavefront sensor configurations described below in conjunction with FIGS. 20A–20D or FIG. 22, or FIGS. 25B, 26, 27A and 27B.

The wavefront sensor 55 measures the aberrations (including defocus, spherical aberration, coma, astigmatism in addition to other higher order aberrations) of the distorted wavefronts (produced by retinal reflection of light produced by the wavefront sensing illumination source 51). The aberrations measured by the wavefront sensor 55 represent the aberrations of the subject eye (including high order aberrations of the eye such as spherical aberration, astigmatism and coma). The wavefront sensor 55 supplies data representative of these aberrations (such as an OPD array or OPD function) to the controller 57, which controls the phase compensator 53 to restore the distorted wavefronts (which are derived from retinal reflections of the wavefront sensing illumination source 51) to phase-aligned wavefronts, which are directed to the wavefront sensor 55 (for further wavefront measurement and compensation if required).

Figure 7A:
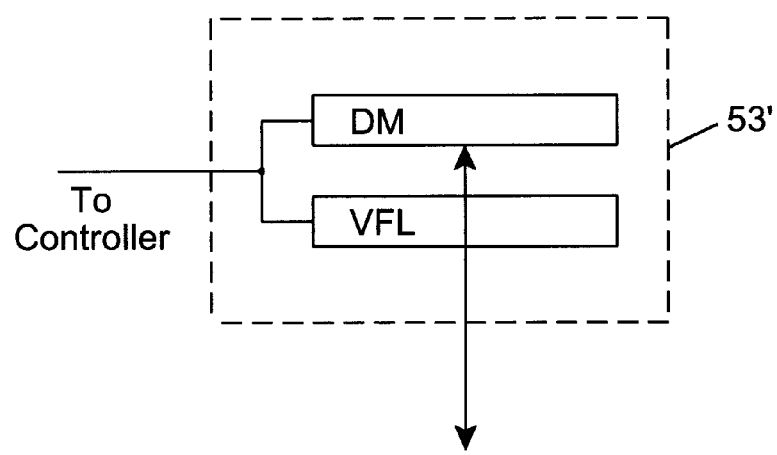
FIGS. 7A and 7B are functional block diagrams that illustrate a multi-stage phase compensator that is embodied as part of an adaptive optic-based ophthalmic instrument according to the present invention.
Figure 7B:
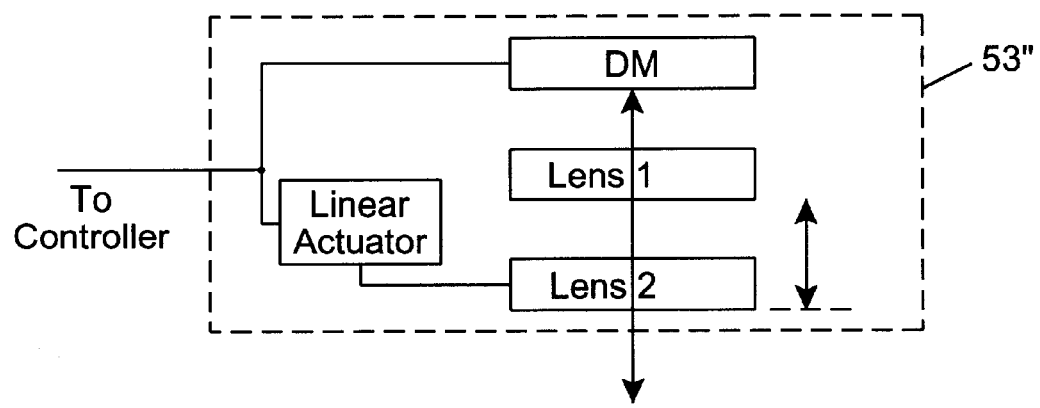

In another aspect of the present invention, as illustrated in FIG. 7A, the phase compensator 53 embodied within the adaptive optic subsystem of an ophthalmic instrument (including the ophthalmic instruments described above) preferably comprises multiple stages (such as the variable focus lens (VFL) and a deformable mirror as shown) that compensate for different parts of the aberrations of the eye 1 as estimated by the wavefront sensor 55. For example, the wavefront sensor 55 (or the controller 57) can decompose such aberrations into a defocus component (which represents the defocus of the eye 1) and one or more additional components which represent the higher order components (e.g., spherical aberration, astigmatism and coma) of such aberrations. In this case, controller 57 controls the first stage (i.e., the variable focus lens) to compensate for the defocus component of such aberrations, and controls the one or more additional stages (i.e., a deformable mirror) to compensate for the remaining higher order components of such aberrations. A deformable mirror achieves such compensation by warping its optical surface to form the complex conjugate of such higher order components as measured by the wavefront sensor 55. In ophthalmic applications where defocus is the primary component of the aberrations of the eye, such a configuration improves the dynamic range of the phase compensation operation performed by the adaptive optic subsystem. As illustrated in FIG. 7B, the variable focus lens may comprise a stationary first lens 1, and a second lens 2 that is moved linearly with respect to the first lens along the optical axis of the first and second lens and deformable mirror by an actuator a shown.

Figure 8A:
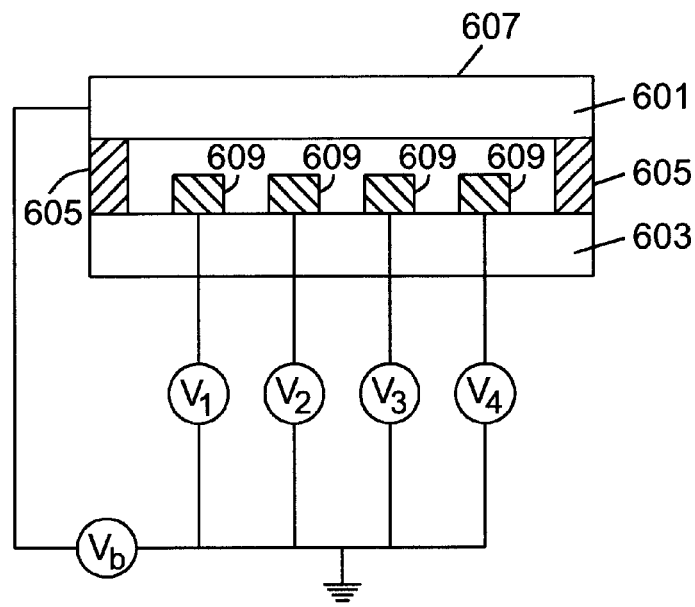
FIGS. 8A and 8B are pictorial illustrations of a silicon micro-machined membrane deformable mirror that may be embodied as part of the phase compensator of the adaptive optic-based ophthalmic instrument of the present invention.
Figure 8B:
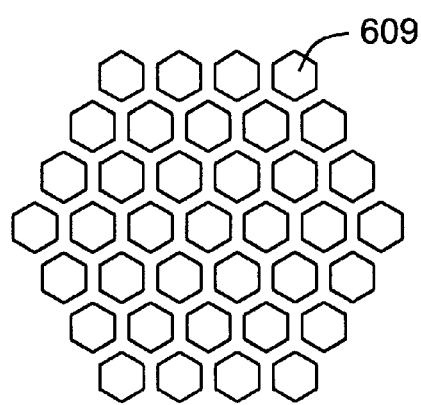

Silicon micro-machined membrane mirrors (which is a class of deformable mirrors that are readily available, for example, from OKO Technologies of Deelft, the Netherlands) are suitable for phase compensation for many ophthalmic imaging applications. As illustrated in FIG. 8A, such mirrors typically consist of a silicon chip 601 mounted over a printed circuit board substrate 603 by spacers 605. The top surface 607 of the chip 603 contains a membrane (typically comprising silicon nitride) which is coated with a reflective layer (such as aluminum or gold) to form the mirror surface. The printed circuit board 603 contains a control electrode structure (as illustrated in FIG. 8B) that operates to deform the shape of the reflective membrane by applying bias and control voltages to the membrane and the control electrodes 609.

Other classes of deformable mirrors (including segmented mirrors, continuous faceplate mirrors, and edge actuated mirrors) suitable for phase compensation for many ophthalmic applications are described by Tyson in "Introduction to Adaptive Optics," SPIE Press, 2000, pgs. 83–91, supra. In addition, classes of liquid crystal devices are suitable for phase compensation for many ophthalmic applications.

Proper alignment (and focus) of the optical elements of the ophthalmic instrument 50 (including the optical elements of the wavefront sensor 55) is required for optimal operations. In addition, proper alignment of the eye 1 to the ophthalmic instrument 50 (or proper alignment of the ophthalmic instrument 50 to the eye 1) is also required for optimal operations.

Preferably, alignment of the optical elements of ophthalmic instrument 50 is accomplished by user manipulation of one or more control levers (or joystick(s)) that control forward/backward, side-to-side, and vertical alignment of the optical elements of the instrument 50. Gross alignment of the instrument 50 is preferably accomplished by sliding the base of the instrument 50 in the desired direction. Focus of the instrument 50 is preferably controlled by one or more focusing knobs that cooperate with the optical elements of the instrument to adjust focus of the instrument 1.

Proper alignment of eye 1 to the instrument 50 may be accomplished with a headband and chin rest whereby the patient is positioned at the instrument 50 with his/her forehead against the headband and his/her chin in the chinrest. One or more adjusting knobs may be used to adjust the position of the subject eye such that it is properly aligned with the optical axis of the instrument 50. Alternatively, the position (and orientation) of the instrument 50 may be changed such that it is properly aligned with the eye 1. This step is suitable for handheld ophthalmic devices. Such alignment is preferably accomplished through the use of cross-hairs and an infrared distance detector embodied within the instrument 50. The cross-hairs are centered in the field of view of the instrument 50 and viewable to the user such that the user can accurately position the cross hairs onto the pupil of the eye 1. The infrared distance detector provides visible feedback (i.e., varying frequency flicker lights) or audible feedback (different pitched beeps) that enables the user to accurately position and orient the optical axis of the instrument 50 with respect to the eye 1.

Figure 9:
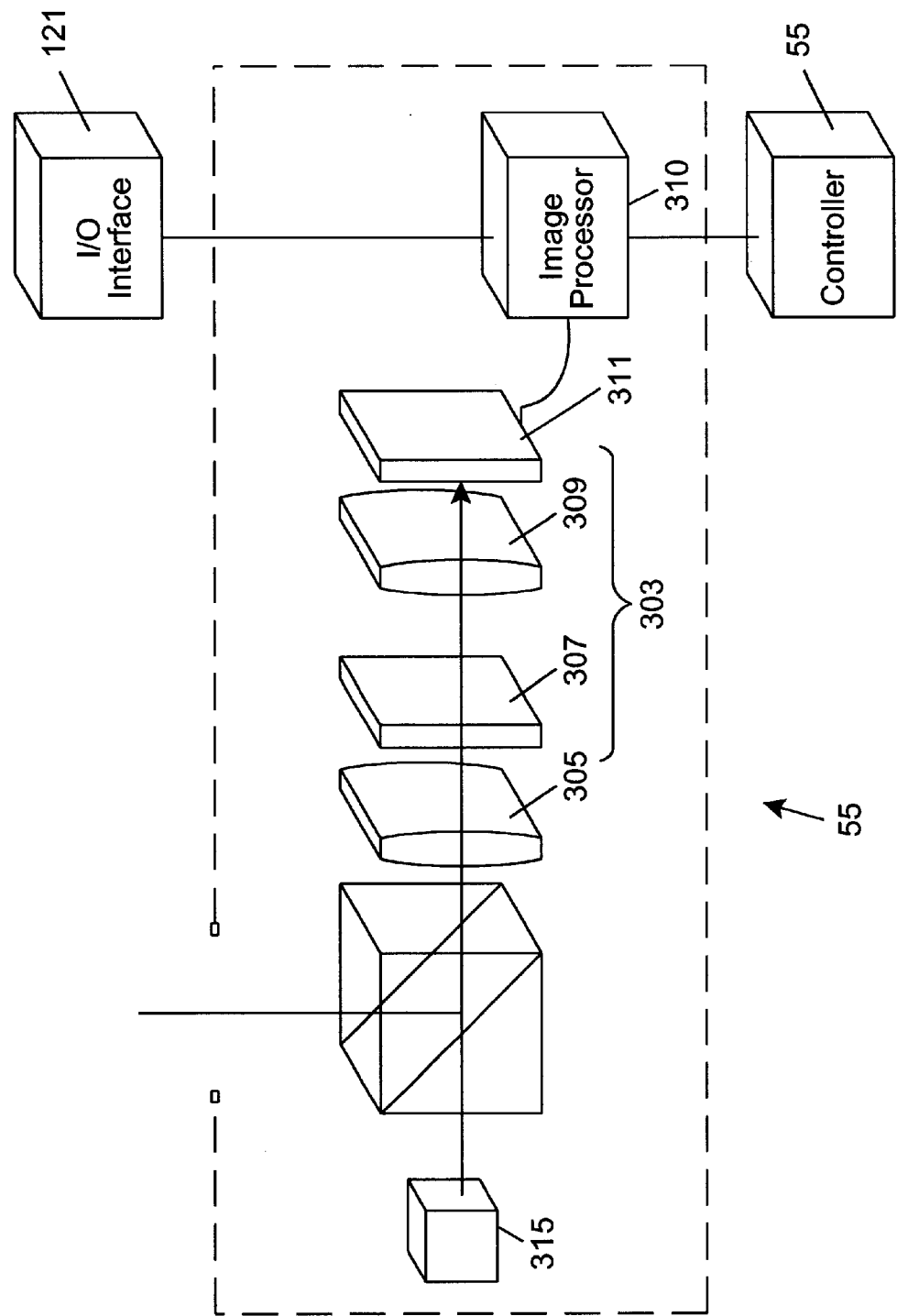
FIG. 9 is a schematic illustration of exemplary Shack-Hartmann wavefront sensing components that may be embodied within the ophthalmic instruments of the present invention.

FIG. 9 illustrates exemplary Shack-Hartmann wavefront sensing components that can embodied within the ophthalmic instruments of the present invention. As shown in FIG. 9, these components include foreoptics 301 and a wavefront sensor head 303. The foreoptics 301, which preferably include a beam combiner 304 and collimating lens 305 as shown, operate in conjunction with the optical elements of the instrument to form an image of the distorted wavefronts (which are formed via reflection of the image of the wavefront sensing illumination source 51 on the retina of the eye 1) in the plane of a lenslet array 307. The lenslet array 307 partitions the incident wavefront into a large number of smaller wavefronts and forms corresponding focal spots (e.g., Hartmann spot pattern). A relay lens 309 images the Hartmann spot pattern on an imaging device 311 (such as a CCD camera body, a CMOS camera body, or an integrating CCD camera body). The imaging device 311 is operably coupled to an image processor 310 that grabs the image data captured by the imaging device 311, processes the grabbed image data to track spot movement in the Hartmann spot pattern, derives a measure of the local tilt of the distorted wavefronts at the lenslets from such test spot movements, and possibly stores such image data in persistent storage. In addition, the image processor 310 generates data (such as an OPD array or OPD function) representative of the aberrations of the distorted wavefronts (including defocus, spherical aberration, coma, astigmatism in addition to other higher order aberrations of the distorted wavefronts) from such measures. In adaptive optic applications, such as the ophthalmic instruments described above, such data is provided to a controller which controls a phase-compensating optical element(s) to compensate for such phase aberrations to restore the distorted wavefronts to phase-aligned wavefronts.

Figure 10A:
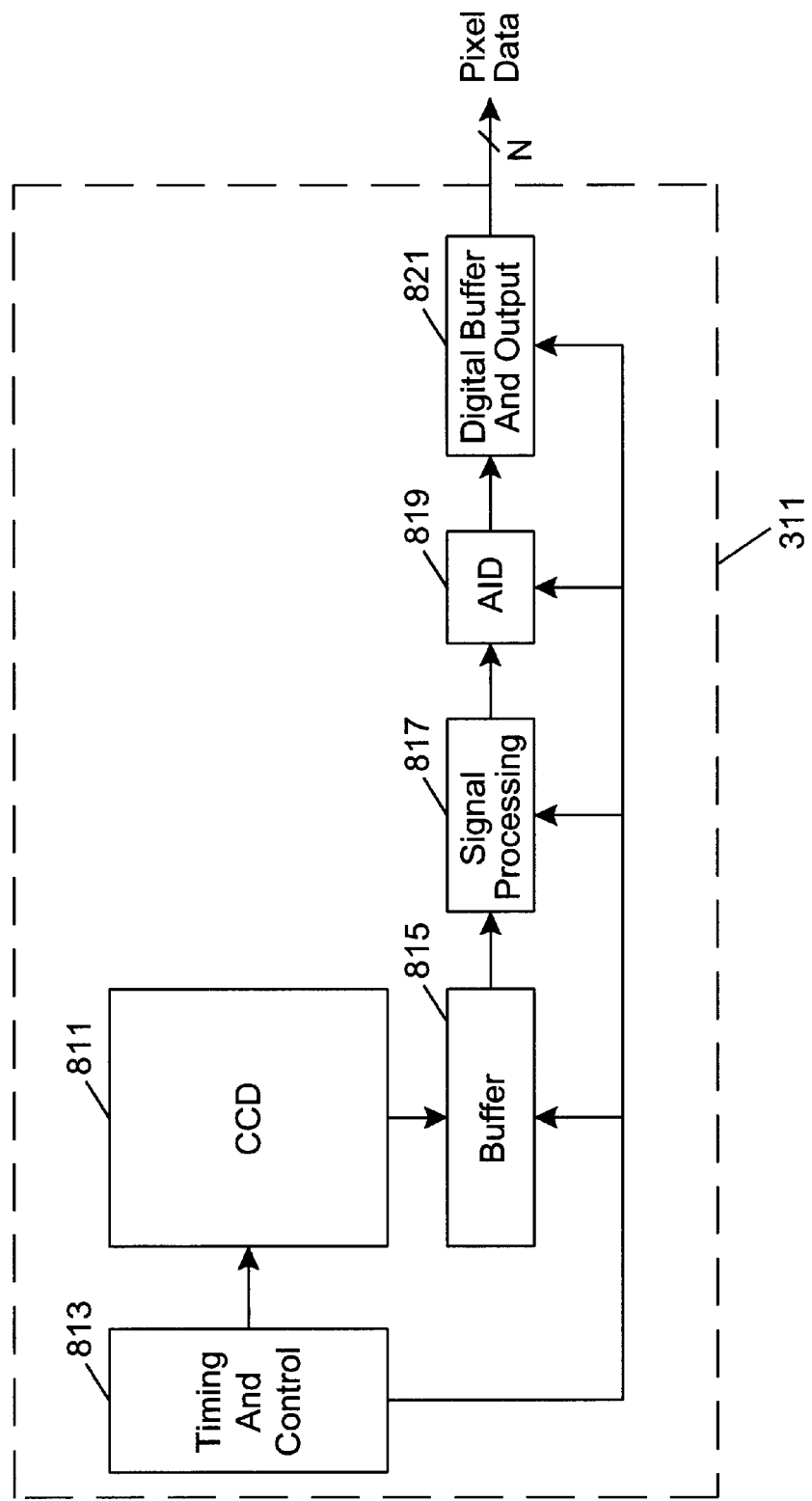
FIG. 10A is a functional block diagram of an exemplary embodiment of the components of imaging device 311 of FIG. 9.

FIG. 10A illustrates an exemplary embodiment of the components of imaging device 311 of FIG. 9, including a CCD array 811 of photodetectors that detect the intensity of incident light thereon and generate an electrical signal in response thereto, timing and control circuitry 813 that supply timing signals to the CCD array 811 to: read out the electrical signals generated by the elements therein, store the signals in buffer 815, output the signals stored in buffer 815 to signal processing circuitry 817 that condition such signals for analogue-to-digital conversion circuitry 819, and store digital data words (pixel data words) derived from such signals in digital buffer and output circuitry 821 for output to image processing. Alternatively, a CMOS array or integrating CCD array may be substituted for the CCD array 811.

Figure 10B:
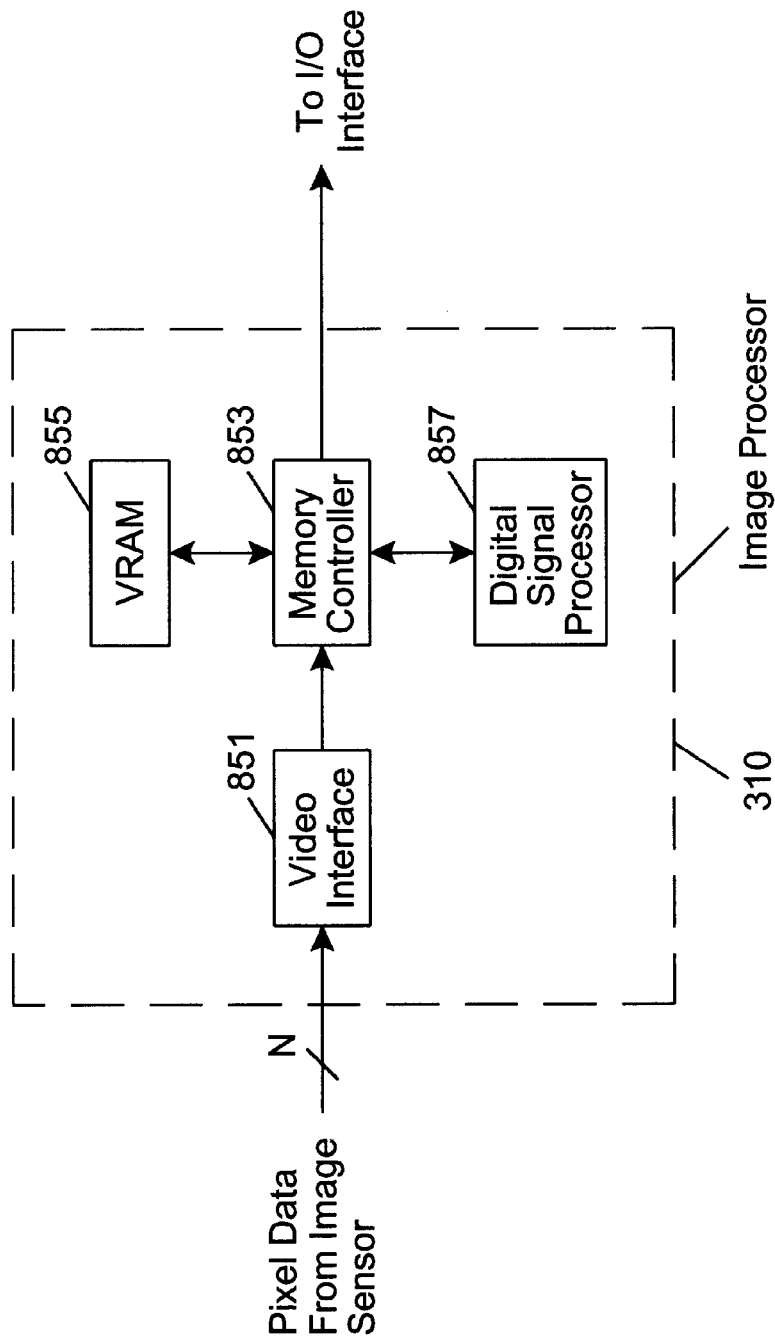
FIG. 10B is a functional block diagram of an exemplary embodiment of the components of image processor 310 of FIG. 9.

FIG. 10B illustrates an exemplary embodiment of the components of image processor 310 of FIG. 9, including a memory controller 853 that provides access to memory 855 for interface 851, digital signal processor 857. Interface 851 inputs pixel data words from the imaging device 311 and stores such pixel data words in memory 855 via memory controller 853. The digital signal processor 857 accesses the pixel data stored in memory 855 and processes such data in accordance with a sequence of programmed instructions. The memory controller 853 also communicates with an I/O interface to thereby display data on a display device (such as a TFT LCD device).

Figure 11:
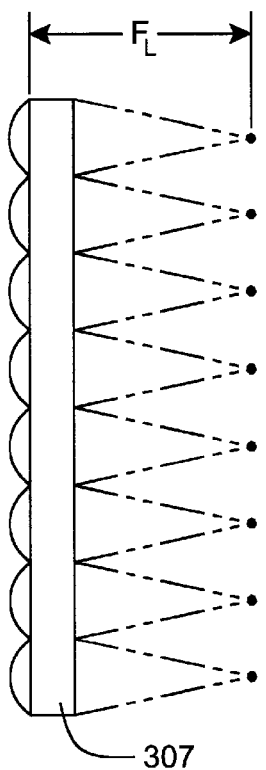
FIG. 11 is a pictorial representation of the Hartmann spot pattern that is formed at approximately a lenslet focal length $f_L$ behind the lenslet array of the Shack-Hartmann wavefront sensor of FIG. 9.

As illustrated in FIG. 11, the Hartmann spot pattern is formed at approximately a lenslet focal length $f_L$ behind the lenslet array 307. For a number of reasons, it is desirable to use relay lens 309 to relay the Hartmann spot pattern onto the imaging device 311. First, this allows the matching of the scale of the Hartmann spot pattern to the pixel size of the imaging device 311. Second, it simplifies the implementation of interchangeable lenslets (of varying focal length and/or aperture size). Finally, it allows the wavefront sensor head 303 to gather a much wider range of data on the optical system under test and, as a result, make measurements of greater accuracy. Preferably, the relay lens 309 operates in a telecentric mode to minimize the possibility of magnification errors that lead to wavefront estimation errors.

The lenslet array 307 may be of the type manufactured and sold by Adaptive Optics Inc, of Cambridge, Mass., assignee of the present invention, in that it comprises a precision array of refractive microlenses formed continuously on a monolithic substrate. The array of microlenses are preferably compression molded of polymethymethacrylate (PMMA) plastic, and positioned in the substrate with full edge-to-edge lenslet contact to maximize the density of lens area to total surface area (referred to as "fill factor"). The fill factor determines how much of the scaled full aperture system pupil (the subject eye under examination) is captured by the array. The commercial lenslet arrays manufactured and sold by assignee of the present invention have fill factors exceeding 98 percent.

As described above, the Shack-Hartmann wavefront sensing head 303 derives local wavefront tilt at a given lenslet from spot motion for the given lenslet. Such derivation inherently depends upon the particular geometry of the sensor head and its optics (including the distance between the pupil image plane and the spot image plane, the radius of the pupil of the lenslet, and possibly the refractive index of the lenslet) and requires a geometric reference of the nominal null (i.e., spot location corresponding to incident of a planar wavefront on a given lenslet). A more detailed description of the derivation for relating spot motion to local wavefront tilt is described in detail by Geary in "Introduction to Wavefront Sensors", SPIE Optical Engineering Press, 1995, pp.14–20. Because the distance between the pupil image plane and the spot image plane and the radius of the pupil of the lenslet (which is set by the size of the individual lenslet elements) are both quantities that are determined at the time of manufacture, this basic parameters need not be re-measured each time the system is used.

There are, however, a number of parameters related to a particular wavefront measurement that must be determined before that particular wavefront measurement can be made. These parameters include the geometric reference of nominal null and, possibly, the position and shape of the system pupil (e.g., the pupil of the eye under test) in the local coordinate system of the wavefront sensing head 303. The shape of the system pupil is primarily used for the calculation of polynomial decompositions of the wavefront. For example, Zernike and Seidel polynomial decompositions are derived from a circular pupil, whereas Monomials, Hermites, Chebychev, and Legendre polynomial decompositions are derived from a rectangular pupil. However, selection of the pupil shape has no direct effect on the wavefront measurement itself. In cases where there is no well defined pupil, any convenient pupil may be selected.

Geometric Reference of Nominal Null

The Shack-Hartmann wavefront sensor (which is preferably embodied within the ophthalmic instruments of the present invention) may utilize one of a number of different approaches in achieving the geometric reference to nominal null.

A first approach achieves this geometric reference by a reference plane wave (generated by a laser source and suitable collimating optical elements) that is recreated at the plane of the lenslet array 307. The Hartmann spot pattern, which is formed at approximately a lenslet focal length $f_L$ behind the lenslet array 307, is captured by imaging device 311. The image processor 310 is controlled to grab the image captured by the imaging device 311 and process this image to derive reference spot locations (based upon the centroid of the spots therein). During wavefront sensing operations, deviation of Hartmann spot location (with respect to the recorded reference spot location) is measured to derive an estimate of the phase aberration in the wavefront sampled by the corresponding lenslet. This first approach is costly because the flat wave signal source and collimating optics must be of high optical quality.

Figure 12:
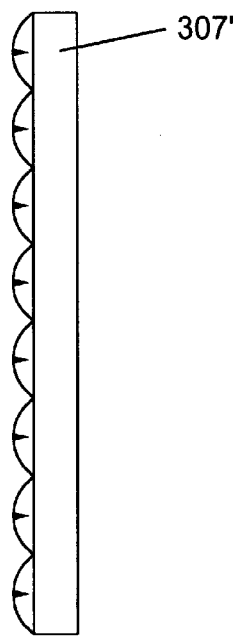
FIG. 12 is a pictorial representation of an exemplary lenslet array of the Shack-Hartmann wavefront sensor of FIG. 9, including a substantially-opaque element at the center of each lenslet of the lenslet array for use in determining the geometric reference of nominal null for the sensor.

A second approach achieves this geometric reference (without the costs of a high quality flat wave signal source and collimating optics) by providing a substantially-opaque element at the center of each lenslet of the lenslet array 307' as illustrated in FIG. 12. The lenslet array 307' is illuminated with a reference beam, which is preferably produced by reference source 315 and directed to the lenslet array 307' by beam combiner 304 and collimating lens 305 as shown in FIG. 9. Concurrently therewith, an imaging device is positioned conjugate the fiducial point image plane—this is the plane whereby the fiducial points appear at the imaging device as an array of fiducial reference spots exactly co-aligned with the centers of the lenslets. An image processor is controlled to grab the image captured by the imaging device and process this image to identify the locations of the fiducial reference spots (based upon the centroid of the fiducial reference spots). Deviation of Hartmann spot location (with respect to the recorded fiducial reference spot location) is measured during wavefront sensing operations to measure the phase aberration in the wavefront sampled by the corresponding lenslet. Advantageously, the optical components that image the reference beam onto the lenslet array 307' may be of lower optical quality and costs than the optical components required to provide the flat reference wave as discussed above. In addition, the second approach is far more stable than the first approach.

Figure 13A:
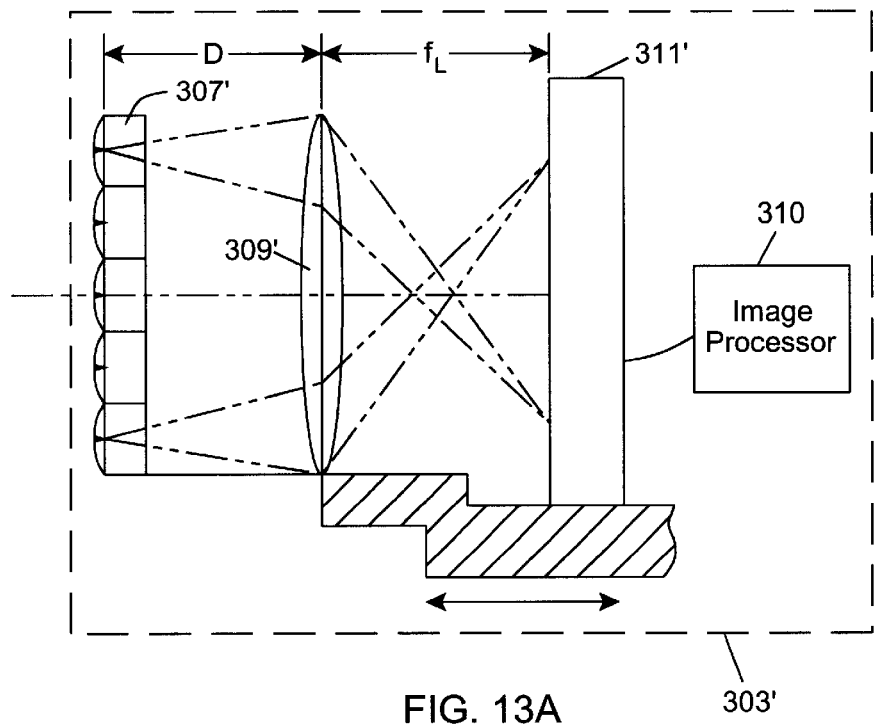
FIGS. 13A, 13B, 14A and 14B are pictorial illustrations of exemplary image forming and image capture components of the Shack-Hartmann wavefront sensor of FIG. 9, including a relay lens and the imaging device mounted on a linear actuator that has sufficient travel to allow the imaging device to image all planes from the plane substantially near the lenslet array itself, back to the focal plane of the longest focal length lenslet array.
Figure 13B:
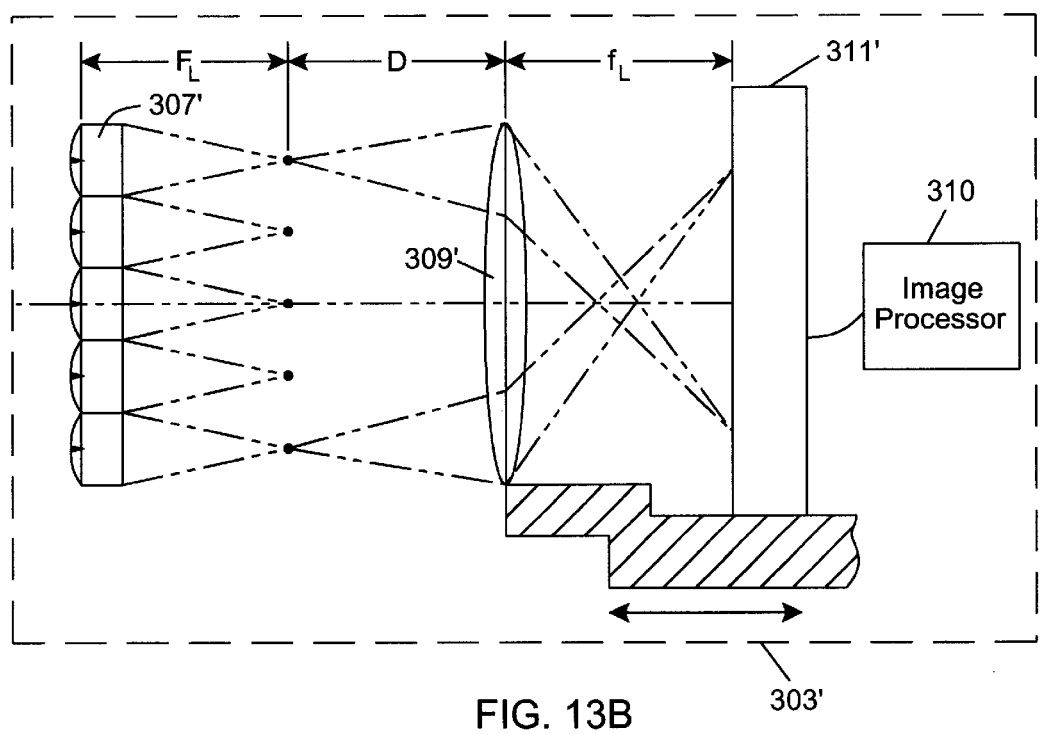

This second approach may be accomplished with the wavefront sensing head 303' of FIGS. 13A and 13B wherein relay lens 309' and the imaging device 311' are mounted on a linear actuator that has sufficient travel to allow the imaging device 311' to image all planes from the plane substantially near the lenslet array 307' itself, back to the focal plane of the longest focal length lenslet array. This configuration is described in detail in U.S. Pat. No. 5,629,765, commonly assigned to the assignee of the present invention, and herein incorporated by reference in its entirety. In this configuration, location of the fiducial reference spots in the fiducial reference spot pattern is accomplished by moving the relay lens 309' and imaging device 311' as illustrated in FIG. 13A such that the imaging device 311' is placed conjugate the fiducial point image plane. A reference beam illuminates the lenslet array 307', and the image processor 310 is controlled to grab one or more images of the fiducial point image plane as captured by the imaging device 311, and process such image(s) to identify the locations of the fiducial reference spots for each given lenslet.

The phase aberration in the distorted wavefront sampled by a given lenslet is approximated by determining the location of the Hartmann spot produced by the given lenslet relative to the location of the fiducial reference spot corresponding to the given lenslet. As illustrated in FIG. 13B, this measurement is accomplished by moving the relay lens 309' and imaging device 311' such that the imaging device 311' is placed at one or more positions substantially near the spot image plane—this is plane whereby the focal plane of the lenslet array 307' as illustrated in FIG. 11 is imaged onto the imaging device 311. The distorted wavefront is recreated at the plane of the lenslet array 307', and the image processor 310 is controlled to grab one or more images substantially near the spot image plane as captured by the imaging device 311, and process such image(s) to: (i) identify the location of the Hartmann spot corresponding to the lenslets, and (ii) compute the relative difference between this Hartmann spot location and the corresponding location of the fiducial reference spot for the lenslets.

Figure 15:
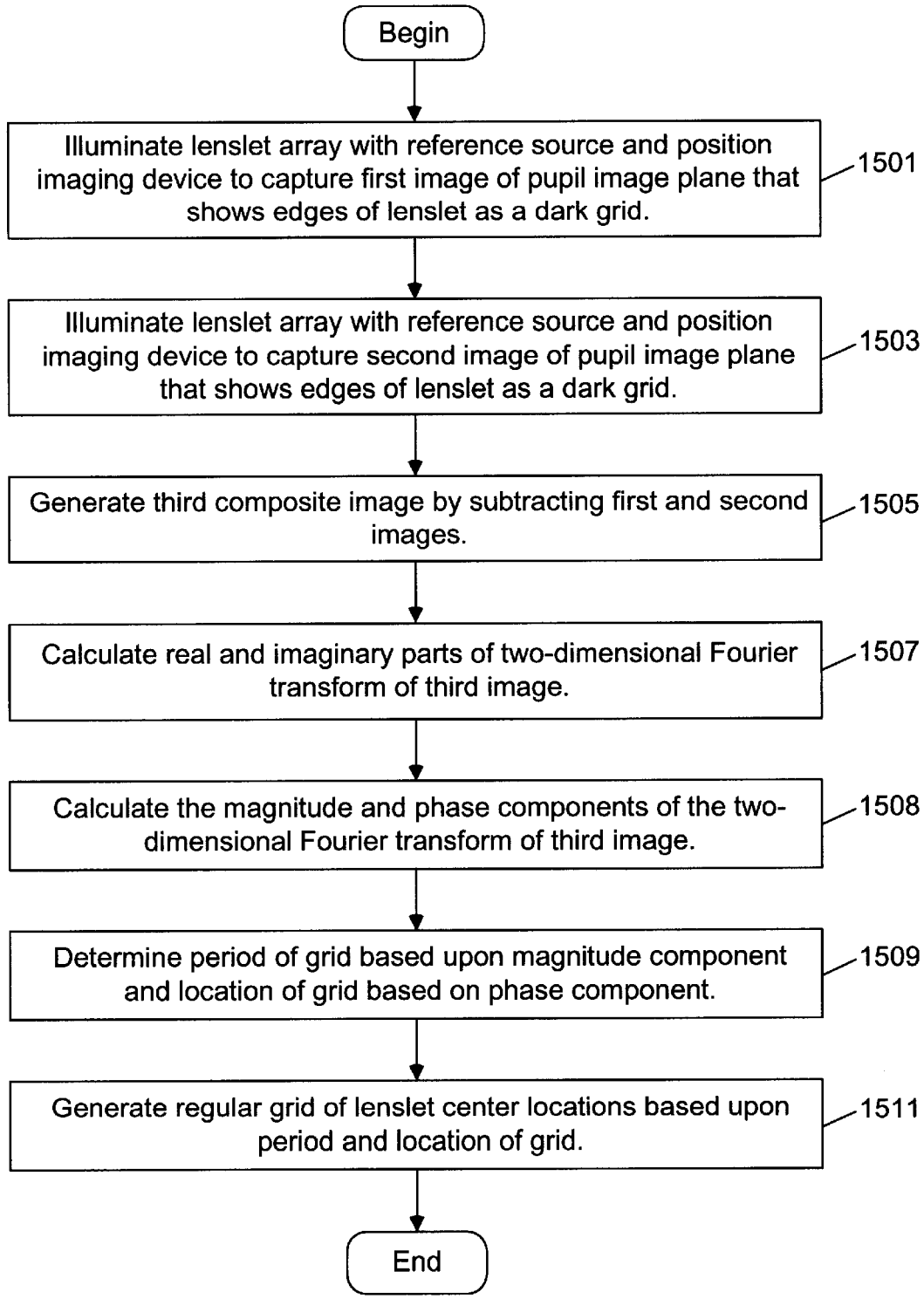
FIG. 15 is a flow chart illustrating an exemplary image processing techniques that are applied to multiple images of the pupil image plane of the Shack-Hartmann wavefront sensor of FIG. 9 to thereby derive the geometric reference of the wavefront sensor.

A third approach achieves this geometric reference (without the costs of a high quality flat wave signal source and collimating optics of the first approach and without the costs of adding fiducial points to the lenslets of the lenslet array as described above in the second approach) using sophisticated image processing techniques on multiple images of the pupil image plane. FIG. 15 is a flow chart illustrating an exemplary embodiment of such image processing techniques.

In step 1501, the lenslet array 307 is illuminated by a reference source (for example, light produced by reference source 315 may be directed to the lenslet array 307 by beam combiner 304 and collimating lens 305 as shown in FIG. 9). Preferably, the apparent distance of the reference source to the lenslet array 305 is (or is near) infinity to minimize magnification changes (due to change in distance) in the first and second images of the pupil image plane as described below. Concurrently therewith, an imaging device is positioned such that it captures a first image of pupil image plane that shows the edges of the lenslets as a dark grid, and an image processor is controlled to grab this first image captured by the imaging device.

In step 1503, the lenslet array 307 is illuminated by the reference source; and, concurrently therewith, an imaging device is positioned such that it captures a second image of pupil image plane that shows the edges of the lenslets as a bright grid, and the image processor is controlled to grab this second image captured by the imaging device.

In step 1505, the image processor generates a third composite image representing the grid (with the average signal of the first and second images removed) by subtracting the first and second images.

In step 1507, the image processor calculates the real and imaginary parts of a two-dimensional Fourier transform of the third composite image generated in step 1505. The two-dimensional Fourier transform can generally be represented as follows:

$$F(k,l) = \frac{1}{NM} * \sum_{x=0}^{N-1} \sum_{y=0}^{M-1} f(x,y) e^{-i2\Pi\left(\frac{kx}{N}+\frac{ly}{M}\right)}$$

where N represents the number of pixels in each row (i.e., x direction) of the image;

M represents the number of pixels in a column (i.e., y direction) of the image; f(x,y) represents the intensity value at a pixel (x,y) in the image; and the exponential term is the basis function corresponding to each point F(k,l) in Fourier space.

This transform can be calculated as a double sum at each image point as follows:

$$F(k,l) = \frac{1}{M} * \sum_{y=0}^{M-1} P(k,y) e^{-i2\Pi \frac{ly}{M}}$$

where $$P(k,y) = \frac{1}{N} * \sum_{x=0}^{N-1} f(x,y) e^{-i2\Pi \frac{kx}{N}}$$

The two-dimensional Fourier transform F(k,l) can be decomposed into a real part (R(k,l)) and an imaginary part (I(k,l)) as follows:

$$F(k,l) = R(k,l) + iI(k,l)$$

In step 1508, the image processor calculates the magnitude and phase components of the two-dimensional dimensional Fourier transform calculated in step 1507. The magnitude and phase components of the two-dimensional Fourier transform F(k,l) can be calculated as follows:

$$\text{Magnitude } |F(k,l)| = (R(k,l)^2 + I(k,l)^2)^{1/2}$$

$$\text{Phase } \Phi(k,l) = \arctan\left(\frac{I(k,1)}{R(k,1)}\right)$$

In step 1509, the image processor determines the period of the grid based upon the magnitude component of the two-dimensional dimensional Fourier transform calculated in step 1508, and determines the location of the grid based upon the phase component of the two-dimensional dimensional Fourier transform calculated in step 1508. This step is preferably accomplished as follows. First, a region around the expected first-harmonic peak (based upon the approximate spacing of the grid) in the magnitude component calculated in step 1508 is identified. Second, a function (such as a parabolic function) is fit to this region, and a maximum of this function is identified. Third, the period of a grid in both x and y direction that corresponds to this maximum is identified. The maximum magnitude component of the Fourier transform corresponds to a spatial frequency that is inversely proportional to the period of the grid in both x and y direction. Finally, the phase component of the Fourier transform calculated in step 1508 that corresponds to this maximum is identified, and the location of the grid is calculated based upon the identified phase component. Conceptually, the identified phase component provides translation in both x direction and y direction from the origin of the coordinate system of the image device to the origin of the grid.

Finally, in step 1511, the image processor generates a regular grid of lenslet center locations in the coordinate system of the imaging device based upon the location and period of the grid determined in step 1509. Conceptually, the lenslet center locations are offset a half cycle in both the x direction and y direction from the grid. The half cycle offset can be readily determined from period of the grid (which is inversely proportional to the maximum magnitude component of the Fourier transform).

Such lenslet center locations are analogous to the locations of spots of the reference spot pattern in the first approach and the fiducial point spot pattern in the second approach, thus providing the geometric reference to nominal null (i.e., spot location corresponding to incident of a planar wavefront on a given lenslet). Deviation of Hartmann spot location (with respect to the corresponding lenslet center location) is measured during wavefront sensing operations to measure the local tilt in the wavefront sampled by the corresponding lenslet. This approach is advantageous because it avoids the costs of a high quality flat wave signal source and collimating optics of the first approach and the costs of adding fiducial points to the lenslets of the lenslet array as described above in the second approach.

Figure 14A:
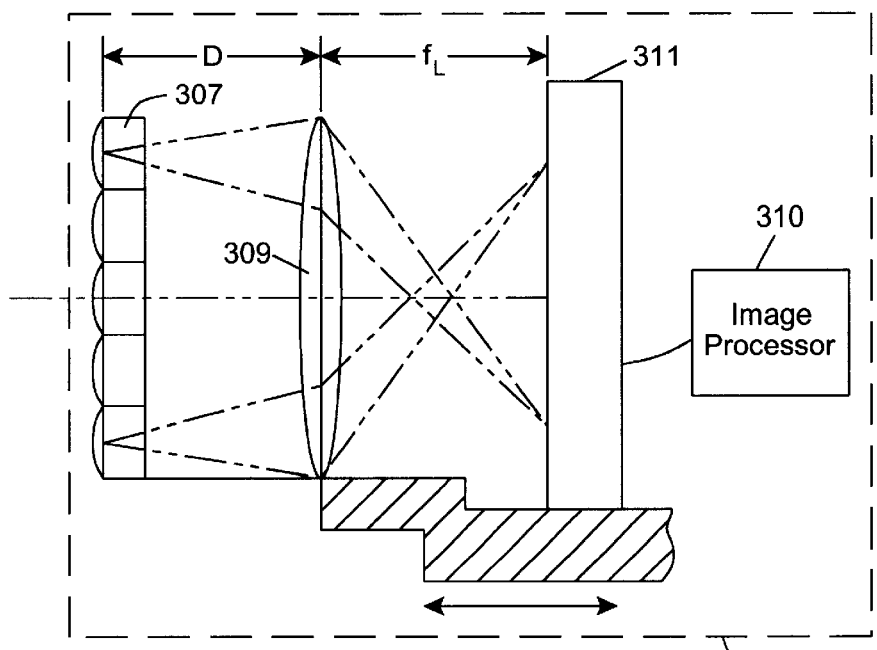
Figure 14B:
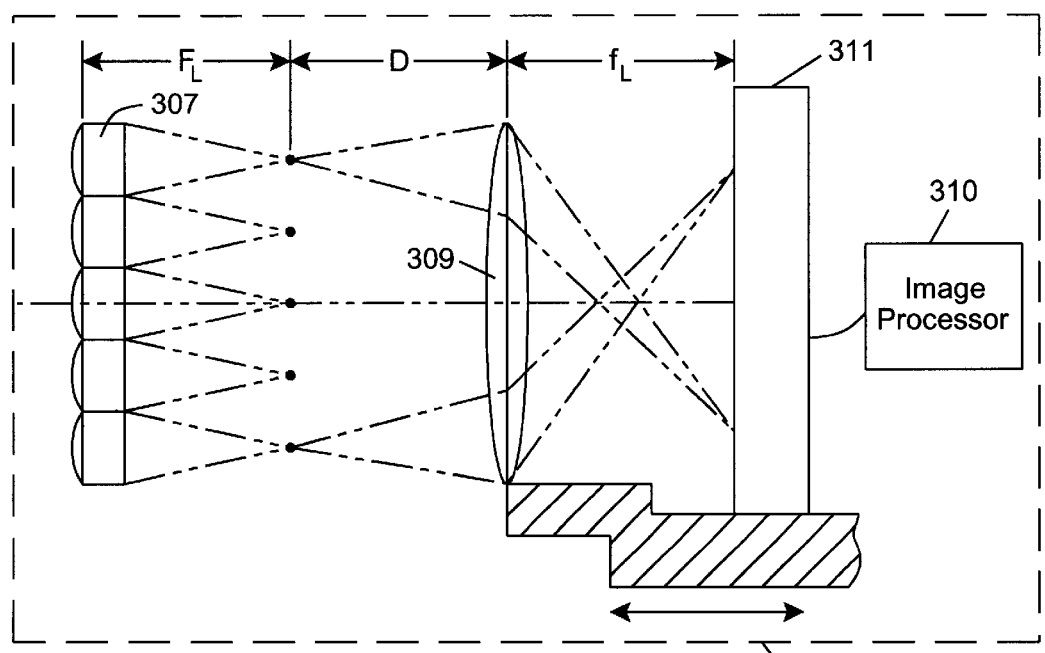

This third approach may be accomplished with the wavefront sensing head 303" of FIGS. 14A and 14B wherein the relay lens 309 and the imaging device 311 are mounted on a linear actuator, which preferably has sufficient travel to allow the imaging device 311 to image all planes from the plane substantially near the lenslet array 307 itself, back to the focal plane of the lenslet array. In this configuration, the imaging device 311 may capture the first image in step 1501 by moving the relay lens 309 and image device 311 to a position whereby the imaging device 311 captures the pupil image plane slightly outside of best focus (i.e., the plane of the lenslet array 307 and the plane of the relay lens 309 is offset by D+$\tau_1$). In addition, the imaging device 311 may capture the second image in step 1503 by moving the relay lens 309 and image device 311 to a position whereby the imaging device 311 captures the pupil image plane slightly inside of best (i.e., the plane of the lenslet array 307 and the plane of the relay lens 309 is offset by D−$\tau_2$). The image processor 310 performs the operations of steps 1505 to 1511 to generate the lenslet center locations in the coordinate system of imaging device 311.

Figure 16:
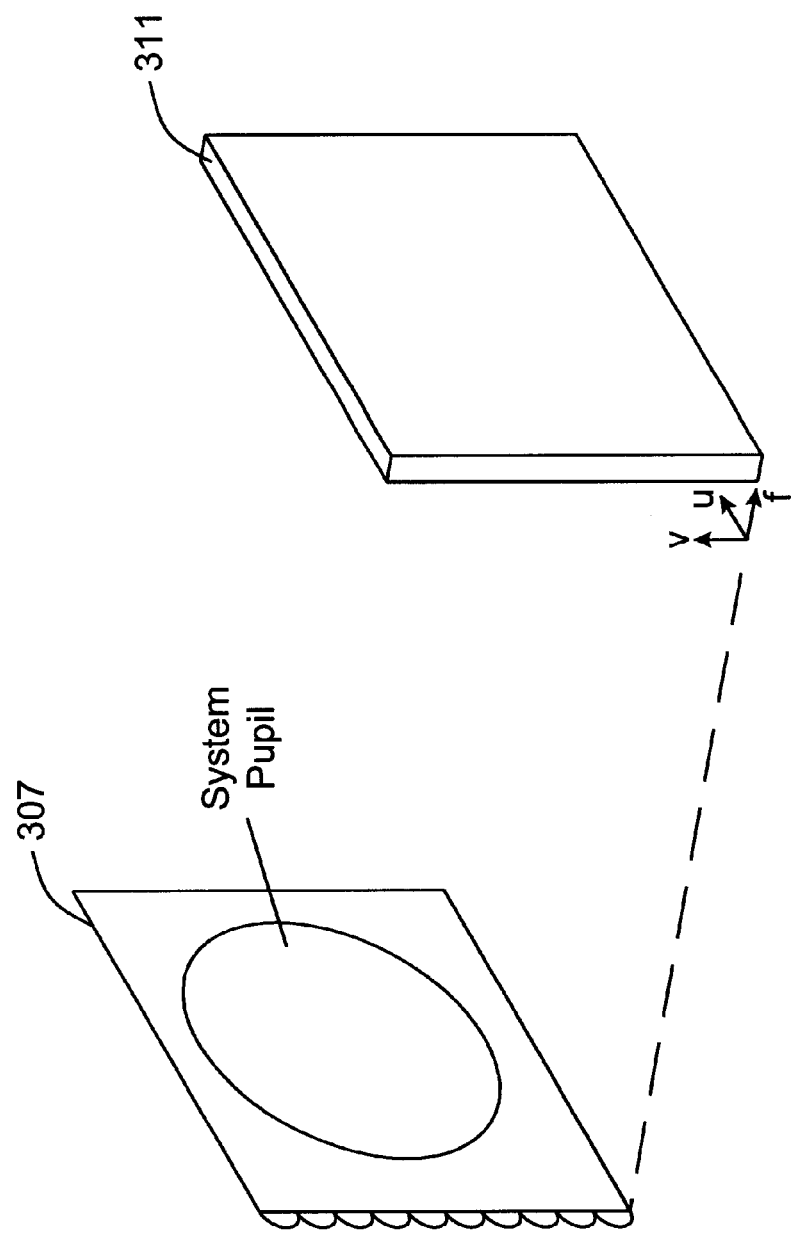
FIG. 16 is a pictorial illustration that shows the spatial position of the system pupil (the pupil of the eye under test) in an exemplary local coordinate system used by the Shack-Hartmann wavefront sensor of FIG. 9.

Position of the System Pupil (e.g. the Pupil of the Eye Under Test) in the Local Coordinate System of the Wavefront Sensing Head As described above, the wavefront measurement operations performed by the Shack-Hartmann wavefront sensor requires calibration of the position of the system pupil (e.g., the pupil of the eye under test) in the local coordinate system of the wavefront sensing head. FIG. 16 illustrates an exemplary local coordinate system for use by the wavefront sensing head of FIG. 9, which includes pixel coordinates (u,v) of the imaging device 311 and a distance f along the optical axis of the system. Such calibration may be fixed by design. However, this mapping is critical to successful estimation of the wavefront (and the operation of the closed-loop phase compensation system), and any errors therein are directly related to the absolute wavefront measurement error. Thus, it is preferable that the Shack-Hartmann wavefront sensor employ a mechanism that can dynamically (and automatically without human intervention) perform such calibration.

Figure 17:
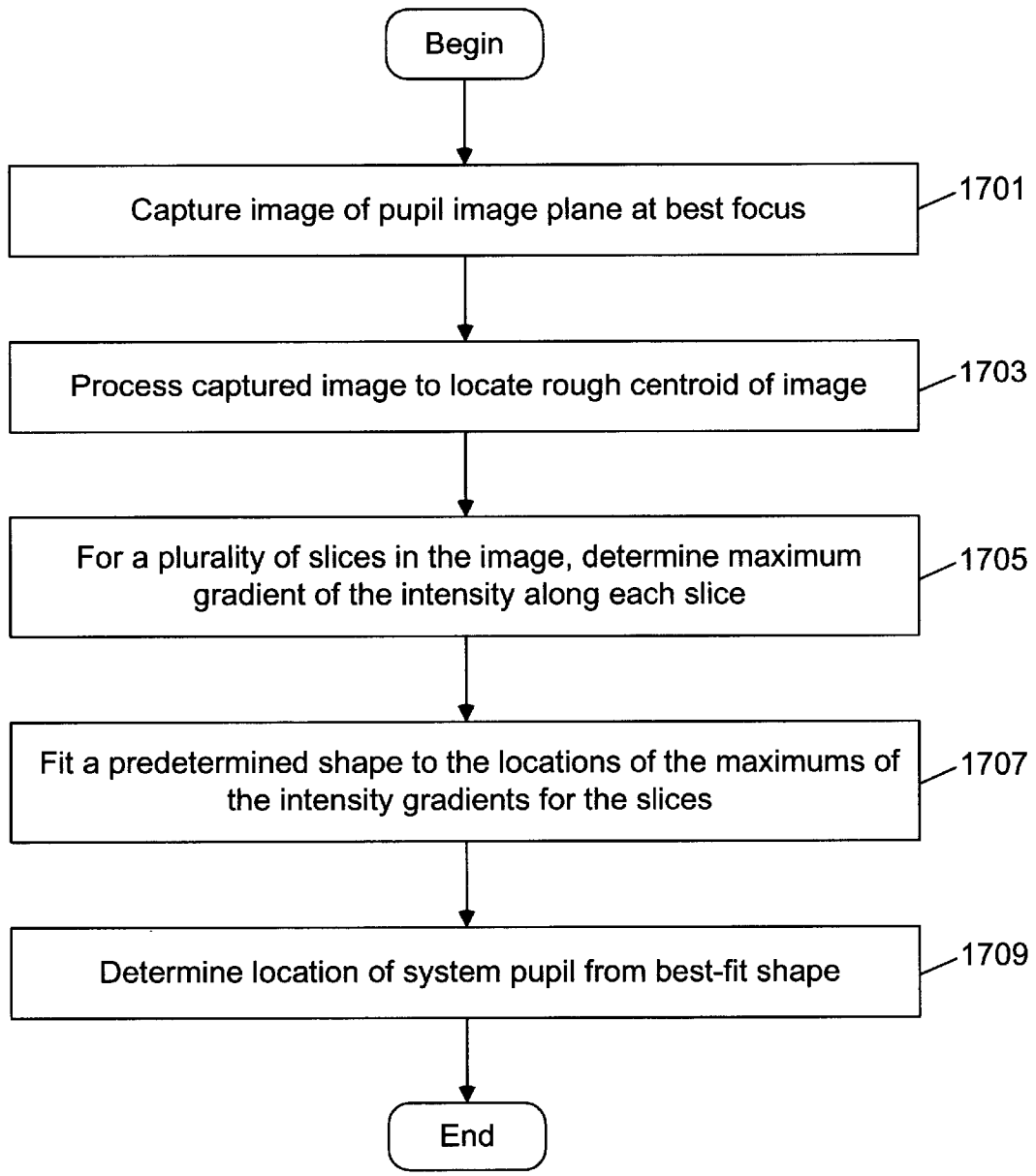
FIG. 17 is a flow chart illustrating an exemplary image processing technique that automatically locates the position of the system pupil (e.g., the pupil of the eye under test) in the local coordinate system of the Shack-Hartmann wavefront sensor of FIG. 9.

FIG. 17 is a flow chart illustrating an exemplary image processing technique that automatically locates the position of the system pupil (e.g., the pupil of the eye under test) in the local coordinate system of the wavefront sensor. This technique can be used dynamically to perform such calibration as frequently as required to ensure the opto-mechanical stability of the system.

In step 1701, the system pupil (e.g., the pupil of the eye under test) is imaged at the plane of the lenslet array 307 (for example by the optical train of the ophthalmic instrument, beam combiner 304 and collimating lens 305 of the wavefront sensor); and, concurrently therewith, an imaging device captures an image of pupil image plane at best focus.

In step 1703, an image processor processes the image of the pupil image plane grabbed in step 1701 to locate the centroid of the image. To calculate the centroid of the image in the x-direction, weights are assigned to each column of pixels in the image and the measured intensity for each pixel in the image is multiplied by the weight corresponding to the column of the given pixel and summed together. If the weights vary linearly with the distance of the column from the center of the image, this sum will be a measure of the x-position of the light distribution. The sum needs to be normalized by dividing by the sum of the unweighted intensities. To calculate the centroid of the light distribution in the y-direction, weights are assigned to each row of pixels in image and the measured intensity for each pixel in the image is multiplied by the weight corresponding to the row of the given pixel and summed together. If the weights vary linearly with the distance of the column from the center of the image, this sum will be a measure of the y-position of the light distribution. The sum needs to be normalized by dividing by the sum of the unweighted intensities. Such centroid calculation may be represented mathematically as follows:

$$x_c = \frac{\sum_i \sum_j w_j * I_{ij}}{\sum_i \sum_j I_{ij}}$$

$$y_c = \frac{\sum_i \sum_j w_i * I_{ij}}{\sum_i \sum_j I_{ij}}$$

where i and j identify the rows and columns, respectively, of the image; $w_i$ and $w_j$ are the weights assigned to given rows and columns, respectively, of the image; and $I_{ij}$ is the intensity of a given pixel in row i and column j of the image.

Figure 18:
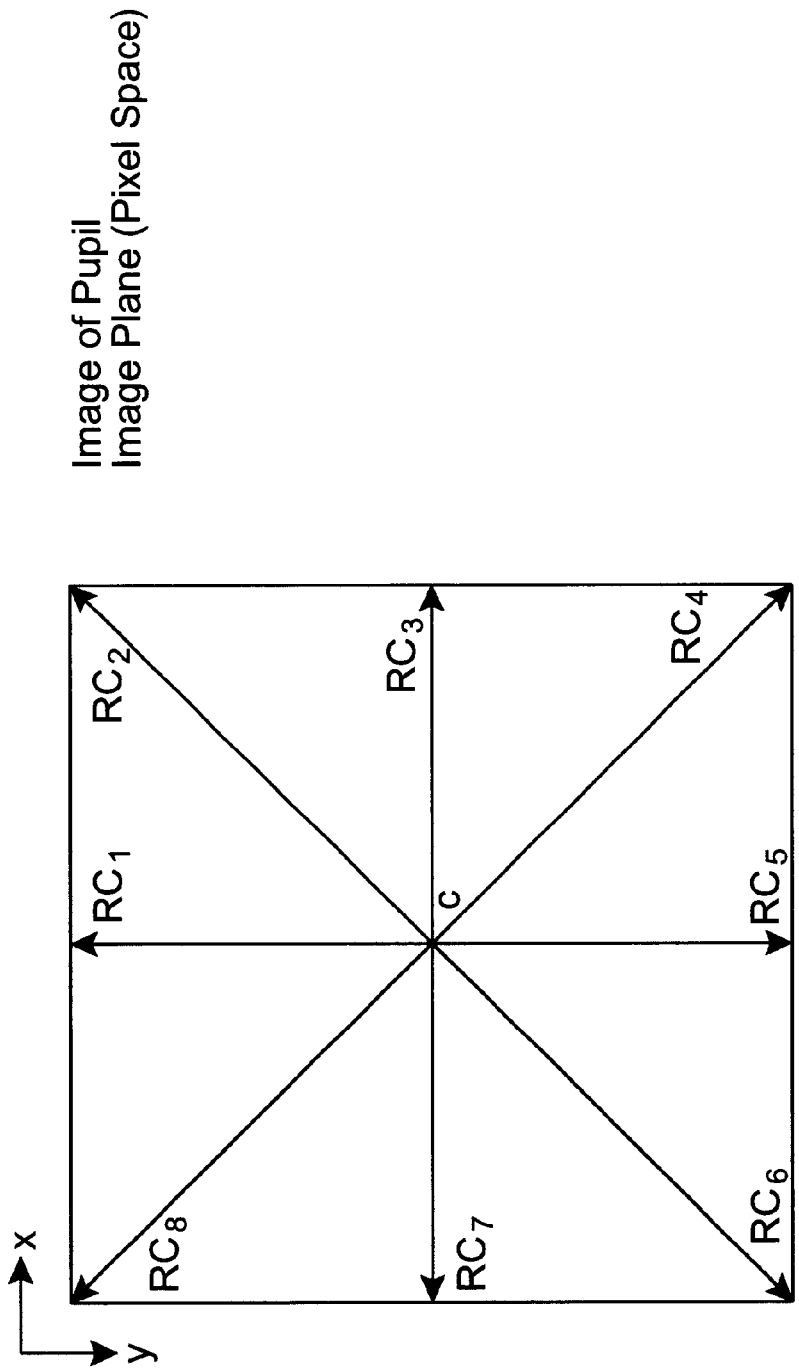
FIG. 18 is a graphical illustration of exemplary slices (RC1 . . . RC8) from a centroid C to the periphery of an image of the pupil image plane (e.g., in the u,v pixel space), which are generated in the processing of FIG. 17.

In step 1705, the image processor processes the image of the pupil image plane grabbed in step 1701 to determine, for a plurality of slices (e.g., radial cuts) from the centroid (calculated in step 1703) to the periphery of the image, the gradient of the intensity along each slice, and the pixel location of maximum of the intensity gradient along each slice. FIG. 18 provides a graphical illustration of exemplary slices (RC1 . . . RC8) from a centroid C to the periphery of an image of the pupil image plane (e.g., in the u,v pixel space).

In step 1707, the image processor fits a predetermined shape (such as a circle, ellipse or rectangle) to the pixel locations of the maximums of the intensity gradient along the slices as calculated in step 1705. This best-fit shape (e.g., pixel coordinates of the center and radius in the case of a best-fit circle) provides the location of the system pupil (e.g., the pupil of the eye under test) in the pixel coordinate system of the imaging device, form which can be derived the location of the system pupil (e.g., the pupil of the eye under test) in the local coordinate system of the wavefront sensing head. For example, for the local coordinate system illustrated in FIG. 16, such pixel coordinates and the distance along the optical path from the lenslet array 307 to the imaging device 311 provides the (u,v,f) coordinates of the system pupil (e.g., the pupil of the eye under test).

The calibration operations of FIG. 17 may be accomplished with the wavefront sensing head 303" of FIGS. 14A and 14B wherein the relay lens 309 and the imaging device 311 are mounted on a linear actuator, which preferably has sufficient travel to allow the imaging device 311 to image all planes from the plane substantially near the lenslet array 307 itself, back to the focal plane of the lenslet array. In this configuration, the imaging device 311 may capture the image of pupil image plane at best focus in step 1701 by moving the relay lens 309 and image device 311 to a position whereby the imaging device 311 captures the pupil image plane at best focus (i.e., the plane of the lenslet array 307 and the plane of the relay lens 309 is offset by D). The image processor 310 performs the operations of steps 1703 to 1707 to locate the position of the system pupil (e.g., the pupil of the eye under test) in the local coordinate system of the wavefront sensing head.

Dynamic Identification of Sub-Arrays (Pixel Areas) of the Imaging Device that Avoid Dot-Crossover In addition, it is preferable that the Shack-Hartmann wavefront sensor employ a mechanism that addresses dot crossover problem, which occurs when there is a predefined region of the Hartmann spot imaging plane that is used to determine location of the Hartmann spot for a given lenslet. If the spot moved outside that predefined region (i.e., dot crossover occurs), the dynamic range of the sensor is exceeded, resulting in an erroneous wavefront measurement.

In order to address the dot crossover problem, the Shack-Hartmann wavefront sensor can employ a mechanism that dynamically identifies the sub-arrays (pixel areas) of the Hartmann spot imaging device (e.g., the imaging device that will be used for the determination of Hartmann spot positions) that avoids dot crossover for a particular wavefront measurement. A detailed description of an illustrative procedure that provides such a dynamic mechanism is described below with respect to FIG. 19.

In step 1901, the system pupil image is recreated at the lenslet array 307 and the Hartmann spot imaging device is positioned such that it captures an image of the Hartmann spot pattern (at best spot focus) as formed at the focal plane of the lenslet array; and the sub-regions (i.e., pixel areas) of the imaging device 311, which are denoted "test subapertures" for the sake of description, that are to be used for the determination of Hartmann spot locations are defined. In this step, the system preferably grabs an image of the Hartmann spot pattern and locates the position of all of the "useable" Hartmann spots in this image. Preferably, a predetermined criterion (for example, based upon intensity values of pixels covered by a given Hartmann spot) is used to distinguish between "useable" and "unuseable" Hartmann spots and to filter out such "unuseable" Hartman spots. Sub-regions of the imaging device 311 around each useable Hartmann spot are defined and stored in a list of test subapertures. The sizes of these sub-regions are made as large as possible without overlapping. In addition, the system determines if a reasonable number of "useable" Hartmann spots have been found based upon the known spacing of the lenslet array 307 and the size of the Hartmann spot imaging device. If an unreasonably low number of "useable" Hartmann spots have been found, preferably an error is reported to the user.

In step 1903, each test subaperture in the list of test subapertures is matched to a corresponding lenslet (i.e., the particular lenslet that produced the spot from which the subaperture is derived). This matching process preferably is accomplished by capturing, grabbing and processing one or more additional images of the Hartmann spot pattern that are taken slightly inside (or outside) best focus. In such image (s), the location of the spot in each subaperture differs from that found in the image at best spot focus. This difference is due to any deviation of the direction of propagation from the optical axis of the lenslet. The positions measured in the images may be used to project a ray from a given spot back to the plane of the lenslet array 307 (i.e., the ray passing through the spot positions as illustrated in FIG. 19B) to generate a list of crossing locations at this plane for each test subaperture.

It is important to realize that the test subapertures (defined in step 1901) are wholly separate from the sub-regions of the imaging device that will be used for the measurement of the reference source (which are defined in step 1905). It is this use of separate lists of subapertures and subsequent matching process (step 1909) that allows the wave front sensor 303 to effectively resolve potential dot crossover problems and thus achieve very large dynamic range that includes highly aberrated eyes.

In step 1905, a reference source illuminates the lenslet array 307 and the Hartmann spot imaging device is positioned such that it captures an image of the spot pattern (at best spot focus) formed at the focal plane of the lenslet array; and the sub-regions (i.e., pixel areas) of the imaging device, which are denoted "reference subapertures" for the sake of description, that are to be used for the determination of such spot locations are defined. The reference source may be directed to the lenslet array 307 by beam combiner 304 and collimating lens 305 as shown in FIG. 9. In this step, the system preferably grabs an image of the spot pattern and locates the position of all of the "useable" spots in this image. Preferably, a predetermined criterion (for example, based upon intensity values of pixels covered by a given spot) is used to distinguish between "useable" and "unuseable" spots and to filter out such "unuseable" spots. Sub-regions of the imaging device around each useable spot are defined and stored in a list of reference subapertures. The sizes of these sub-regions are made as large as possible without overlapping. In addition, the system determines if a reasonable number of "useable" spots have been found based upon the known spacing of the lenslet array 307 and the size of the imaging device. If an unreasonably low number of "useable" spots have been found, preferably an error is reported to the user.

In step 1907, each reference subaperture in the list of reference subapertures is matched to a corresponding lenslet (i.e., the particular lenslet that produced the spot from which the subaperture is derived). This matching process preferably is accomplished by capturing, grabbing and processing one or more additional images of this spot pattern that are taken slightly inside (or outside) best focus. In such image (s), the location of the spot in each subaperture differs from that found in the image at best spot focus. This difference is due to any deviation of the direction of propagation from the optical axis of the lenslet. The positions measured in the images may be used to project a ray from a given spot back to the plane of the lenslet array 307 (i.e., the ray passing through the spot positions as illustrated in FIG. 19B) to generate a list of crossing locations at this plane for each reference subaperture.

In step 1909, the system then processes the lists of crossing locations and the associated aperture lists to find unique reference aperture/test aperture pairs whose crossing points coincide within prescribed tolerances to a lenslet center of the lenslet array (which may be derived from the reference spot locations as described above, or from the fiducial point locations as described above with respect to FIGS. 12, 13A, 13B, and 14, or from the image processing techniques described above with respect to FIGS. 15 and 16). The system then verifies that the crossing points for these unique reference aperture/test aperture pairs correspond to a single lenslet in the lenslet array. In the event that the crossing points for a particular reference aperture/test aperture pair correspond to different lenslets in the lenslet array, that particular reference aperture/test aperture pair is removed from the list. The ultimate result of the matching process of step 1909 is a list of lenslets (or reference spot locations or fiducial point locations or lenslet centers) each uniquely associated with a given reference subaperture and test subaperture.

The list of lenslets (or lenslet reference spot locations or lenslet fiducial point locations or lenslet centers) produced by the matching process of step 1909 is used during wavefront sensing operations to provide the geometric reference of nominal null (i.e., reference spot position) for the corresponding subapertures. In addition, the subapertures of the Hartmann spot image imaging device that are used during such wavefront sensing operations is limited to the subapertures corresponding to the lenslets (or lenslet reference spot locations or lenslet fiducial point locations or lenslet centers) produced by the matching process of step 1909, thereby effectively resolving the dot cross over problem.

It is important to realize that the reference subapertures (defined in step 1901 are wholly separate from the test subapertures (defined in step 1905). It is this use of separate lists of subapertures and the subsequent matching process (steps 1903,1907 and 1909) that allows the wavefront sensor to effectively resolve potential dot crossover problems and thus achieve very large dynamic range that includes the wavefront sensing of highly aberrated eyes. Moreover, this process may be repeated during measurement to verify calibration (or possibly recalibrate) of the wavefront sensor.

Figure 19A:
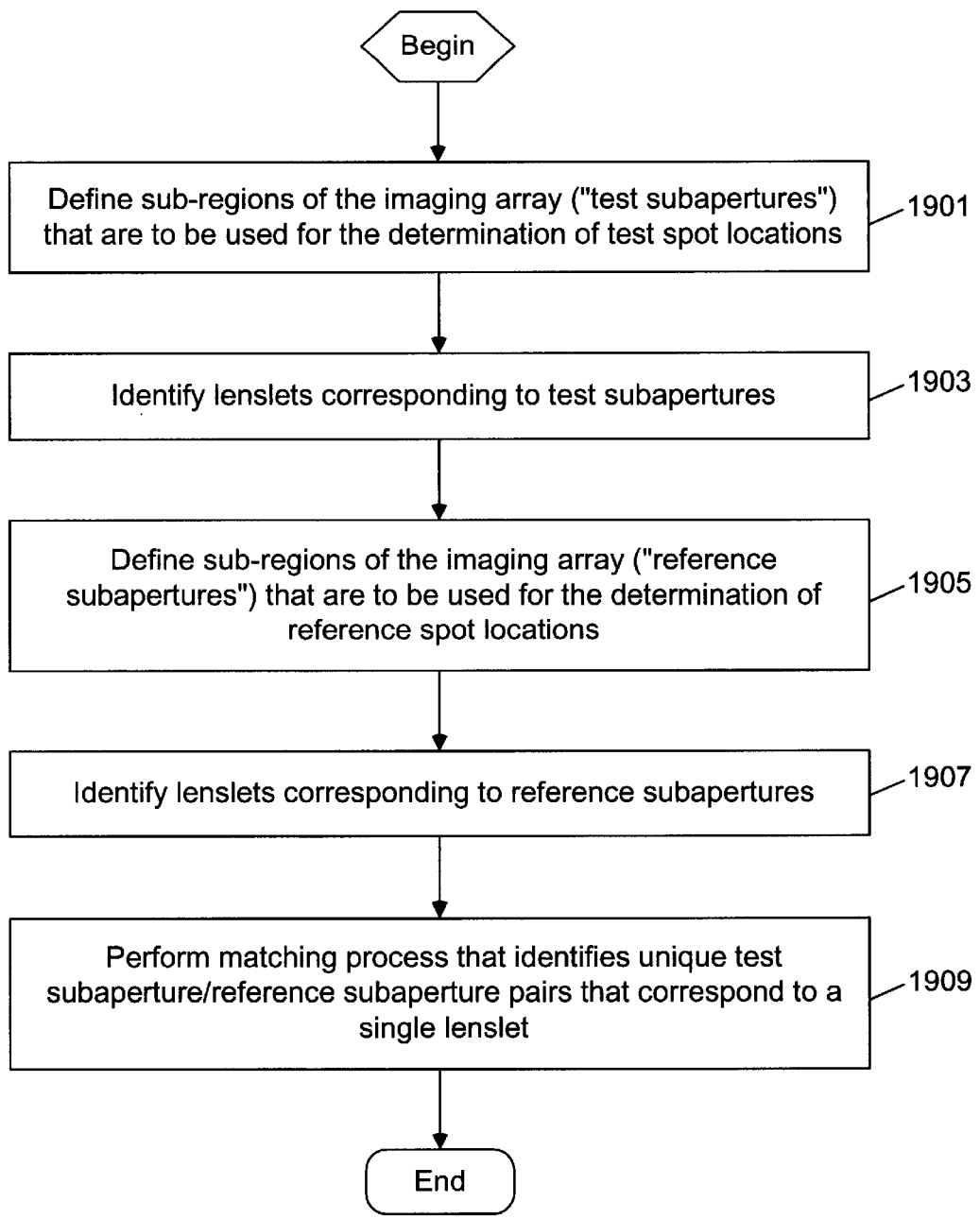
FIG. 19A is a flow chart that illustrates a mechanism, which is preferably employed by the Shack-Hartmann wavefront sensor of FIG. 9, that dynamically identifies the sub-arrays (pixel areas) of the Hartmann spot imaging device (e.g., the imaging device that will be used for the determination of Hartmann spot positions) that avoids dot crossover for a particular wavefront measurement.
Figure 19B:
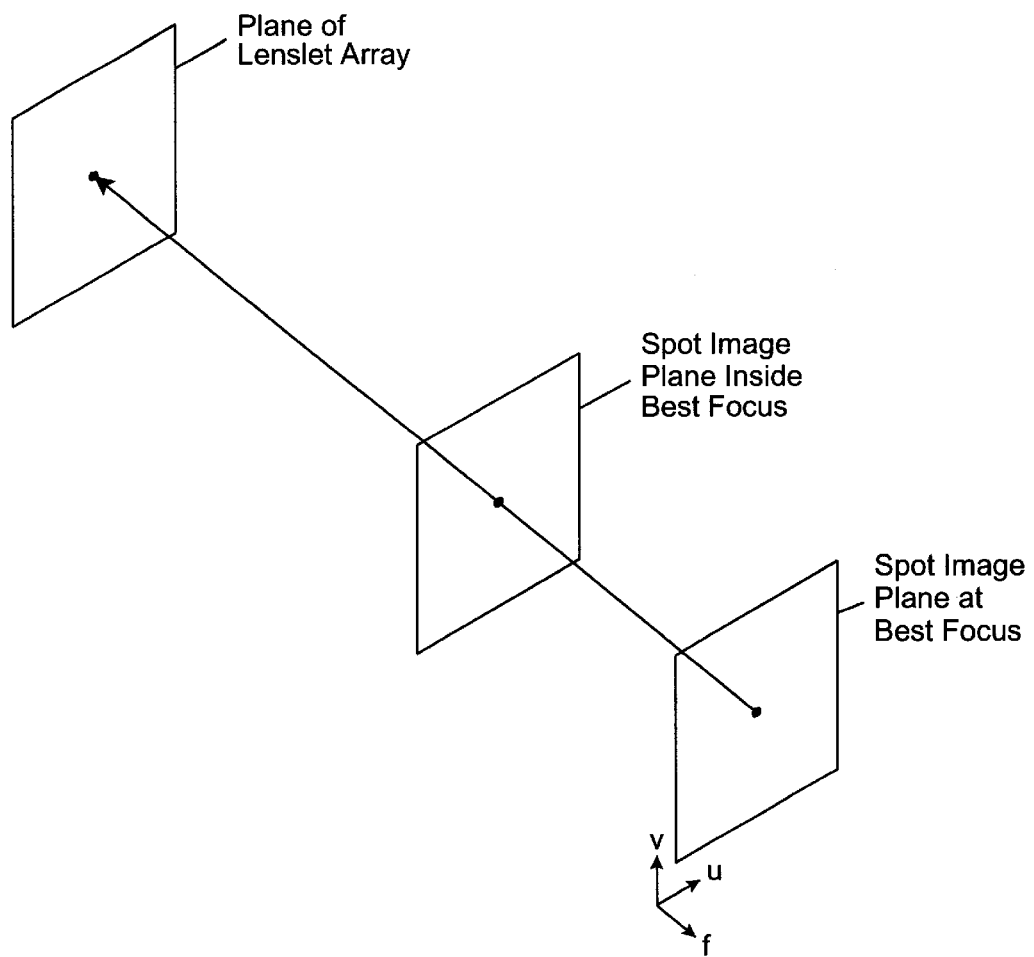
FIG. 19B is a pictorial illustration of the projection of a ray from a given Hartmann spot in the spot image plane to the plane of the lenslet array of the Shack-Hartmann wavefront sensor of FIG. 9, which is used in the processing of FIG. 19A.

The operations of FIG. 19 require the capture of multiple images of different planes between the lenslet array itself and the focal plane of the lenslet array. Such operations may be accomplished with the wavefront sensing head 303" of FIGS. 14A and 14B (or similarly with the wavefront sensing head 303' of FIGS. 13A and 13B) wherein the relay lens 309 and the imaging device 311 are mounted on a linear actuator, which preferably has sufficient travel to allow the imaging device 311 to image all planes from the plane substantially near the lenslet array 307 itself, back to the focal plane of the lenslet array. In this configuration, the imaging device 311 captures the images of the test spot pattern/reference spot pattern at best focus in steps 1901/1905 by moving the relay lens 309 and image device 311 to a position whereby the imaging device 311 captures the spot image plane at best focus (i.e., the plane of the lenslet array 307 and the plane of the relay lens 309 is offset by $D+f_L$). And, the imaging device 311 captures the images of the test spot pattern/reference spot pattern slightly inside (or outside best focus) in steps 1903/1907 by moving the relay lens 309 and image device 311 to a position whereby the imaging device 311 captures the spot image plane slightly inside (or outside) best focus (i.e., the plane of the lenslet array 307 and the plane of the relay lens 309 is offset by $D+f_L \pm \tau$).

Note that the configuration of wavefront sensing head 303" of FIGS. 14A and 14B (and similarly the configuration of the wavefront sensing head 303' of FIGS. 13A and 13B) achieve the capture of multiple images required for full wavefront measurement by moving a single imaging device. Such configurations lead to unavoidable delay between such captures. This delay may be problematic in some ophthalmic applications. More specifically, unless the human eye is immobilized, it is constantly moving, both voluntarily and involuntarily. While such motion can be frozen by using a short exposure time to capture the Hartmann spots, when the pupil of the eye moves from exposure to exposure, it becomes difficult to correctly associate the local tilt measures made by the wavefront sensor with the proper location on the pupil of the eye. The situation is further complicated by the fact that the pupil size is also changing as the eye adjusts to light level or other stimuli. These effects can be significant if there is a long delay between exposures (which leads to significant eye movement) and result in unacceptable wavefront measurement errors.

In addition, unless the accommodation of the human eye is paralyzed using drugs (such as Cycloplegics), the eye is capable of accommodation. During wavefront sensing, such accommodation may lead to measurement errors and misdiagnosis. Accomodation is typically controlled by directing the patient to focus on an internal fixation target, whose working distance is set to infinity to limit such accommodation. However, when measuring the aberrations of the eyes of children at an early age (for example, early age screening for vision impairments, such as ambiopia that are more easily correctable at such early ages), controlling accommodation at such an early age is very difficult because the child cannot understand the directions of the operator to focus on the internal fixation target. In such circumstances, drugs that paralyze accommodation (commonly called Cycloplegics) are typically used to measure the aberrations of the eye. Such drugs typically require a long time to take effect (30–60 minutes). In the event that the required time period for inducement of paralysis is not satisfied, prior art ophthalmic instruments are error prone in measuring the aberration of the eye and thus susceptible to misdiagnosis. In addition, such drugs typically require a long wear off (up to 24 hours), which leads to patient discomfort over this prolonged period.

Real-Time Hartmann Wavefront Sensing

In another aspect of the present invention, improved Hartmann wavefront sensors (and ophthalmic instruments employing the same) have been developed that address the challenges presented by eye movement and/or accommodation.

Figure 20A:
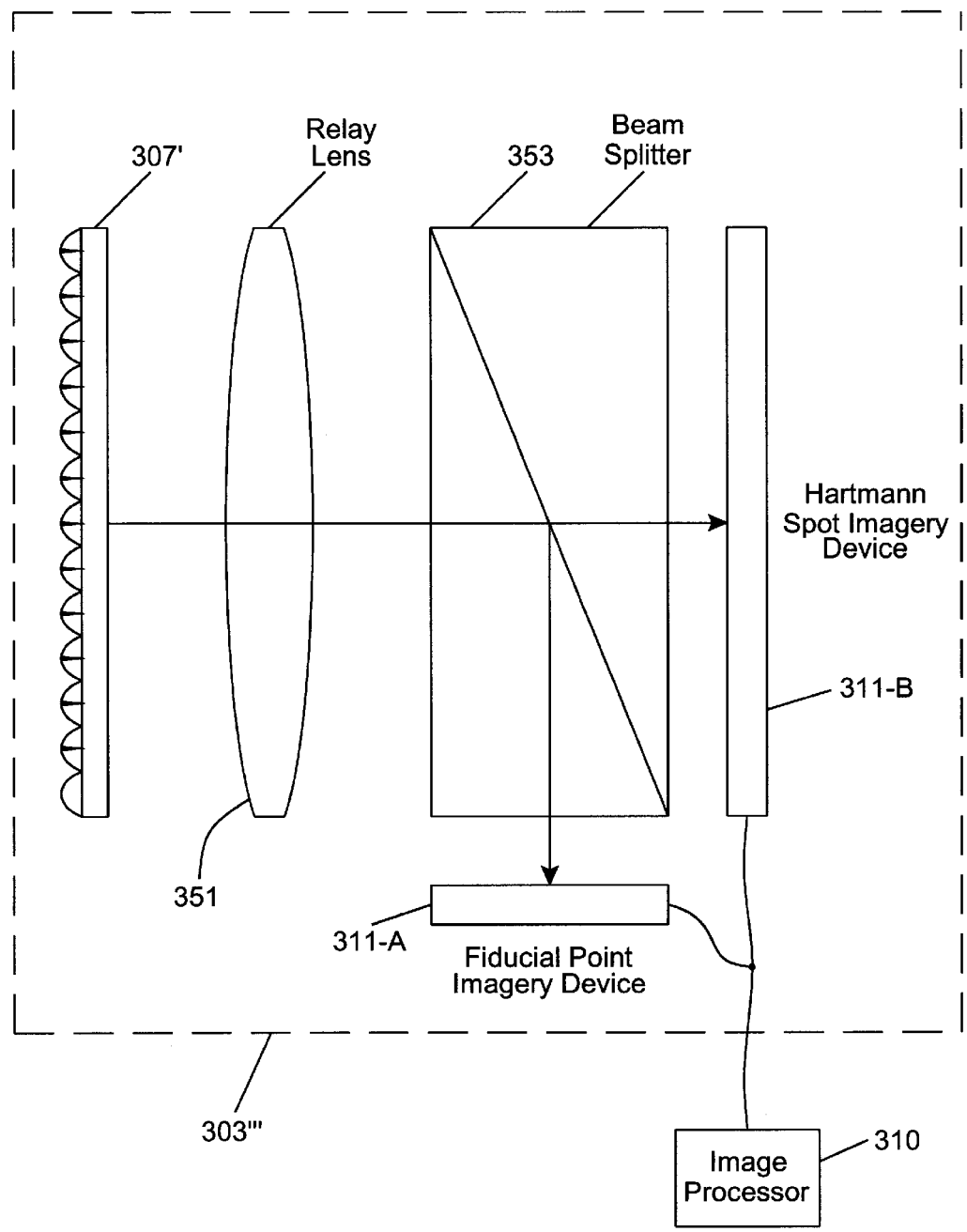
FIG. 20A illustrates an improved Shack-Hartmann wavefront sensing head of an ophthalmic instrument according to the present invention, wherein fiducial points of the lenslet array are used to provide the geometric reference of nominal null and the delays associated with capture of the required multiple images are avoided. The improved Shack-Hartmann wavefront sensing head includes a relay lens, beam splitter and multiple imaging devices that cooperate to capture images of the fiducial point image plane and the Hartmann spot imaging plane in real time in order to minimize the adverse effects of eye movement and/or accommodation on wavefront measurements performed therein.

FIG. 20A illustrates an improved Shack-Hartmann wavefront sensing head 303''' that utilizes fiducial points of the lenslet array to provide a geometric reference of nominal null and avoids delays associated with capture of the required multiple images. The improved wavefront sensing head 303''' includes a relay lens 351, beam splitter 353 and multiple imaging devices that cooperate to capture images of the fiducial point image plane and the Hartmann spot imaging plane. In this configuration, the beam splitter 353 splits the light beams produced by the lenslet array 307' into multiple arms (preferably of equal intensity) which are projected onto the multiple imaging devices. For example, as shown, beam splitter 353 splits the light beams produced by the lenslet array 307' into two arms (preferably of equal intensity) which are projected onto imaging devices 311-A and 311-B. The beam splitter 353 may comprise one or more beam splitting elements, such as a cube-type beam splitter, plate-type beam splitter, or dichroic prism assembly such as those readily available from: Richter Enterprises of Livingston, Tex., described in detail at http:// www.techexpo.com/WWW/richter/; DuncanTech of Auburn, Calif., described in detail at http://www.duncantech.com/; and Edmud Optics of Barrington, N.J., described in detail at http://www.edmundoptics.com/. In the illustrative embodiment of FIG. 20A, imaging device 311-A is positioned at the fiducial point image plane and is used to capture the array of fiducial reference spots. A reference beam illuminates the lenslet array 307', and image processor 310 is controlled to grab one or more images of the fiducial point image plane as captured by the imaging device 311-A, and process such image(s) to identify the locations of the fiducial reference spots for each given lenslet. In addition, at least one other imaging device 311-B is placed at a position substantially near the Hartmann spot image plane and is used to capture images of the Hartmann spot pattern. During wavefront sensing operations, the distorted wavefront is recreated at the plane of the lenslet array 307', and the image processor 310 is controlled to grab one or more images substantially near the spot image plane as captured by the imaging device 311-B, and process such image(s) to: (i) identify the location of the Hartmann spot corresponding to the lenslets, and (ii) compute the relative difference between this Hartmann spot location and the corresponding location of the fiducial reference spot for the lenslets.

Preferably, the illumination of the reference beam and subsequent image grabbing and processing operations that derive the locations of the fiducial reference spots for each given lenslet are performed as a calibration operation prior to wavefront sensing measurements for an eye. Moreover, such operations can be used dynamically (in a manner concurrent with or interposed with such wavefront sensing measurements) to perform such calibration as frequently as required to ensure the accuracy of the system. Such dynamic operations (which may be concurrent with or interposed with wavefront sensing measurements) enable accurate real-time wavefront measurement while the eye moves and/or accommodates.

Figure 20B:
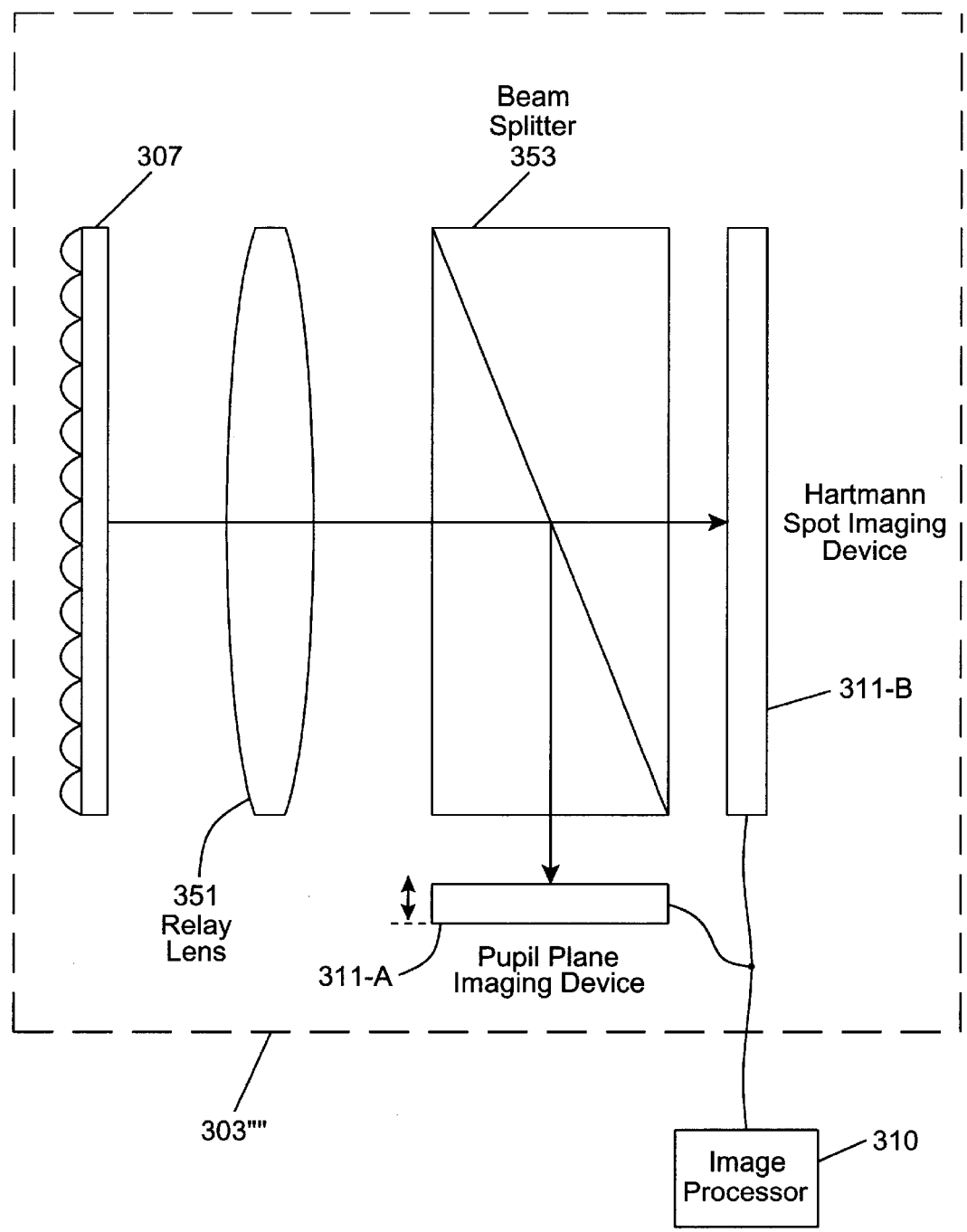
FIG. 20B illustrates an improved Shack-Hartmann wavefront sensing head of an ophthalmic instrument according to the present invention, wherein the image processing techniques on multiple images of the pupil image plane are used to derive the geometric reference to nominal null (as described above with respect to FIG. 15) and the delays associated with capture of the required multiple images are avoided. The improved Shack-Hartmann wavefront sensing head includes a relay lens, beam splitter and multiple imaging devices that cooperate to capture images of the pupil image plane and the Hartmann spot imaging plane in real time in order to minimize the adverse effects of eye movement and/or accommodation on wavefront measurements performed therein.

FIG. 20B illustrates an improved Shack-Hartmann wavefront sensing head 303'" that utilizes the image processing techniques on multiple images of the pupil image plane to derive the geometric reference to nominal null (as described above with respect to FIG. 15) and avoid delays associated with the capture of the required multiple images. The improved wavefront sensing head 303'" includes a relay lens 351, beam splitter 353 and multiple imaging devices that cooperate to capture images of the pupil image plane and the Hartmann spot imaging plane. In this configuration, the beam splitter 353 splits the light beams produced by the lenslet array 307 into multiple arms (preferably of equal intensity) which are projected onto the multiple imaging devices. For example, as shown, beam splitter 353 splits the light beams produced by the lenslet array 307 into two arms (preferably of equal intensity) which are projected onto imaging devices 311-A and 311-B. Hereto, the beam splitter 353 may comprise one or more beam splitting elements, such as a cube-type beam splitter, plate-type beam splitter, or dichroic prism assembly as described above.

In the illustrative embodiment of FIG. 20B, imaging device 311-A is positioned substantially near the pupil image plane and is mounted on a linear actuator that enables the image device 311-A to capture the first and second images in steps 1501 and 1503, respectively. A reference beam illuminates the lenslet array 307, and image processor 310 is controlled to grab the first and second images captured by the imaging device 311-A, and process such image(s) as described above in steps 1505–1511 to identify the lenslet center locations in the local coordinate system of the imaging device 311-A. In addition, at least one other imaging device 311-B is placed at a position substantially near the Hartmann spot image plane and is used to capture images of the Hartmann spot pattern. During wavefront sensing operations, the distorted wavefront is recreated at the plane of the lenslet array 307, and the image processor 310 is controlled to grab one or more images substantially near the spot image plane as captured by the imaging device 311-B, and process such image(s) to: (i) identify the location of the Hartmann spot corresponding to the lenslets, and (ii) compute the relative difference between this Hartmann spot location and the corresponding location of the lenslet center locations.

In an alternative embodiment of the wavefront sensor head of FIG. 20B, multiple image devices may be used to capture the image of the pupil image plane inside of best focus and outside of best focus, respectively, thereby capturing the first and second images of the pupil image plane of steps 1501 and 1503, respectively. In this configuration, beam splitter 353 splits the light beams produced by the lenslet array 307 into at least three arms which are projected onto the multiple imaging devices (e.g., first pupil plane imaging device, second pupil plane imaging device, and Hartmann spot imaging device). Hereto, the beam splitter 353 may comprise one or more beam splitting elements, such as a cube-type beam splitter, plate-type beam splitter, or dichroic prism assembly as described above.

Preferably, the illumination of the reference beam and subsequent image grabbing and processing operations that derive the locations of the lenslet center location for each given lenslet are performed as a calibration operation prior to wavefront sensing measurements for an eye. Moreover, such operations can be used dynamically (in a manner concurrent with or interposed with such wavefront sensing measurements) to perform such calibration as frequently as required to ensure the accuracy of the system. Such dynamic operations (which may be concurrent with or interposed with wavefront sensing measurements) enable accurate real-time wavefront measurement while the eye moves and/or accommodates.

In addition, the calibration operations of FIG. 17 may be accomplished with the wavefront sensing head 303'" of FIG. 20B in a manner that avoids the delays associated with capture of the required multiple images. In this configuration, the imaging device 311-A is positioned substantially near the pupil image plane to enable the image device 311-A to capture the image of the pupil image plane at best focus in step 1701.

Figure 20C:
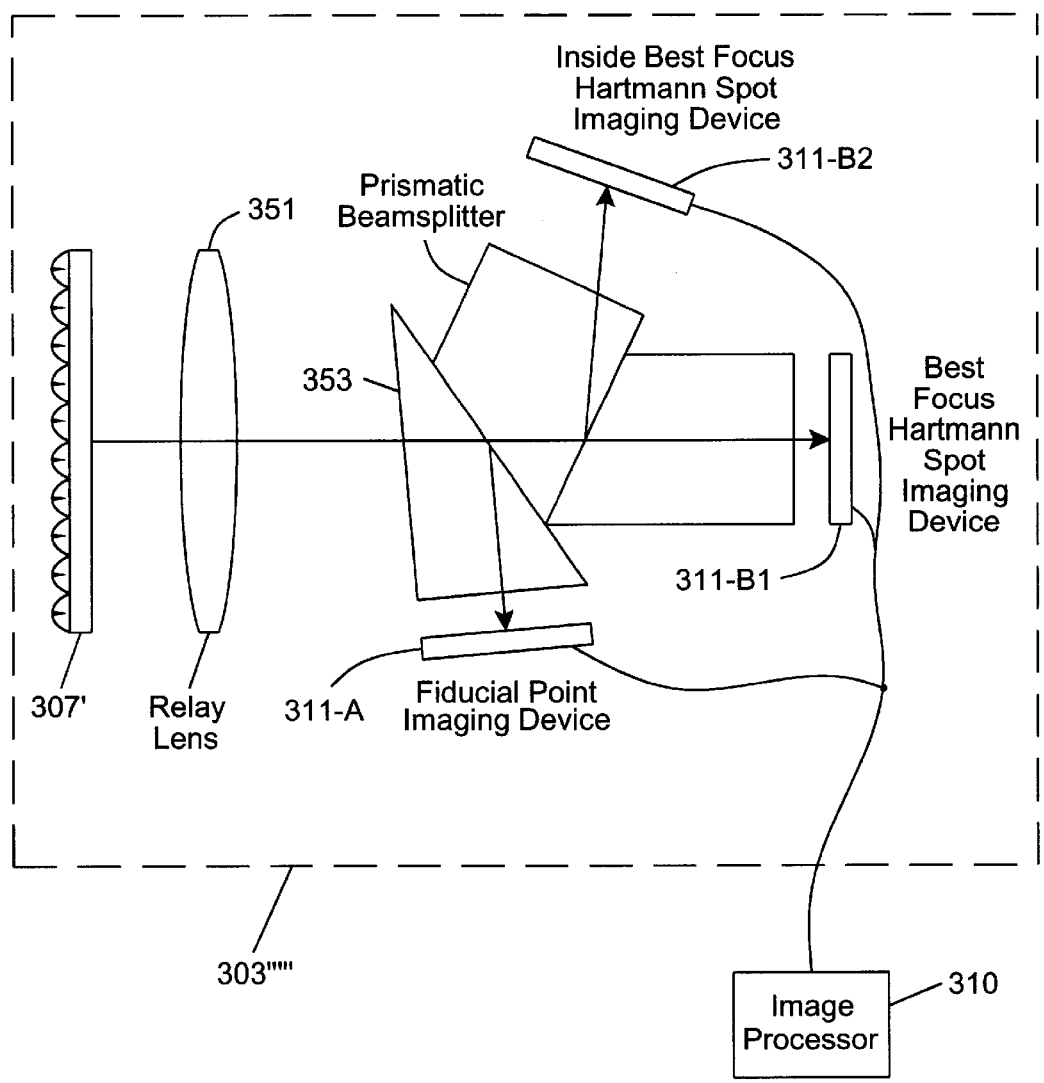
FIGS. 20C and 20D illustrate improved Shack-Hartmann wavefront sensing heads of ophthalmic instruments according to the present invention, wherein the operations of FIG. 19 are used to dynamically identify the sub-arrays (pixel areas) of the Hartmann spot imaging device (e.g., the imaging device that will be used for the determination of Hartmann spot positions) that dot crossover for a particular wavefront measurement, and the delays associated with the capture of the required multiple images are avoided. The improved wavefront sensing heads include a beam splitter and multiple imaging devices that cooperate to capture multiple images of different planes between the lenslet array itself and the focal plane of the lenslet array as required by the operations of FIG. 19 in real time in order to minimize the adverse effects of eye movement and/or accommodation on wavefront measurements performed therein.
Figure 20D:
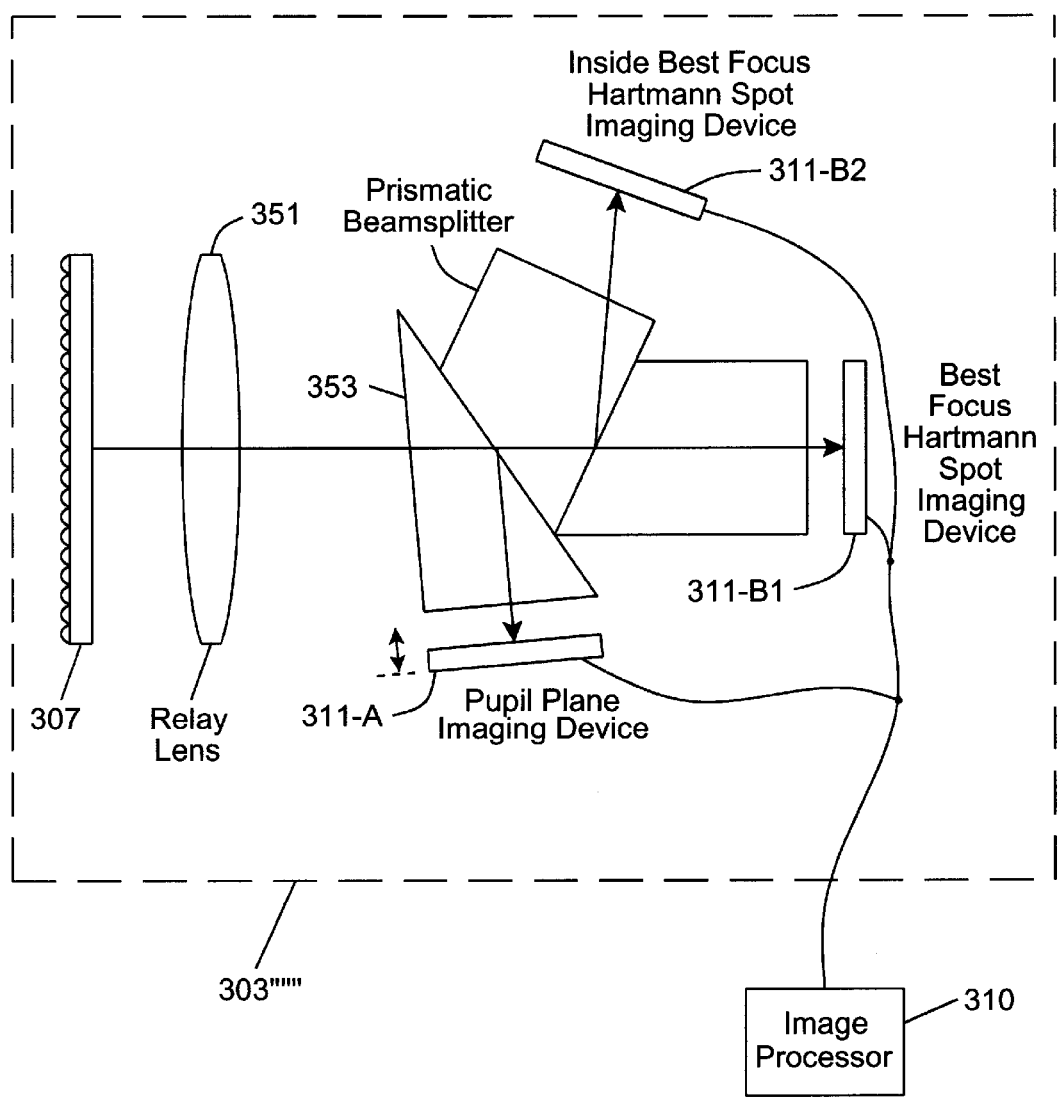

FIGS. 20C and 20D illustrate improved Shack-Hartmann wavefront sensing heads that embody the operations of FIG. 19 in dynamically identifying sub-arrays (pixel areas) of the Hartmann spot imaging device (e.g., the imaging device that will be used for the determination of Hartmann spot positions) that avoid dot crossover for a particular wavefront measurement, while avoiding delays associated with the capture of the required multiple images. The improved wavefront sensing heads include a beam splitter 353 and multiple imaging devices that cooperate to capture multiple images of different planes between the lenslet array itself and the focal plane of the lenslet array as required by the operations of FIG. 19. In these configurations, the beam splitter 353 splits the light beams produced by the lenslet array 307 into multiple arms (preferably of equal intensity) which are projected onto the multiple imaging devices. For example, as shown, beam splitter 353 splits the light beams produced by the lenslet array 307 into three arms (preferably of equal intensity) which are projected onto imaging devices 311-A, 311-B1 and 311-B2. Hereto, the beam splitter 353 may comprise one or more beam splitting elements, such as a cube-type beam splitter, plate-type beam splitter, or dichroic prism assembly as described above. In the configurations of FIGS. 20C and 20D, imaging devices 311-B1 and 311-B2 capture the image of the spot image plane (test spot pattern/reference spot pattern) at best focus and inside (or outside) of best focus, respectively, which are used to dynamically identify the sub-arrays (pixel areas) of the Hartmann spot imaging device 311-B1 (e.g., the imaging device that will be used for the determination of Hartmann spot positions) for a particular wavefront measurement.

Preferably, the image grabbing and processing operations of the reference spot image plane and the test spot image plane that dynamically identifying sub-arrays (pixel areas) of the Hartmann spot imaging device that avoid dot crossover are performed concurrently (or near concurrently) as part of each particular wavefront sensing measurement for the eye. Such concurrent (or near concurrent) operations enable accurate real-time wavefront measurement while the eye moves and/or accommodates.

In the configuration of FIG. 20C, imaging device 311-A is positioned to capture the fiducial point spot image formed by the lenslet array 307', which is preferably used to identify the geometric reference to nominal null for the wavefront sensor as described above. Preferably, the illumination of the reference beam and subsequent image grabbing and processing operations that derive the locations of the fiducial reference spots for each given lenslet are performed as a calibration operation prior to wavefront sensing measurements for an eye. Moreover, such operations can be used dynamically (in a manner concurrent with or interposed with such wavefront sensing measurements) to perform such calibration as frequently as required to ensure the accuracy of the system. Such dynamic operations (which may be concurrent with or interposed with wavefront sensing measurements) enable accurate real-time wavefront measurement while the eye moves and/or accommodates.

In the configuration of FIG. 20D, imaging device 311-A is mounted on a linear actuator that provides sufficient travel to allow the imaging device 311-A to capture multiple images of the pupil image plane, which are used to i) generate the geometric reference of nominal null for the wavefront sensor as described above with respect to FIG. 15, and ii) perform the dynamic calibration operations as described above with respect to FIG. 17. Preferably, the illumination of the reference beam and subsequent image grabbing and processing operations that derive the locations of the lenslet center location for each given lenslet are performed as a calibration operation prior to wavefront sensing measurements for an eye. Moreover, such operations can be used dynamically (in a manner concurrent with or interposed with such wavefront sensing measurements) to perform such calibration as frequently as required to ensure the accuracy of the system. Such dynamic operations (which may be concurrent with or interposed with wavefront sensing measurements) enable accurate real-time wavefront measurement while the eye moves and/or accommodates.

Advantageously, all of these configurations avoid delays associated with capture of the required multiple images and greatly improves the ease of measurement of ocular aberrations. More specifically, such configurations enable the wavefront sensor to monitor the high order aberrations of the eye while the eye moves, thereby avoiding the requirement that eye be physically immobilized and greatly improving the comfort of the patient when measuring the aberrations of the eye.

Moreover, such configurations enable the wavefront sensor to monitor the high order aberrations of the eye while the eye changes focus (i.e., accommodation occurs). As described above. this is important in measuring the aberrations of the eyes of children at an early age (for example, early age screening for vision impairments such as ambiopia. In such circumstances, drugs that paralyze accommodation (commonly called Cycloplegics) are typically used to measure the aberrations of the eye. Such drugs typically require a long time to take effect (30–60 minutes). In the event that the required time period for inducement of paralysis is not satisfied, prior art ophthalmic instruments are error prone in measuring the aberration of the eye and thus susceptible to misdiagnosis. In addition, such drugs typically require a long wear off (up to 24 hours), which leads to patient discomfort over this prolonged period. By avoiding the use of such drugs, the ophthalmic instrument of the present invention avoids these problems, thereby minimizing the delays and inconveniences in examining and treating such patients and enabling more accurate and efficient ocular measurements and diagnosis.

In addition, such configurations enable active (e.g., dynamic) mapping of the local tilt measurements to the pupil of the eye, which significantly improves the accuracy of the measurements performed by the wavefront sensor and the accuracy of the resulting wavefront data produced by the ophthalmic instrument.

Spot Location Utilizing Spot Fitting

The Shack-Hartmann wavefront sensors discussed above are a class of Hartmann wavefront sensors. A Hartmann wavefront sensor includes one or subapertures that spatially sample incident light, one or more optical elements (such as refractive lens, diffractive grating or diffractive hologram) that focus the samples to spots, and a mechanism for measuring location of the spots. Exemplary Hartmann wavefront sensors are illustrated in FIGS. 21A–21C.

Figure 21A:
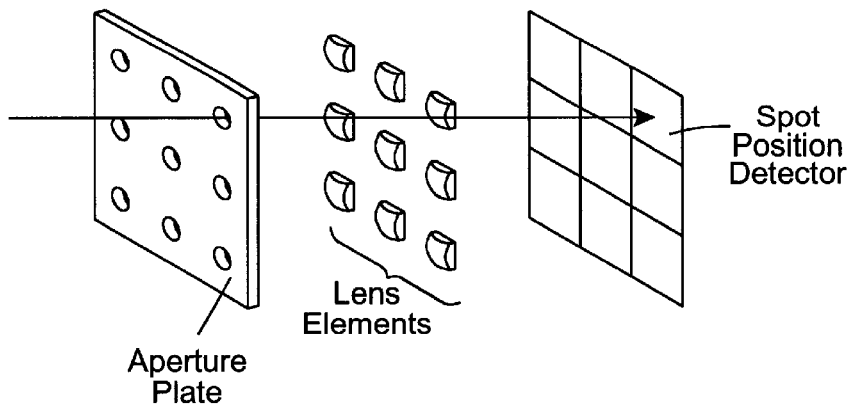
FIGS. 21A–21C are pictorial illustrations of exemplary Hartmann wavefront sensors.

The Hartmann wavefront sensor of FIG. 21A includes an aperture plate having a plurality of subapertures each sampling different spatial parts of an incident light beam and corresponding lens elements that focus the samples to spots. The location of each spot is measured by a spot position detector.

Figure 21B:
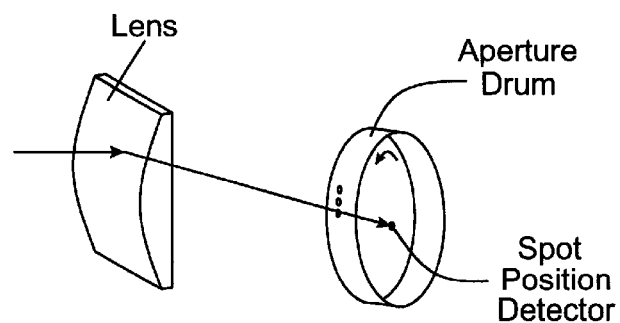

The Hartmann wavefront sensor of FIG. 21B includes a lens that focuses incident light to one or more spots at a focal point, and a spot position detector placed at that focal point. A scanning aperture drum is located between the lens and the spot position detector. The drum includes a plurality of subapertures that are offset from one another to thereby spatially sample the incident light directed thereto as the drum is rotated (i.e., each subaperture samples a vertical scan line of the footprint of incident light on the rotating drum). The spot position detector measures the location of the spot that is formed from the sample of light that passes through each subaperture of the rotating drum.

Figure 21C:
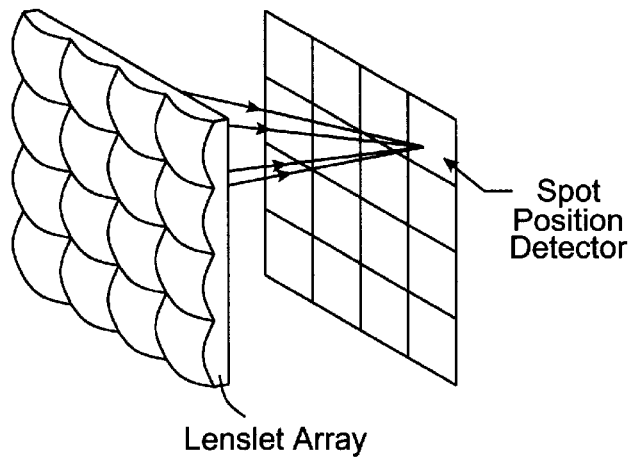
Figure 22:
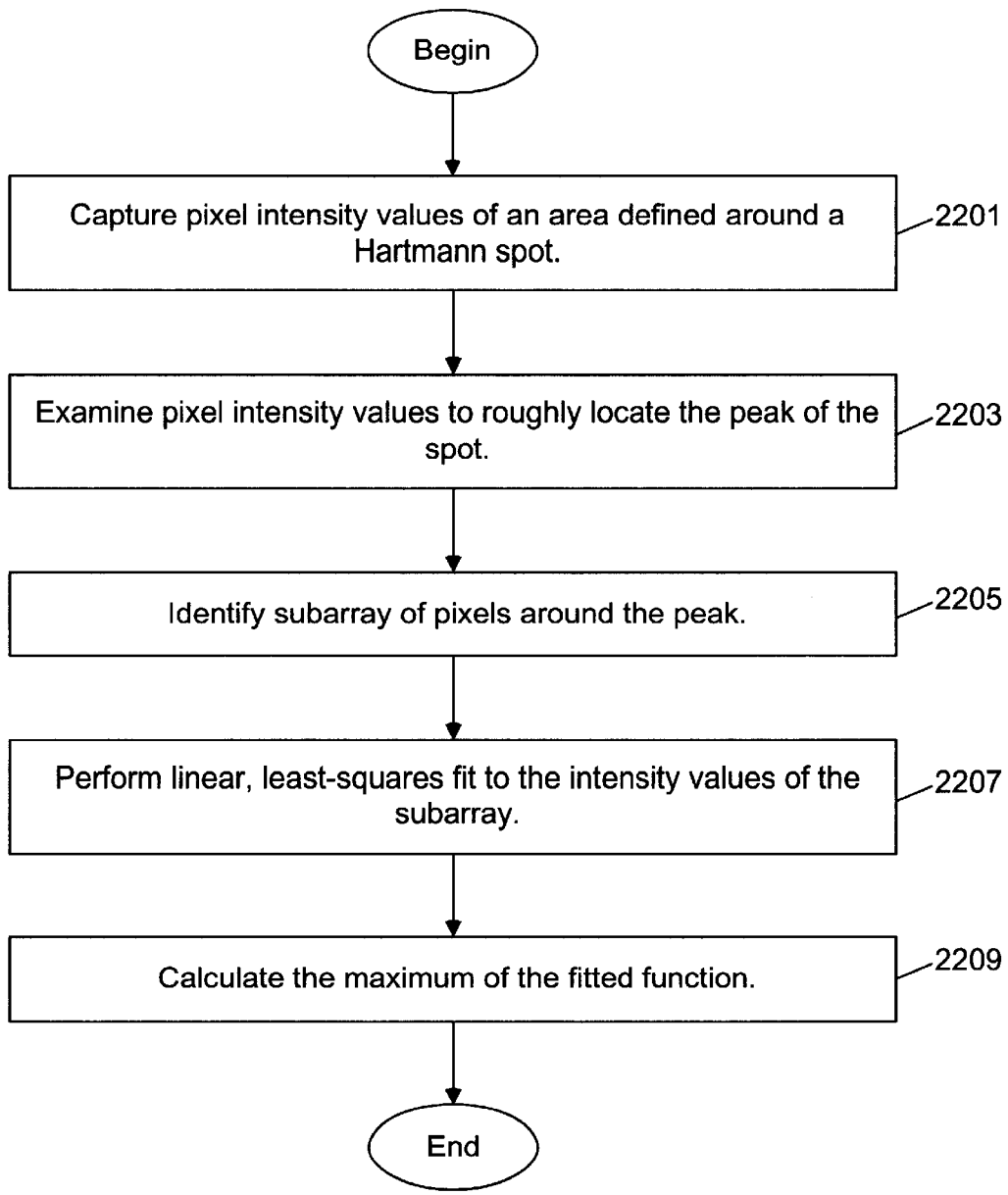
FIG. 22 is a flow chart illustrating an improved technique (embodied within a Hartmann wavefront sensor and ophthalmic instrument utilizing such a sensor) that determines the location of the Hartmann spot in a given pixel subaperture defined around that spot in a manner that provides better performance (e.g., a lower threshold signal-to-noise ratio) under such real-world conditions.

The Hartmann wavefront sensor of FIG. 21C includes a monolithic lenslet array having a plurality of subapertures (lenslets) each sampling different spatial parts of an incident light beam and focusing the samples to spots. The location of each spot is measured by a spot position detector.

The basic measurement performed by any Hartmann wavefront sensor is the determination of the locations of the Hartmann spots. Traditionally, this has been done by calculating the centroid of the illumination in a pixel subaperture defined around each spot. It can be shown that the position of the centroid of light is directly related to the average tilt of the wavefront over the pixel subaperture. Unfortunately, as described above in detail in the Background of Invention, centroid calculation has a number of difficulties (including a high threshold signal-to-noise ratio) that limit its usefulness in many real-world applications.

The performance of such traditional Hartmann wavefront sensors can be enhanced through the use of an improved technique for determining the location of the Hartmann spot in a given pixel subaperture defined around that spot. The improved technique, which is preferably executed by an image sensor and image processing device embodied within the Hartmann wavefront sensor, is described below with reference to the flow chart of FIG. 22.

In step 2201, an image sensor captures image data (pixel intensity values) of an area defined around a Hartmann spot (e.g., pixel subaperture) and provides the image data to the image processor.

In step 2203, the image processor exams the intensity values of the pixels of this pixel subaperture to roughly locate the peak of the spot. This may be accomplished simply by finding the pixel (of the pixel subaperture) with the maximum intensity value.

In step 2205, the image processor identifies a subarray of pixels around the peak located in step 2203. A typical size for this sub-array is five by five (5×5) pixels, but it can be adjusted depending upon the parameters of the wavefront sensor.

In step 2207, the image processor performs a linear, least-squares fit on the intensity values of the subarray identified in step 2105. A function that approximates the shape of the peak of the spot is used for the fit. An example of such a function is a parabolic function of the form:

$$I = Ax^2 + Bxy + Cy^2 + Dx + Ey + F,$$

where I is the intensity signal in the extracted region and x and y are the pixel coordinates.

Finally, in step 2109, the image processor calculates the maximum of the fitted function (in pixel space). This may be accomplished by solving the simultaneous equations $\Upsilon I/\Upsilon x=0, \Upsilon I/\Upsilon y=0$, or by solving the equivalent equations $2Ax_p + By_p + D=0$, $Bx_p + 2Cy_p + E=0$, where $x_p$ and $y_p$ are the x,y coordinates of the peak of the fit. This maximum is the estimate of the location of the spot.

Because this technique can be controlled to ignore pixels far from the spot, it is much less sensitive to errors in background subtraction as described above. Furthermore, only the pixels in the subarray contribute noise to the measurement. Both of these factors contribute to an improved signal-to-noise ratio.

According to the present invention, a Hartmann wavefront sensor (including any of the Shack-Hartmann wavefront sensor configurations described above) utilizing this improved technique is embodied within an ophthalmic instrument to measure the aberrations of the human eye. Such improvements are broadly applicable to (and can be embodied within) ophthalmic instruments that are used to examine or treat the eye, including ophthalmic examination instruments (such as phoropters and autorefractors) that measure and characterize the aberrations of the human eye in addition to ophthalmic imaging instruments (such as fundus cameras, corneal topographers, retinal topographers, corneal imaging devices, and retinal imaging devices) that capture images of the eye.

The improvements provide an ophthalmic instrument with significant advantages. More specifically, the light level of the retinal reflections returning from the eye is typically quite low due to the following constraints: the retina is not very reflective, and the brightness of the wavefront sensing illumination source cannot be raised without limit because of eye safety concerns and by the desire for subject comfort. In addition, background illumination (e.g., noise) is almost certainly present (either from scattering in the system and the sensor or from room light). In such an environment, background noise represents a problem. Advantageously, the robustness of the technique described above for determination of the locations of the Hartmann spots provides an improved signal-to-noise ratio that enables high quality wavefront measurements of the eye under a wider range of operating conditions (e.g., in noisier environments).

Extended Source

In another aspect of the present invention, improved Hartmann wavefront sensing mechanisms (and improved ophthalmic instruments utilizing these mechanisms) are provided that utilize an extended source to improve the signal-to-noise ratio of the wavefront measurements calculated therein.

Note that Hartmann wavefront sensing mechanisms described above all share the same basic configuration—a small spot is projected onto the retina and retro-reflected light that emerges from the eye is directed to a Hartmann wavefront sensor that measures the phase aberrations in the retro-reflected light directed thereto. If the spot is small enough to act as a point source, that phase aberrations measured by the Hartmann wavefront sensor is representative of the aberrations of the eye.

As discussed above, the light level of the retinal reflections returning from the eye is typically quite low due to the following constraints: the retina is not very reflective, and the brightness of the wavefront sensing illumination source cannot be raised without limit because of eye safety concerns and by the desire for subject comfort. In addition, background illumination (e.g., noise) is almost certainly present either from scattering in the system and the sensor or from room light. In such an environment, background noise represents a problem.

Figure 25A:
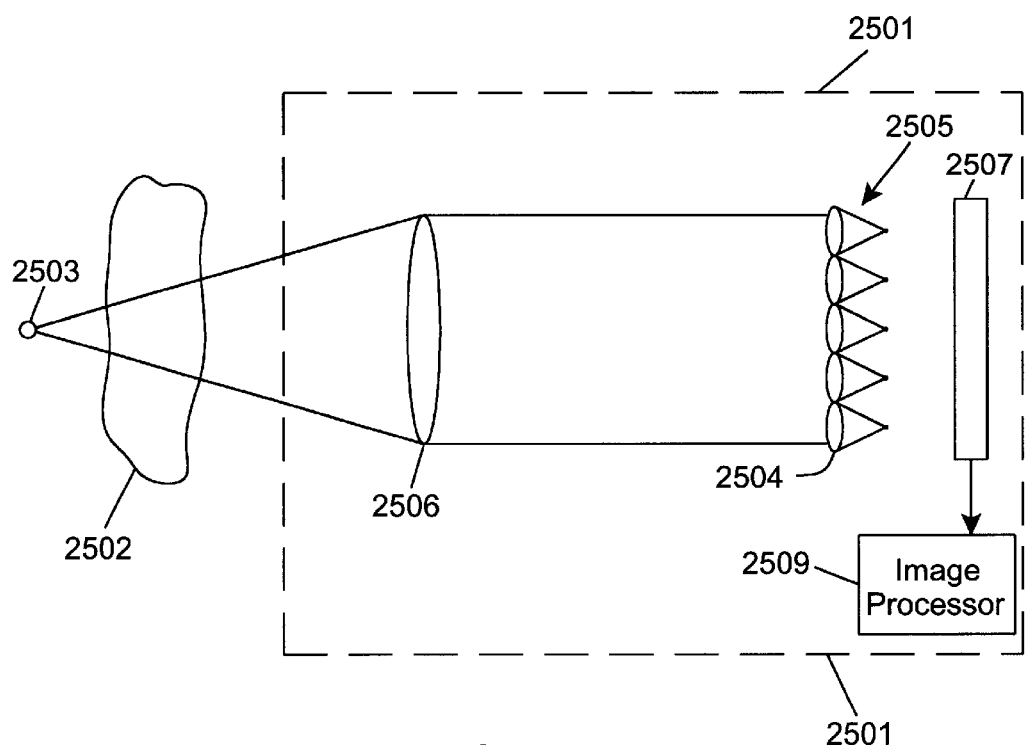
FIG. 25A is a schematic illustration of typical Hartmann wavefront sensors.

FIG. 25A illustrates a typical Hartmann wavefront sensor 2501 in which an aberration-inducing medium 2502 is disposed between a point source 2503 and the sensor 2501. The sensor 2501 includes foreoptics 2506 and a plurality of subapertures 2504 (e.g., lens array) that re-image the point source 2503 to form the Hartmann spot pattern 2505. Foreoptics 2506 is drawn as a refractive type element. However, it is well known to those skilled in the optical engineering art that such foreoptics 2506 can include one or more reflective, refractive or diffractive type elements. Each subaperture samples a small portion of the full input pupil of the sensor 2501. An imaging device 2507 captures images of the Hartmann spot pattern 2505 formed by the subapertures 2503 and outputs image data representative of the Hartmann spot pattern. An image processing computer 2509 generates an estimate of the gradient field of the input wavefront by analyzing the image data to derive a measure of the locations of the centroids of the spots in the Hartmann spot pattern. The location of the centroid of a given spot is simply related to the tilt of the wavefront over the subaperture that forms the given spot.

Figure 25B:
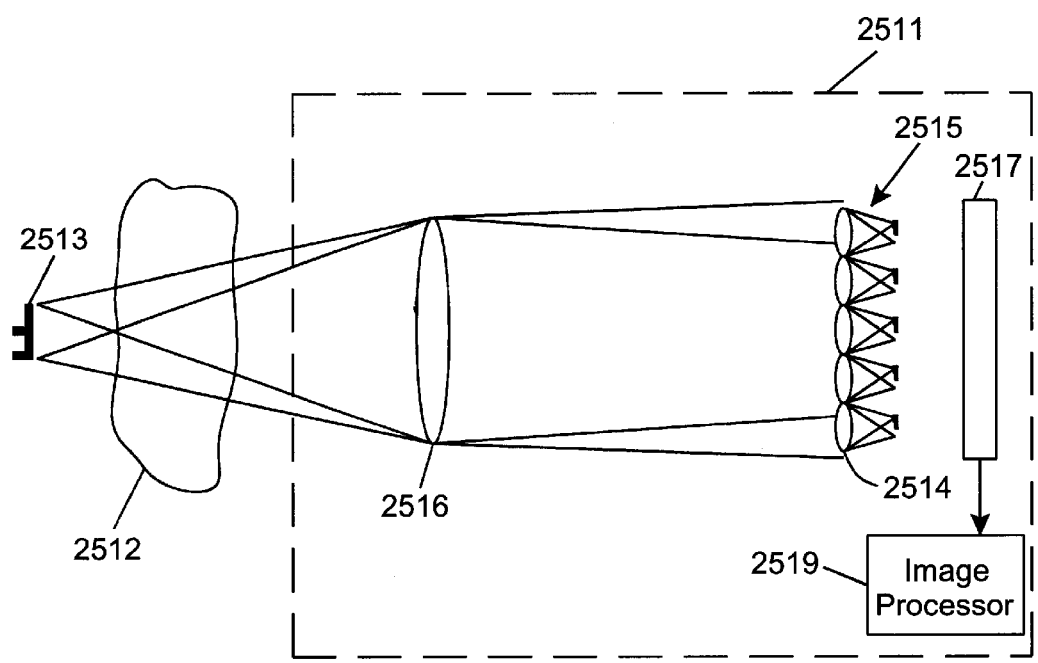
FIG. 25B is a schematic illustration of an improved Hartmann wavefront sensor for use in an ophthalmic instrument according to the present invention, which includes an extended source that improves the signal-to-noise ratio of the wavefront measurements calculated therein.

FIG. 25B illustrates an improved Hartmann wavefront sensor 2511 in which an aberration-inducing medium 2512 is disposed between an extended source (an illumination source of arbitrary dimensions) 2513 and the sensor 2511. The sensor includes foreoptics 2516 and a plurality of subapertures 2514 (e.g., lens array) that form a plurality of images 2515 of the extended source 2513. Foreoptics 2516 is drawn as a refractive type element. However, it is well known to those skilled in the optical engineering art that such foreoptics 2516 can include one or more reflective, refractive or diffractive type elements. Each subaperture samples a small portion of the full input pupil of the sensor 2511. An imaging device 2517 (e.g., one or more CCD-based or CMOS-based image sensors) capture the plurality of images 2515 of the extended source 2513 formed by the subapertures 2513 and outputs image data representing such images 2515. An image processing computer 2519 generates an estimate of the gradient field of the input wavefront by applying image processing techniques to the image data representing such images 2515.

Importantly, the dimensions of the extended source 2513 can be larger that a diffraction limited spot, yet must be small enough so that different parts of the image do not experience substantially different aberrations while passing through the aberration-inducing medium 2512. In addition, as is evident from FIG. 25B, the angular size of the extended source 2513 must be limited so that the images 2515 formed by each subaperture (e.g., lenslet) do not overlap, which would lead to confusion in the image plane. In general, this may be accomplished through the use of an aperture stop (not shown) at the input image plane of the sensor 2511 that limits the angular field of view.

According to the present invention, the improved Hartmann sensor 2511 of FIG. 25B is embodied with an ophthalmic instrument to measure the aberrations of the eye. Importantly, the use of the extended source as the wavefront sensing illumination source and the formation of the virtual extended source on the retina spreads light over a larger region of the retina (than the prior art approach as described above that produced a spot image of the wavefront sensing illumination source on the retina), which allows for the use of greater total optical power while keeping the power density the same as in this prior art approach. The resulting use of greater total optical power improves the signal-to-noise ratio of the ophthalmic instrument, thereby enabling high quality wavefront measurements of the eye under a wider range of operating conditions (e.g., in noisier environments).

When using the extended source 2513, it is necessary that the image processing computer 2519 of the wavefront sensor 2511 utilize a more sophisticated image processing algorithm to estimate the subaperture tilt of the incident wavefronts (which are derived from retinal reflections of the extended source 2513). Preferably, image correlation techniques in the digital domain are applied to image data that represents the plurality of images 2515 of the extended source 2513 (which is output by the imaging device 2517) to derive a correlation product for a given image $2515_i$ and corresponding subaperture $2514_j$. The peak correlation point of the correlation product for the given image $2515_i$/subaperture $2514_j$ provides the tilt estimate of the incident wavefront over the given subaperture $2514_j$.

The correlation of two images $I_1$ and $I_2$ in the digital domain may be generally represented as the product:

$$\sum_{p_1 \in w_1} \sum_{p_2 \in w_2} p_1 \otimes p_2$$

where $p_1$ is the pixel index running over the domain of interest $w_1$ in the image $I_1$, and $p_2$ is the pixel index running over the domain of interest $w_2$ in the image $I_2$.

The correlation product (denoted by $\otimes$) can be defined by many different functions. For example, the correlation product can be defined by the sum of squared differences function as follows:

$$p_1 \otimes p_2 = \sum_{w_1, w_2} (p_1 - p_2)^2$$

In this example, the correlation product describes a measure of difference between the two interest regions of the images and represents the quantity to be minimized to find the peak correlation point. In a second example, the correlation product can be defined by the sum of products function as follows:

$$p_1 \otimes p_2 = \sum_{w_1, w_2} (p_1 p_2)$$

In this second example, the correlation product describes a measure of resemblance between the two interest regions of the images and represents the quantity to be maximized to find the peak correlation point. Other correlation products that can be used differ from these two by the fact that they include scale and possible offset normalization in luminance.

Figure 26:
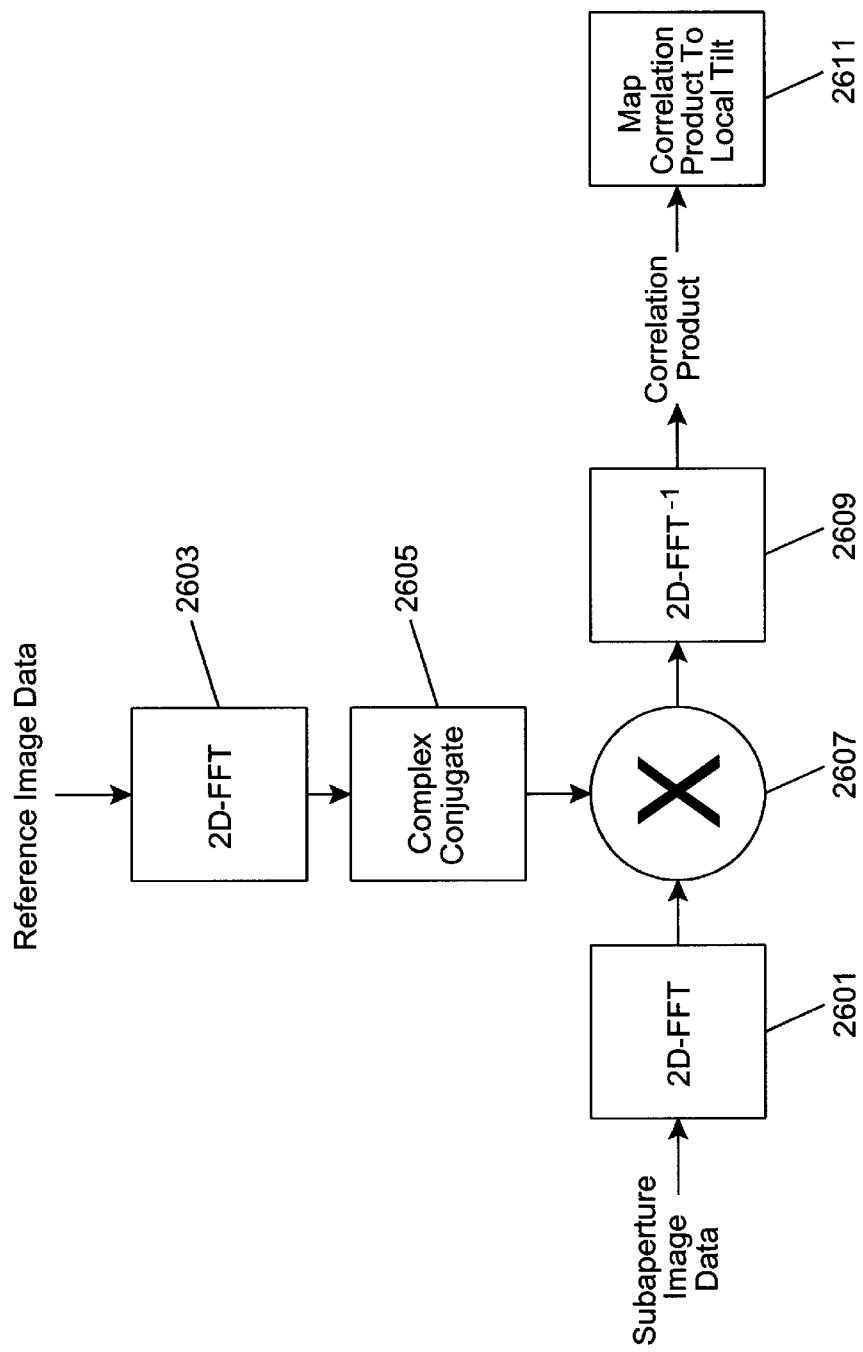
FIG. 26 is a functional block diagram that illustrates image correlation techniques in the digital domain that are applied to the image data that represents an image of the extended source to estimate the local tilt of the incident wavefront over a subaperture of the sensor. This technique is applied to the image data for each image of the extended source (for the plurality of images of the extended source that are formed by the subapertures of the sensor) to estimate the local tilt of the incident wavefront over the subapertures of the sensor.

FIG. 26 is a schematic illustration of an exemplary image correlation algorithm, which can be embodied by the image processing computer 2519, to derive a correlation product for a given subaperture image $2515_i$. The peak correlation point of the correlation product for the given image $2515_i$ provides the tilt estimate of the incident wavefront over the corresponding subaperture $2514_j$ that forms the given image $2515_i$.

As shown, the correlation product for a given image $2515_i$ is derived from the image data (pixel intensity values) of an area defined around the given image $2515_i$, which is provided by the imaging device 2517 and denoted "subaperture image data" for the sake of description. In addition, the correlation product for a given image $2515_i$ is derived from reference image data. The reference image data may based upon: the collection of image data (over time) for given image $2515_i$; a collection of image data for a plurality of subapertures, for example, comprising the average subaperture image (wherein each pixel in the average subaperture image represents the average intensity value for that pixel over of all of the subaperture image data); or a reference source, for example, formed by projecting a perfect (or substantially non-aberrated) image of the extended source 2513 (or like source) onto the plane of the subapertures 2514 and capturing the images formed by the subapertures 2514 in response to this reference.

In block 2601, a two-dimensional Fourier transform of the subaperture image data is calculated. 1507, the image processor calculates the real and imaginary parts of a two-dimensional Fourier transform of the third composite image generated in step 1505. The two-dimensional Fourier transform can generally be represented as follows:

$$F(k, l) = \frac{1}{NM} * \sum_{x=0}^{N-1} \sum_{y=0}^{M-1} f(x, y) e^{-i2\Pi\left(\frac{kx}{N} + \frac{ly}{M}\right)}$$

where N represents the number of pixels in each row (i.e., x direction) of the image data;
M represents the number of pixels in a column (i.e., y direction) of the image data;
f(x,y) represents the intensity value at a pixel (x,y) in the image data; and
the exponential term is the basis function corresponding to each point F(k,l) in Fourier space.

This transform can be calculated as a double sum at each image point as follows:

$$F(k, l) = \frac{1}{M} * \sum_{y=0}^{M-1} P(k, y) e^{-i2\Pi \frac{ly}{M}}$$

where $$P(k, y) = \frac{1}{N} * \sum_{x=0}^{N-1} f(x, y) e^{-i2\Pi \frac{kx}{N}}$$

In block 2603, a two-dimensional Fourier transform of the reference image data is calculated. These operations are similar to the operations described above for the subaperture image data.

In block 2605, the complex conjugate function is applied to the resultant Fourier transform data calculated in block 2603. As is well known, the complex conjugate function operates to flip the sign of the imaginary part of the Fourier transform data calculated in block 2603.

In block 2607, the Fourier transform data calculated in block 2601 is multiplied by the resultant data calculated in block 2605.

In block 2609, a two-dimensional inverse Fourier transform of the resultant data of block 2607 is calculated. The result of the two-dimensional inverse Fourier transform is the correlation product for the given subaperture image $2515_i$. The two-dimensional inverse Fourier transform can be generally represented as follows:

$$f(x, y) = \frac{1}{NM} * \sum_{k=0}^{N-1} \sum_{l=0}^{M-1} F(k, l) e^{i2\Pi \left(\frac{kx}{N} + \frac{ly}{M}\right)}$$

where
  N represents the number of pixels in each row (i.e., x direction) of the image data;
  M represents the number of pixels in a column (i.e., y direction) of the image data;
  f(x,y) represents the intensity value at a pixel (x,y) in the image data; and
  the exponential term is the basis function corresponding to each point F(k,l) in Fourier space.

Finally, in block 2611, the peak correlation point (i.e., the maximum quantity in this example) of the correlation product generated in block 2609 is identified. This peak provides the tilt estimate of the incident wavefront over the corresponding subaperture $2514_j$ that forms the given subaperture image $2515_i$.

These local tilt estimates can then be reconstructed to form data representative of the aberrations (including defocus, spherical aberration, coma, astigmatism in addition to other higher order aberrations) of the distorted wavefront incident on the subapertures 2514. For example, the local tilt estimates may be reconstructed into an optical path difference (OPD) array, which stores a scalar value that represents the optical path difference at each subaperture. Alternatively, the local tilt estimates may be reconstructed into an OPD function, for example, by minimizing the difference between the derivatives of an analytical function (such as a set of Zernike polynomials, Seidel polynomials, Hermites polynomials, Chebychev polynomials, and Legendre polynomials) and the measured local tilt estimates.

In addition, the data representative of the aberrations (including defocus, spherical aberration, coma, astigmatism in addition to other higher order aberrations) of the distorted wavefront incident on the subapertures 2514 is preferably used to generate a graphical representation (such as a wavefront map that depicts the OPD over the pupil, e.g., subapertures, of the wavefront sensor 2511', or a graphical display of the coefficients of the OPD function as illustrated in FIG. 6C) of the aberrations of the eye 1.

Note that the correlation operations of FIG. 26 are primarily carried out by applying the multiplication of a complex conjugate in the frequency domain. Carrying out the correlation operations in the frequency domain provides inherent computational efficiency for large images. However, one skilled in the image processing arts will realize that these operations are analogous to computing the correlation as a sum of products of the subaperture image data and the reference image data in the spatial domain. In some cases (e.g., where the subaperture image data and the reference image data are not large), it may be advantageous to perform the correlation operations in the spatial domain.

The improved Hartmann wavefront sensor 2511 of FIG. 25B was demonstrated in the laboratory. The extended source 2513 comprised several handwritten characters on a piece of paper illuminated with a tungsten lamp. This extended source 2513 was placed about 3 meters away from the foreoptics 2513 that supplies the collimated input to the subapertures 1514 (e.g., lenslet array) of the sensor 2511. The aberration inducing medium 2512 was simulated wherein defocus of the images of the extended source was induced by varying the focal power of the foreoptics 2513 by a predetermined amount and measuring the wavefront. The measured focal change agreed to better than 1/10 wave with the predetermined change in focus.

As described above, the improved Hartmann sensor 2511 is broadly applicable to (and can be embodied within) ophthalmic instruments that are used to examine or treat the eye, including ophthalmic examination instruments (such as phoropters and autorefractors) that measure and characterize the aberrations of the human eye in addition to ophthalmic imaging instruments (such as fundus cameras, corneal topographers, retinal topographers, corneal imaging devices, and retinal imaging devices) that capture images of the eye.

Figure 27A:
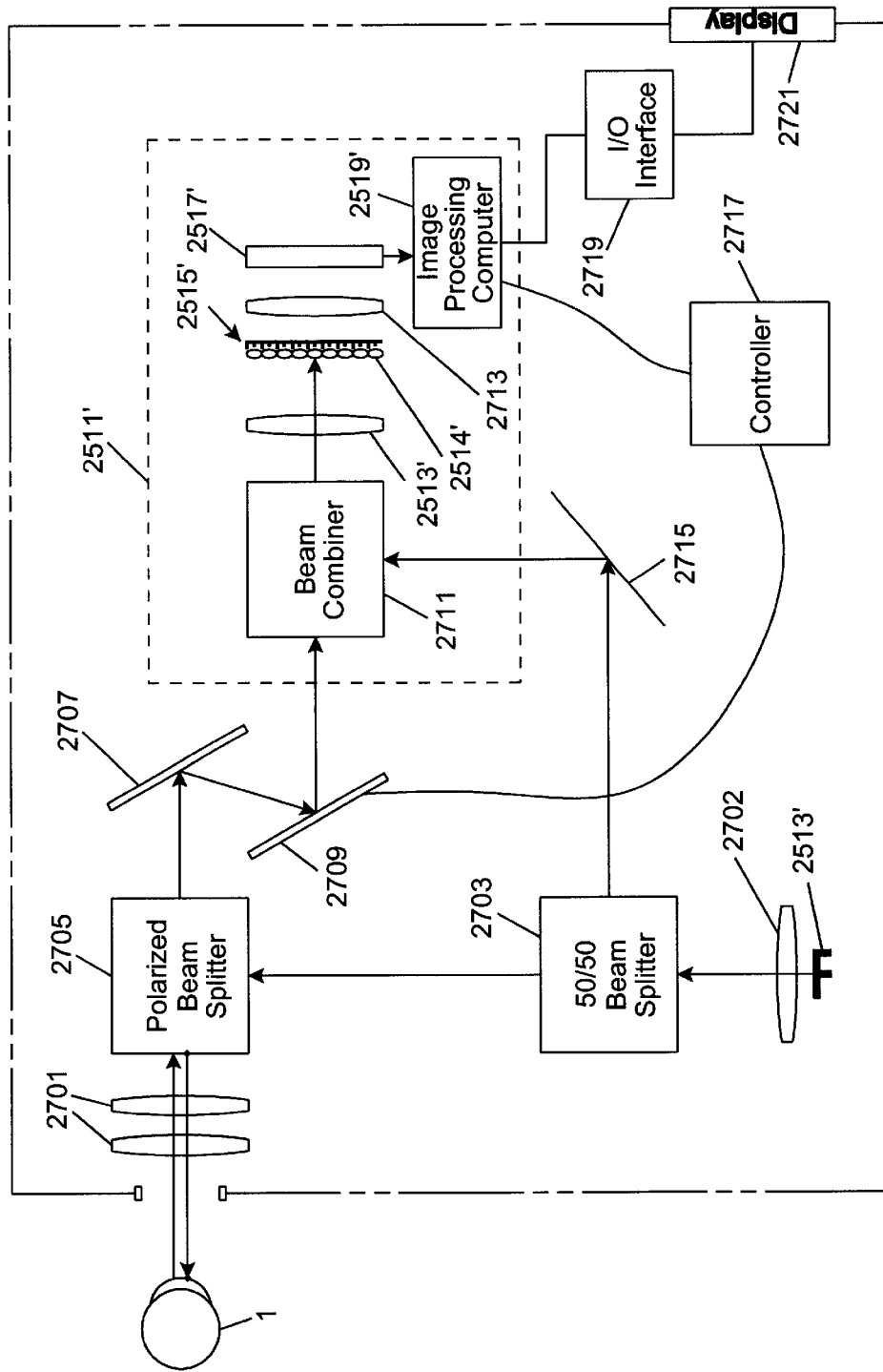
FIGS. 27A and 27B are schematic representations of exemplary ophthalmic instruments that embody the improved Hartmann wavefront sensor of FIG. 25B according to the present invention. The ophthalmic instruments project an image of an extended source onto the retina of the eye(s), capture a plurality of images of the extended source (derived from the retinal reflections of the projected extended source that are formed by the subapertures of the sensor), and apply image correlation techniques in the digital domain to image data derived from the plurality of images of the extended source in order to estimate the local tilt of such retinal reflections. The local tilt estimates are reconstructed to form data representative of the aberrations (including defocus, spherical aberration, coma, astigmatism in addition to other higher order aberrations) of such retinal reflections, which are characteristic of the aberrations of the eye(s) of the patient. The ophthalmic instrument of FIG. 27B provides wavefront sensing, an internal fixation target, and high resolution image capture capabilities according to the present invention.

Referring now to FIG. 27A, there is shown, in schematic form, an exemplary ophthalmic instrument according to the present invention, which embodies the improved wavefront sensor of FIG. 25B. As shown, the ophthalmic instrument 2701 includes an extended source 2513' for use as the wavefront sensing illumination source. The optical train of the instrument forms an image of the extended source 2513' (which for the sake of description is denoted "virtual extended source") on the retina of the eye 1, which is reflected (and exits the pupil of the eye as distorted wavefronts) and directed back to the instrument 2701. The light produced from the extended source 2513' forms substantially planar (e.g., phase-aligned) wavefronts that are directed to the pupil of the eye 1. These wavefronts are imaged onto the retina of the eye 1 by the crystalline lens thereby forming the virtual extended source. The optical aberrations of the eye 1, such as defocus (which may be myopia (near-sightedness) or hyperopia (farsightedness)) and astigmatism as well has many other higher order optical aberrations, cause the light reflected from the retina of the eye 1 (including reflections of the virtual extended source) to form distorted wavefronts at the pupil of the eye 1 as it leaves the eye 1.

The optical train of the instrument 2701 creates an image of these distorted wavefronts (which are derived from retinal reflections of the virtual extended source) on a phase compensator 2709, which spatially modulates the phase of the image of the distorted wavefronts incident thereon to produce a compensated image of such distorted wavefronts. This compensated image is recreated at the wavefront sensor 2511'.

The wavefront sensor 2511' measures the phase aberrations in the distorted wavefronts incident therein (which are derived from retinal reflections of the extended source 2513') and operates in a closed-loop fashion with a controller 2717 to control the phase compensator 2709 (which preferably comprises a variable focus lens and deformable mirror as described below) to compensate for such phase aberrations to restore the distorted wavefronts to phase-aligned wavefronts, which are directed to the wavefront sensor 2511' (for further wavefront measurement and compensation if required).

In addition, the wavefront sensor 2511' is preferably operably coupled (for example, via I/O interface 2720 as shown) to a display device 2721 that generates a graphical representation (such as a wavefront map that depicts the OPD over the pupil, e.g., subapertures, of the wavefront sensor 2511', or a graphical display of the coefficients of the OPD function as illustrated in FIG. 6C) of the aberrations of the eye 1 as measured by the wavefront sensor 2511'.

As shown in FIG. 27A, the optical train of the instrument 2701 preferably include lens 2702, beam splitter 2703, polarizing beam splitter 2705 and relay lens pair 2707 that cooperate to form the virtual extended source (i.e., the image of the extended source 2513' on the retina of the eye 1), which is reflected and exits the pupil of the eye as distorted wavefronts and then directed back to the instrument. The relay lens pair 2707, polarizing beam splitter 2705 and beam folding mirror 2707 create an image of these distorted wavefronts at phase compensator 2709. The phase compensator 2709, under control of controller 2717, operates to spatially modulate the phase of the image of the distorted wavefronts incident thereon to produce a compensated image of such distorted wavefronts that compensate for the aberrations of the eye under examination. This compensated image is recreated at the wavefront sensor 2511' for wavefront sensing.

As shown in FIG. 27A, the wavefront sensor 2511' includes beam combiner 2711, foreoptics 2516' and a plurality of subapertures 2514' (e.g., lens array) that cooperate to form a plurality of images 2515' of the virtual extended source (i.e., the image of the extended source 2513' formed on the retina of the eye 1). Relay lens 2713 and imaging device 2517' (e.g., one or more CCD-based or CMOS-based image sensors) cooperate to capture the images 2515'. The imaging device 2517' outputs image data representing such images 2515'. An image processing computer 2519' generates an estimate of the gradient field of the compensated image of the distorted wavefronts provided by the phase compensator 2709 by applying image processing techniques to the image data representing images 2515'. More specifically, the image processing computer 2519' applies image correlation techniques in the digital domain to such image data to derive a correlation product for a given image 2515$_i$ and corresponding subaperture 2514$_j$. The peak correlation point of the correlation product for the given image 2515$_i$/subaperture 2514$_j$ provides the tilt estimate of the incident wavefront (i.e., the compensated image of the distorted wavefront provided by the phase compensator 2709, which is derived from retinal reflections of the extended source 2513') over the given subaperture 2514$_j$.

As described above, the correlation product for a given image 2515$_i$ may be derived from reference image data. The reference image data may based upon the collection of image data for a plurality of subapertures, for example, comprising the average subaperture image (wherein each pixel in the average subaperture image represents the average intensity value for that pixel over all of the subaperture image data). Alternatively, the reference image data may be based upon image data derived from a reference source, for example, formed by projecting a perfect (or substantially non-aberrated) image of the extended source 2513' (or like source) onto the plane of the subapertures 2514' and capturing the images formed by the subapertures 2514' in response to this reference. As shown in FIG. 27A, beam splitter 2703, beam folding mirror 2715 and beam combiner 2711 provide this functionality by projecting a perfect (or substantially non-aberrated) image of the extended source 2513' onto the plane of the subapertures 2514'. In embodiments wherein such functionality is not required, these elements may be omitted.

The local tilt estimates generated by the image processing computer 2519' can be reconstructed to form data representative of the aberrations (including defocus, spherical aberration, coma, astigmatism in addition to other higher order aberrations) of the incident wavefront (i.e., the compensated image of the distorted wavefront provided by the phase compensator 2709, which is derived from retinal reflections of the extended source 2513') on the subapertures 2514'. For example, the local tilt estimates may be reconstructed into an optical path difference (OPD) array, which stores a scalar value that represents the optical path difference at each subaperture. Alternatively, the local tilt estimates may be reconstructed into an OPD function, for example, by minimizing the difference between the derivatives of an analytical function (such as a set of Zernike polynomials, Seidel polynomials, Hermites polynomials, Chebychev polynomials, and Legendre polynomials) and the measured local tilt estimates.

The image processing computer 2519' is preferably operably coupled (for example via I/O interface 1720) to a display device 2721 that generates a graphical representation (such as a wavefront map that depicts the OPD over the pupil, e.g., subapertures, of the wavefront sensor 2511', or a graphical display of the coefficients of the OPD function as illustrated in FIG. 6C) of the aberrations of the eye 1 based upon the data representative of the aberrations (including defocus, spherical aberration, coma, astigmatism in addition to other higher order aberrations) of the incident wavefront as constructed by the image processing computer 2519'.

The dimensions of the image of the extended source 2513' formed on the retina of the human eye (i.e., the virtual extended source) can be larger that a diffraction limited spot, yet must be small enough so that different parts of the image do not experience substantially different aberrations while passing through the eye 1 (which is the aberration-inducing medium in this application). In addition, as is evident from FIG. 25B, there the angular size of the image of the extended source 2513' must be limited so that the images 2515' formed by each subaperture (e.g., lenslet) do not overlap, which would lead to confusion in the image plane. In general, this may be accomplished through the use of an aperture stop (not shown) at the input image plane of the sensor 2511' that limits the angular field of view.

The subapertures 2514' of the sensor 2511 preferably comprise a lenslet array of the type manufactured and sold by Adaptive Optics Inc, of Cambridge, Mass., assignee of the present invention, in that it comprises a precision array of refractive microlenses formed continuously on a monolithic substrate. The array of microlenses are preferably compression molded of polymethymethacrylate (PMMA)

plastic, and positioned in the substrate with full edge-to-edge lenslet contact to maximize the density of lens area to total surface area (referred to as "fill factor").

The phase compensator 2709 of the adaptive optic subsystem of the ophthalmic instrument 2701 preferably comprises multiple stages (such as the variable focus lens (VFL) and a deformable mirror as shown in FIG. 7A) that compensate for different parts of the aberrations of the eye 1 as estimated by the wavefront sensor 2511'. For example, such aberrations can be decomposed into a defocus component (which represents the defocus of the eye 1) and one or more additional components (which represent the higher order components (e.g., spherical aberration, astigmatism and coma) of such aberrations. In this case, the first stage (i.e., the variable focus lens) is used to compensate for the defocus component of such aberrations, and the one or more additional stages (i.e., deformable mirror) are used to compensate for the remaining higher order components of such aberrations. A deformable mirror achieves such compensation by warping its optical surface to form the complex conjugate of such higher order components as measured by the wavefront sensor 2511'. Exemplary silicon micromachined membrane deformable mirrors are described above with respect to FIGS. 8A and 8B.

Figure 27B:
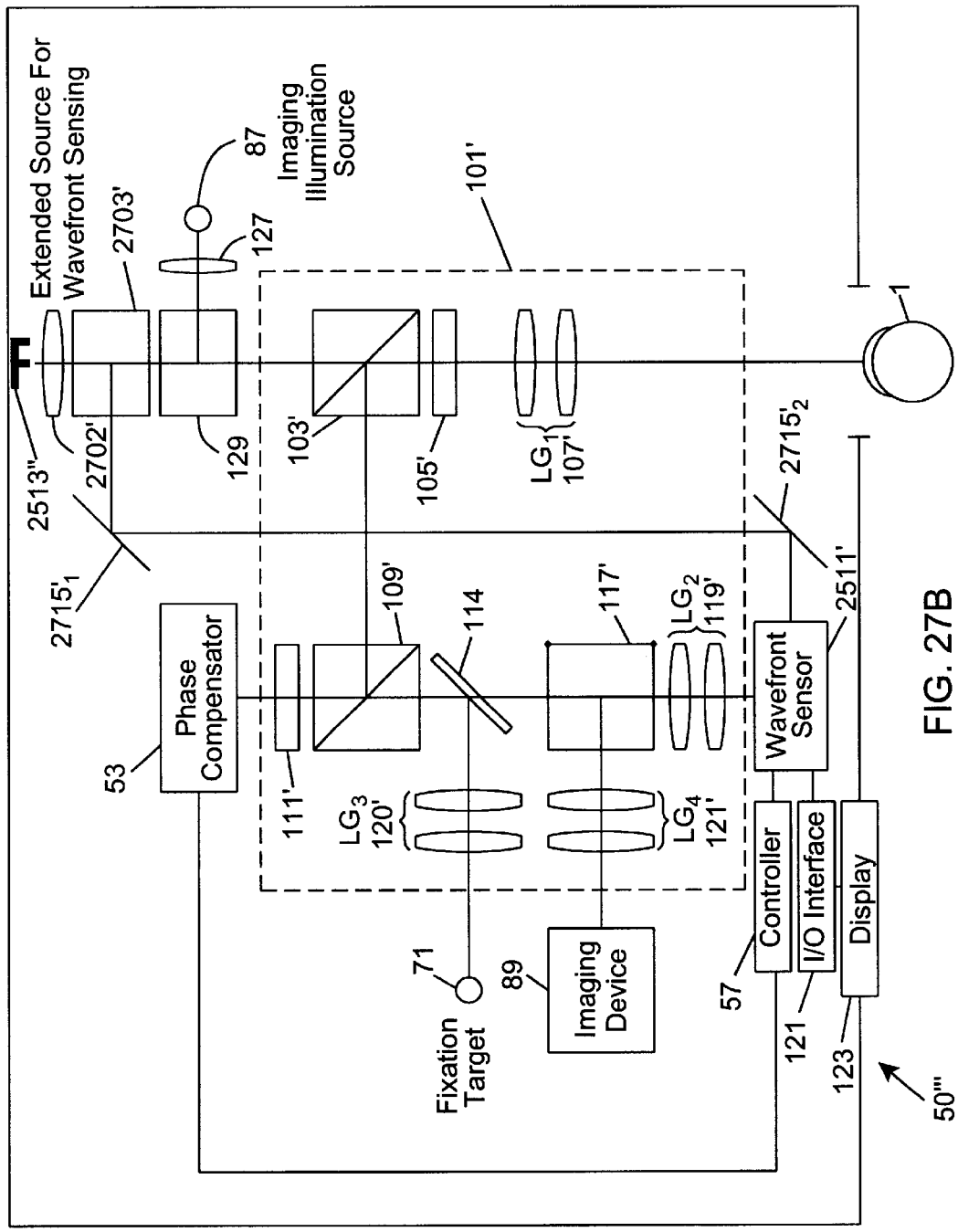

Referring now to FIG. 27B, there is shown, in schematic form, an exemplary ophthalmic instrument 50'''' according to the present invention, which embodies the improved wavefront sensor of FIG. 25B and provides the same functionality as the instrument of FIG. 6B as described above.

Wavefront sensing is provided by an extended source 2513'' that cooperates with lens 2702', beam splitter 2703', beam combiner 129', first polarizing beam splitter/quarter wave plate 103'/105' and first relay lens group $LG_1$ to form a virtual extended source (i.e., image of the extended source 2513'') on the retina of the eye 1, which is reflected (and exits the pupil of the eye as distorted wavefronts) and directed back to the instrument 50''''. The first relay lens group $LG_1$, first polarizing beam splitter/quarter wave plate 103'/105' and second polarizing beam splitter/quarter wave plate 109'/111' create an image of the distorted wavefronts on a phase compensator 53. The phase compensator 53 (which preferably comprises a variable focus lens and deformable mirror as described below) operates to spatially modulate the phase of the wavefronts incident thereon to create a compensated image of such distorted wavefronts. The second polarizing beam splitter/quarter wave plate 109'/111', dielectric filter 114, beam splitter 117' and second relay lens group $LG_2$ recreate the image of such compensated wavefronts at wavefront sensor 2511'. The dielectric filter 114 operates to selectively reflect the band of light provided by the fixation target 71, while passing the band of light provided by the extended source 2513'' (and used for wavefront sensing) in addition to the band of light provided by the imaging illumination source 97 (and used for image capture).

The wavefront sensor 2511' measures the phase aberrations in the wavefronts incident thereon (i.e., the compensated image of the distorted wavefront provided by the phase compensator 53, which is derived from retinal reflections of the extended source 2513') and operates in a closed-loop fashion with a controller 57 to control the phase compensator 53 to spatially modulate the phase of the wavefronts incident thereon to compensate for such phase aberrations to thereby restore the distorted wavefronts to phase-aligned wavefronts, which are directed to the wavefront sensor 2511' (for further wavefront measurement and compensation if required).

The wavefront sensor 2511' is preferably operably coupled (for example, via I/O interface 121) to a display device 123 that generates a graphical representation of the aberrations of the eye 1 as measured by the wavefront sensor 2511'. For example, the graphical representation of the aberrations of the eye 1 displayed by the display device 123 may be a wavefront map that depicts the OPD over the pupil, e.g., subapertures, of the wavefront sensor 2511', or a graphical display of the coefficients of the OPD function as illustrated in FIG. 6C.

The fixation target is provided by an internal fixation target 71 (e.g., a visible image source) that cooperates with a third relay lens group $LG_3$, dielectric filter 114, and second polarizing beam splitter/quarter wave plate 109'/111' to create an image of a fixation target 71 at the phase compensator 53. The phase compensator 53, under control of controller 57, operates to spatially modulate the phase of the image of the fixation target to compensate for the aberrations of the eye under examination as measured by the wavefront sensor 55. The second polarizing beam splitter/quarter wave plate 109'/111', first polarizing beam splitter/quarter wave plate 103'/105,' and first lens group $LG_1$ recreate the phase compensated image of the fixation target 71 produced by the phase compensator 53 at the pupil of the eye 1 under examination. This operation provides the patient with a view of correction (e.g., compensation) of the aberrations of the eye 1 under examination such the patient can provide instant feedback as to the accuracy of the measurement.

Image capture is provided by an imaging illumination source 87 (e.g., halogen or xenon flash lamp) that cooperates with lens 127, beam combiner 129, first polarizing beam splitter/quarter wave plate 103'/105', and first lens group $LG_1$ to direct light produced from the imaging illumination source 87 onto the pupil of the eye 1, which is reflected and directed back to the instrument pupil. The first lens group $LG_1$, first polarizing beam splitter/quarter wave plate 103'/105', and second polarizing beam splitter/quarter wave plate 109'/111' create an image of these reflections on the phase compensator 53. The phase compensator 53, under control of controller 57, operates to spatially modulate the phase of such images to compensate for the aberrations of the eye 1 as measured by the wavefront sensor 55. The second polarizing beam splitter/quarter wave plate 109'/111', dielectric filter 114, beam splitter 117' and fourth relay lens group $LG_4$ recreate the compensated image of such reflected wavefronts as produced by the phase compensator 53 at imaging device 89 (such as a CCD camera body, 3-CCD camera body, CMOS camera body and/or a photographic film unit) for capture. This operation provides the user with the capability of acquiring high resolution images of the eye 1.

As is well known in the art, spectral filters that are tuned to the wavelength of the extended source 2513'' and/or imaging illumination source 87 may be disposed along the optical path between the beam splitter 117' and the wavefront sensor 55 and imaging device 89, respectively, in order to reduce background noise and noise from the other illumination sources of the instrument.

As shown in FIG. 27A, the wavefront sensor 2511' includes beam combiner 2711, collimating lens 2516' and a plurality of subapertures 2514' (e.g., lens array) that cooperate to form a plurality of images 2515' of the extended source 2513'', which are derived from retinal reflections of the extended source 2513''. A relay lens 2713 and imaging device 2517' (e.g., one or more CCD-based or CMOS-based image sensors) cooperate to capture the plurality of images 2515'. The imaging device 2517' outputs image data representing such images 2515'. An image processing computer 2519' generates an estimate of the gradient field of the incident wavefront (i.e., the compensated image of the distorted wavefront provided by the phase compensator 53, which is derived from retinal reflections of the extended source 2513") by applying image processing techniques to the image data representing images 2515'. More specifically, the image processing computer 2519' applies image correlation techniques in the digital domain to such image data to derive a correlation product for a given image $2515_i$ and corresponding subaperture $2514_j$. The peak correlation point of the correlation product for the given image $2515_i$/subaperture $2514_j$ provides the tilt estimate of the incident wavefront (i.e., the compensated image of the distorted wavefront provided by the phase compensator 53, which is derived from retinal reflections of the extended source 2513") over the given subaperture $2514_j$.

As described above, the correlation product for a given image $2515_i$ may be derived from reference image data. The reference image data may based upon the collection of image data for a plurality of subapertures, for example, comprising the average subaperture image (wherein each pixel in the average subaperture image represents the average intensity value for that pixel over all of the subaperture image data). Alternatively, the reference image data may be based upon image data derived from a reference source, for example, formed by projecting a perfect (or substantially non-aberrated) image of the extended source 2513' (or like source) onto the plane of the subapertures 2514' and capturing the images formed by the subapertures 2514' in response to this reference. As shown in FIG. 27B, beam splitter 2703', beam folding mirrors $2715_1$' and $2715_2$' and beam combiner 2711 provide this functionality by projecting a perfect (or substantially non-aberrated) image of the extended source 2513" onto the plane of the subapertures 2514'. In embodiments wherein such functionality is not required, these elements may be omitted.

The local tilt estimates generated by the image processing computer 2519' can be reconstructed to form data representative of the aberrations (including defocus, spherical aberration, coma, astigmatism in addition to other higher order aberrations) of the incident wavefront (i.e., the compensated image of the distorted wavefront provided by the phase compensator 53, which is derived from retinal reflections of the extended source 2513") on the subapertures 2514'. For example, the local tilt estimates may be reconstructed into an optical path difference (OPD) array, which stores a scalar value that represents the optical path difference at each subaperture. Alternatively, the local tilt estimates may be reconstructed into an OPD function, for example, by minimizing the difference between the derivatives of an analytical function (such as a set of Zernike polynomials, Seidel polynomials, Hermites polynomials, Chebychev polynomials, and Legendre polynomials) and the measured local tilt estimates.

The image processing computer 2519' is preferably operably coupled (for example via I/O interface 121) to a display device 123 that generates a graphical representation (such as a wavefront map that depicts the OPD over the pupil, e.g., subapertures, of the wavefront sensor 2511', or a graphical display of the coefficients of the OPD function as illustrated in FIG. 6C) of the aberrations of the eye 1 based upon the data representative of the aberrations (including defocus, spherical aberration, coma, astigmatism in addition to other higher order aberrations) of the incident wavefront as constructed by the image processing computer 2519'.

The dimensions of the image of the extended source 2513" formed on the retina of the human eye can be larger that a diffraction limited spot, yet must be small enough so that different parts of the image do not experience substantially different aberrations while passing through the eye 1 (which is the aberration-inducing medium in this application). In addition, as is evident from FIG. 25B, there the angular size of the image of the extended source 2513" must be limited so that the images 2515' formed by each subaperture (e.g., lenslet) do not overlap, which would lead to confusion in the image plane. In general, this may be accomplished through the use of an aperture stop (not shown) at the input image plane of the sensor 2511' that limits the angular field of view.

The phase compensator 53 of the adaptive optic subsystem of the ophthalmic instrument 50"" preferably comprises multiple stages (such as the variable focus lens (VFL) and a deformable mirror as shown in FIG. 7A) that compensate for different parts of the aberrations of the eye 1 as estimated by the wavefront sensor 2511'. For example, such aberrations can be decomposed into a defocus component (which represents the defocus of the eye 1) and one or more additional components (which represent the higher order components (e.g., spherical aberration, astigmatism and coma) of such aberrations. In this case, the first stage (i.e., the variable focus lens) is used to compensate for the defocus component of such aberrations, and the one or more additional stages (i.e., deformable mirror) are used to compensate for the remaining higher order components of such aberrations. A deformable mirror achieves such compensation by warping its optical surface to form the complex conjugate of such higher order components as measured by the wavefront sensor 2511'. Exemplary silicon micro-machined membrane deformable mirrors are described above with respect to FIGS. 8A and 8B.

Importantly, the use of the extended source as the wavefront sensing illumination source and the formation of the virtual extended source on the retina as described above spreads light over a larger region of the retina (than the prior art approach as described above that produced a spot image of the wavefront sensing illumination source on the retina), which allows for the use of greater total optical power than the prior art approach. The resulting use of greater total optical power improves the signal-to-noise ratio of the ophthalmic instrument, thereby enabling high quality wavefront measurements of the eye under a wider range of operating conditions (e.g., in noisier environments).

More specifically, if the eye is illuminated with a collimated beam to produce a point of light on the retina, the angular size of that spot will be about equal to the resolution limit of the eye. For typical vision, that limit is about 1 minute of arc or 0.3 milliradians. Conservatively, virtually all of the light in the point source will fall within a 1 milliradian spot on the retina. If, instead, an extended source is used, the light may be spread over a larger region of the retina. This allows the use of a greater total optical power while keeping the power density the same as in the point source case.

These advantages may be quantified as follows. Consider a wavefront sensor with a spatial sampling of 7 subapertures across the pupil. Assume that a 1000×1000 pixel focal plane is used. This implies that each subaperture focal plane covers about 150×150 pixels. If the focal ratio of the subapertures is chosen so that the subaperture diffraction limited spot covers 3 pixels from peak to null (a typical rule of thumb for Hartmann sensors) then the subaperture field of view is about 25 mrad. To prevent overlap of subaperture images a full aperture field stop of 20 mrad could be used. This means that the source size can be increased from 1 mrad to 20 mrad. At the same power density on the retina, the total power is increased by a factor of 400.

For the point source, all the wavefront information in a subaperture is contained in the single spot of roughly diffraction limited size. When using the extended source, image correlation can use all the information in 400 diffraction limited blur spot sized regions to estimate the wavefront tilt. This should lead to roughly a factor of 20 improvement in the tilt estimate for the same signal to noise ratio per pixel. Conversely, the light intensity could be reduced while still achieving the same measurement accuracy as the point source case.

Ophthalmic Instrument Providing Efficient Prescriptions of Corrective Optics

Figure 23:
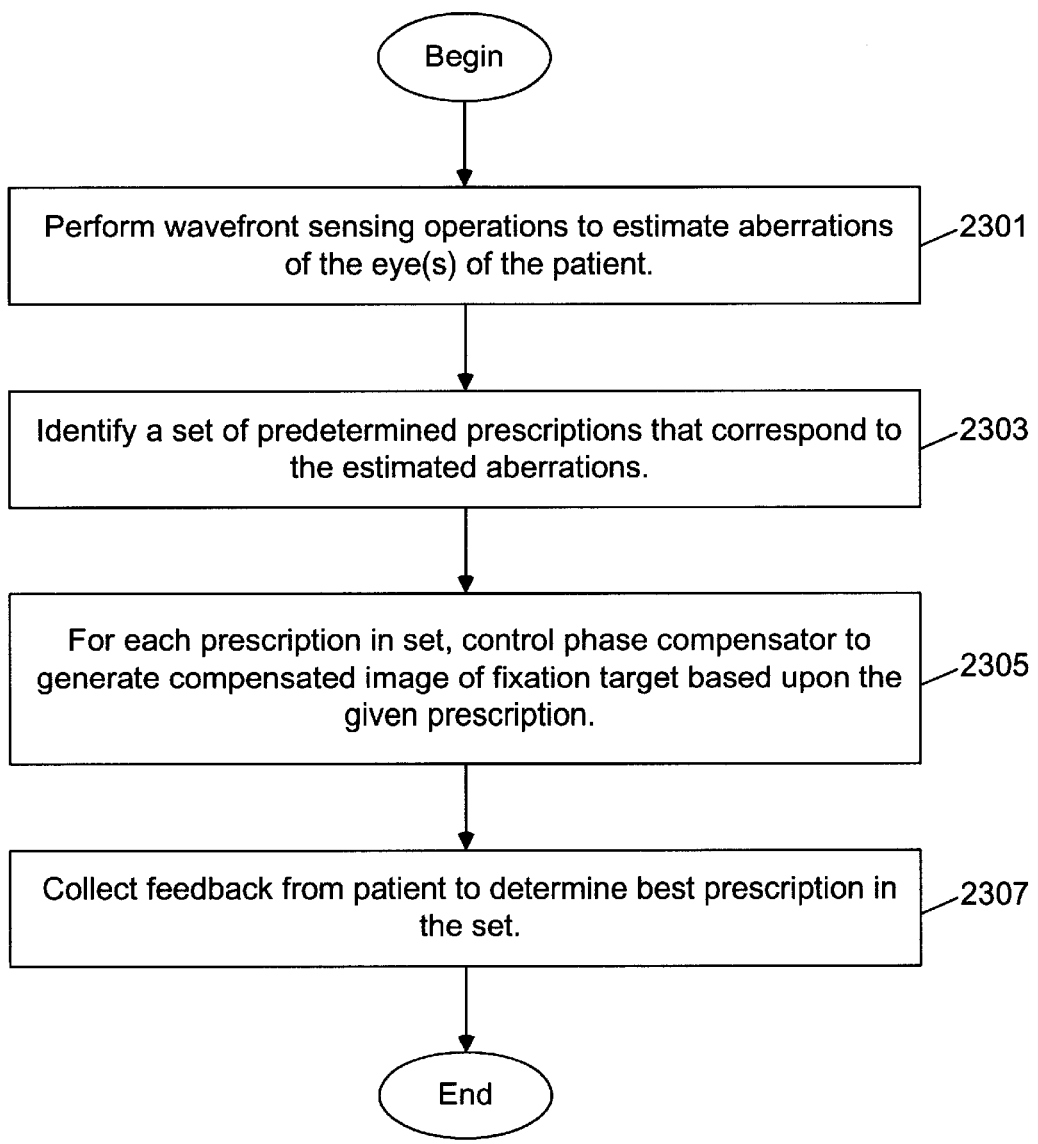
FIG. 23 is a flow chart illustrating exemplary operations of an ophthalmic instrument that provides more efficient and effective prescription of corrective optics (e.g., classes or contact lens) by measuring the aberrations (including higher order aberrations) of the eye(s) of a patient, identifying a set of prescriptions that correspond to the measured aberrations of the eye(s), and providing the patient with a view of correction (e.g., compensation) provided by the prescriptions in the set to thereby enable instant patient feedback and patient selection of the best prescription (if necessary).

In another aspect of the present invention, the capabilities of an ophthalmic instrument as described above (which provides the human eye with a view of compensation of the estimated aberrations of the eye as measured by wavefront sensing) can be exploited to enable more effective and efficient prescription of corrective optics (e.g., glasses or contact lens). FIG. 23 is a flow chart that illustrates the operations of an ophthalmic instrument that exploits such capabilities to provide more effective and efficient prescription of corrective optics.

In step 2301, the ophthalmic instrument performs wavefront sensing operations that estimate the aberrations of the eyes of the patient.

In step 2303, the ophthalmic instrument identifies a set of predetermined prescriptions (which specify the correction for corrective optics) that correspond to the such estimated aberrations. For example, each given prescription in the set can be selected from a database of prescriptions if the given prescription matches the estimated aberrations within a predetermined tolerance interval.

In step 2305, for each given prescription in set identified in step 2303, the phase compensator of the ophthalmic instrument is controlled to generate a compensated image of the fixation target based upon the given prescription, to enable the eyes to view the correction specified by the prescription.

Finally, in step 2307, feedback is collected from patient to determine the best prescription within the set.

Advantageously, the operations of an ophthalmic instrument of FIG. 23 enables instant feedback from the patient regarding the measurement and correction of the aberrations of the eye, thereby providing more effective and efficient prescription of corrective optics.

Ophthalmic System Providing Efficient Dispensing of Corrective Optics

Figure 24A:
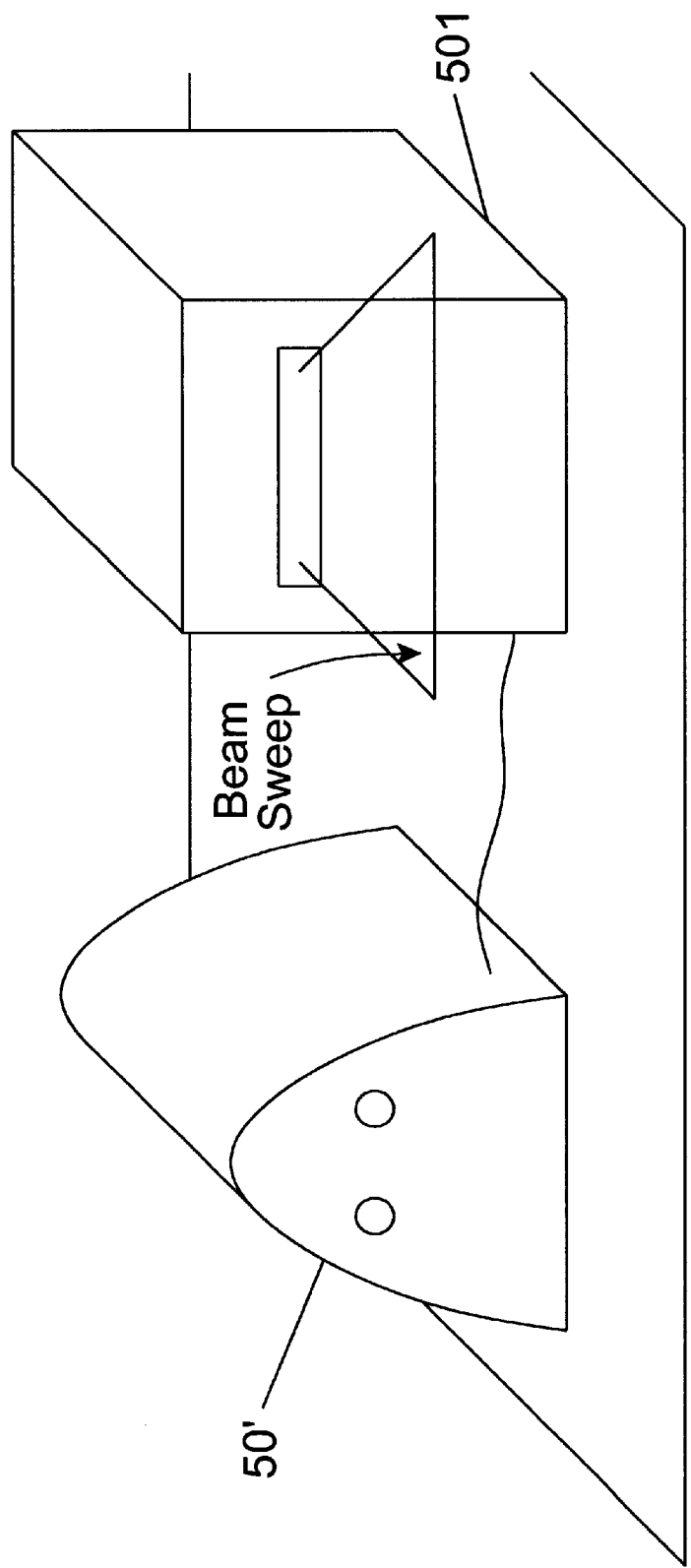
FIG. 24A is a pictorial illustration of a system that provides more efficient and effective dispensing of corrective optics (e.g., classes or contact lens) by: measuring the aberrations (including higher order aberrations) of the eye(s) of a patient, identifying a set of corrective optics that correspond to the measured aberrations of the eye(s), and providing the patient with a view of correction (e.g., compensation) provided by the corrective optics in the set to thereby enable the patient to select the optimal corrective optic (if necessary) with minimal assistance. The system preferably includes an imaging and dimension subsystem that generates a profile of the dimensions (and/or other relevant spatial characteristics) of the face and head of the patient. A set of frames that correspond to the patient's profile are identified to enable the patient to select one of the frames in the set. The patient selected corrective optics and frame (which may be custom built) are integrated into glasses and provided to the patient, thereby providing the patient with a frame that is optimally fitted to the dimension of the patient's head and face and with corrective optics that optimally compensate for the aberrations of patient's eyes.
Figure 24B:
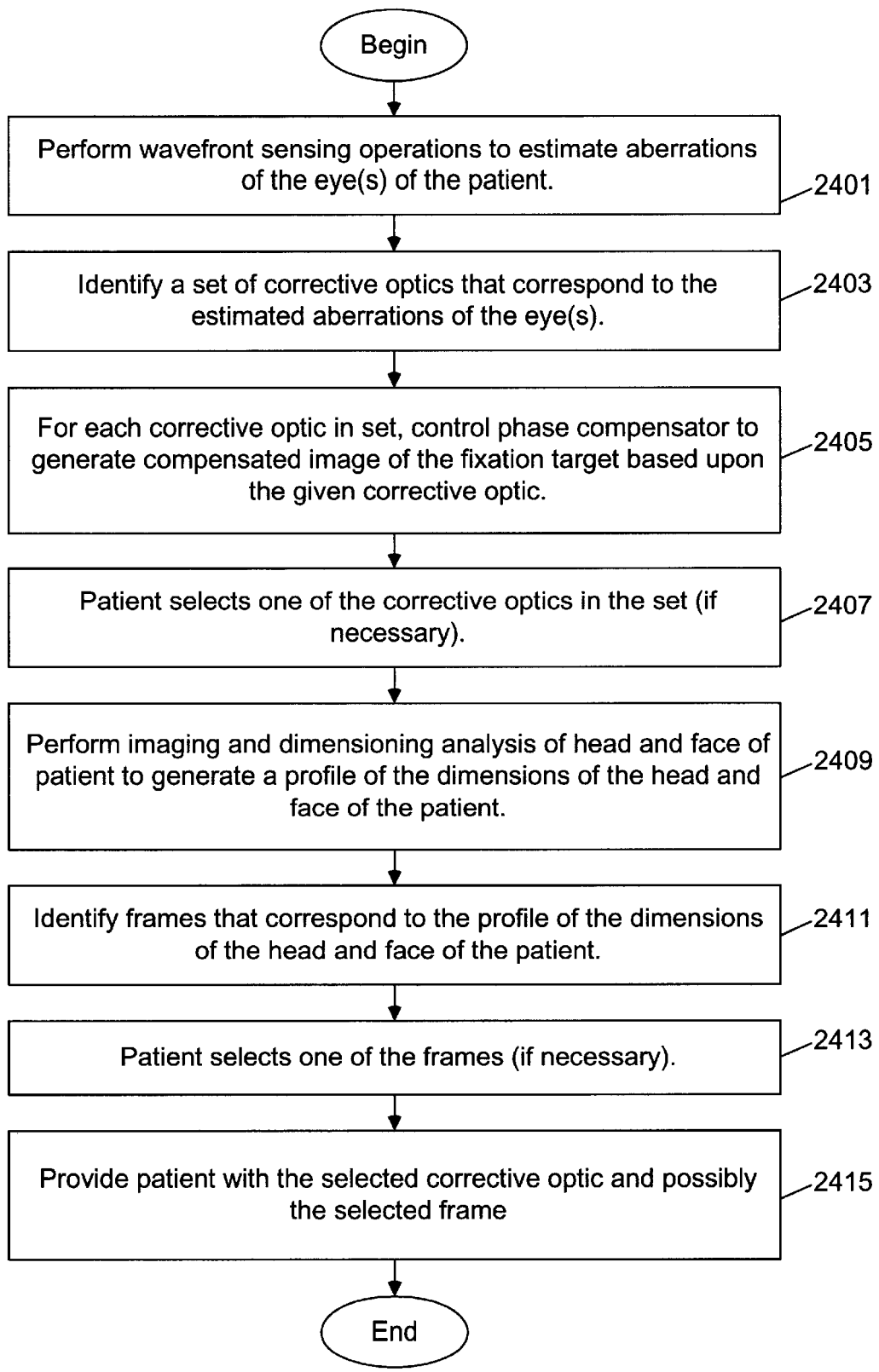
FIG. 24B is a flow chart that illustrates the operations of the system of FIG. 24A that provides the dispensing of corrective optics (e.g., glasses or contact lens) with minimal human assistance to the patient.

In another aspect of the present invention, the capabilities of an ophthalmic instrument as described above (which provides the human eye with a view of compensation of the estimated aberrations of the eye as measured by wavefront sensing) can be exploited to effectively enable dispensing of corrective optics (e.g., glasses or contact lens) without (or with minimal) additional human involvement beyond the patient's involvement. FIGS. 24A and 24B illustrates a system (and the operations performed therein) that exploits such capabilities to provide dispensing of corrective optics (e.g., glasses or contact lens) without (or with minimal) additional human involvement beyond the patient's involvement.

As shown in FIG. 24A, the system includes an ophthalmic instrument 50' which provides the human eye with a view of compensation of the estimated aberrations of the eye as measured by wavefront sensing. In the binocular configuration shown, the optical train of the adaptive optic based ophthalmic instrument is duplicated (e.g., two channels, one for each eye). Any required image processing and control may be performed by separate devices for each channel (or such processing and control may be performed on one or more shared devices for the channels). An imaging and dimension subsystem 501 that is capable of generating a profile of the dimensions (and/or other relevant spatial characteristics) of the face and head of the patient may be optionally provided. The subsystem 501 preferably sweeps a laser beam over the face and head of the patient to generate a range data map of the patient's face and head, and analyzes the range data map to derive the profile. Details and alternate embodiments of the imaging and dimension subsystem 501 may be found in co-pending U.S. patent application Ser. No. 09/327,756 filed Jun. 7, 1999 (Attorney Docket No. 108–068USA000) and International Application PCT/US00/15624, filed Jun. 7, 2000 (Attorney Docket No. 108–085PCT000), all commonly assigned to the assignee of the present invention and herein incorporated by reference in their entirety. Such a system is used to automatically fit frames to the size and shape of the patient's face and head when dispensing glasses. It is not required for the dispensing of contact lens.

FIG. 24B is a flow chart that illustrates the operations of the system of FIG. 24A that provides the dispensing of corrective optics (e.g., glasses or contact lens) with minimal human assistance to the patient. For the sake of description, it is assumed that there is an inventory of corrective optics and frames which can be made available to the patient. However, it should be readily apparent that the corrective optics and/or frames ultimately provided to the patent can be custom built according to specifications provided by the system.

In step 2401, the ophthalmic instrument 50' performs wavefront sensing operations that estimate the aberrations of the eyes of the patient.

In step 2403, the ophthalmic instrument 50' identifies a set of corrective optics in the inventory that correspond to the estimated error. For example, each given corrective optic in the set can be selected from the inventory of corrective optics if the given corrective optic matches the estimated aberrations within a predetermined tolerance interval.

In step 2405, for each corrective optic in set identified in step 2403, the phase compensator of the ophthalmic instrument 50' is controlled to generate a compensated image of the fixation target based upon the given corrective optic, to enable the eyes to view the correction provided by the given corrective optic.

In step 2407, the patient selects one of corrective optics in the set (if necessary).

In step 2409, the imaging and dimension subsystem 501 optionally performs imaging and dimensioning analysis of the head and face of the patient to generate a profile of the dimensions (or other relevant spatial characteristics) of the face and/or head of the patient.

In step 2411, one or more frames that correspond to the profile generated in step 2409 are identified (or custom built). For example, those frames that best fit the size and shape of the patient's face and/or head can be selected.

In step 2413, the patient selects one of the frames identified in step 2411 (if necessary) Finally, in step 2415, the patient is provided with corrective optic selected in step 2407. When the corrective optic are glasses, the patient is provided with glasses that includes the selected corrective optic and the selected (or custom built) frame that best fits the size and shape of the patient's face and/or head as identified in step 2411.

Preferably, the operations of FIG. 24B are performed automatically (without human involvement). Alternatively, minimal human involvement (for example, a clerk locating the selected corrective optic from the inventory) may be used to dispense the corrective optic (or glasses) selected by the patient. Advantageously, the operations of the system of FIGS. 24A and 24B enables instant feedback from the patient regarding the measurement and correction of the aberrations of the eye. Moreover, such operations lowers the costs of dispensing the corrective optics (and glasses).

Other embodiments of the invention will be apparent to those skilled in the art from consideration of the specification and practice of the invention disclosed herein. It is intended that the specification and examples be considered as examples only, with the true scope of the invention being indicated by the claims to Invention appended hereto.

What is claimed is:

1. An ophthalmic instrument for estimating aberrations in the eyes of a patient and providing said patient with a view of optical correction of said aberrations so as to provide instant feedback as to the accuracy of the estimated aberrations, said ophthalmic instrument comprising:

an adaptive optics subsystem including a wavefront sensor and a multi-stage phase compensator;

said wavefront sensor estimating aberrations in reflections of light formed as an image on the retina of an eye of said patient; and said multi-stage phase compensator, operably coupled to said wavefront sensor, and spatially modulating the phase of incident light to compensate for said aberrations estimated by said wavefront sensor, wherein said multi-stage phase compensator comprises a first stage and at least one other additional stage, wherein said first stage compensates for a defocus component of said aberrations, and wherein said at least one other additional stage compensates for other higher order components of said aberrations; and a fixation target, operably coupled to said adaptive optics subsystem, to provide the patient with a view of correction of said estimated aberrations so that the patient can provide instant feedback as to the accuracy of the estimated aberrations.

2. The ophthalmic instrument of claim 1, wherein said first stage comprises a variable focus lens.

3. The ophthalmic instrument of claim 2, wherein said variable focus lens comprises first and second lens elements aligned along an optical axis, wherein said first lens element is moved with respect to said second lens element linearly along said optical axis by a linear actuator.

4. The ophthalmic instrument of claim 1, wherein said at least one other additional stage comprises a deformable mirror.

5. The ophthalmic instrument of claim 4, wherein said deformable mirror comprises a silicon micro-machined membrane mirror including a silicon chip mounted over a printed circuit board substrate by spacers, wherein a top surface of said silicon chip comprises a membrane which is coated with a reflective layer to form a mirror surface, and wherein the printed circuit board comprises a control electrode structure that operates to deform the shape of the reflective membrane by applying bias and control voltages to the membrane and control electrodes disposed therein.

6. The ophthalmic instrument of claim 1, wherein said at least one other additional stage comprises a liquid crystal device.

7. The ophthalmic instrument of claim 1, further comprising optical elements that enable a user to examine or treat the eye.

8. The ophthalmic instrument of claim 1, further comprising a display device that displays a graphical representation of aberrations of the eye, wherein said graphical representation is based upon said aberrations estimated by said wavefront sensor.

9. An ophthalmic instrument for estimating aberrations in the eyes of a patient and providing said patient with a view of optical correction of said aberrations so as to provide instant feedback as to the accuracy of the estimated aberrations, said ophthalmic instrument comprising:

a wavefront sensor for estimating aberrations in reflections of light formed as an image on the retina of a patient's eye;

a multi-stage phase compensator, operably coupled to the wavefront sensor, for spatially modulating the phase of incident light to compensate for said aberrations estimated by said wavefront sensor, wherein said multi-stage phase compensator includes a first stage having a variable focus lens that compensates for a defocus component of the aberrations estimated by the wavefront sensor, and wherein said multi-stage phase compensator includes a second stage having a deformable mirror that compensated for other higher order components of the aberrations estimated by the wavefront sensor; and a fixation target to provide the patient with a view of correction of said estimated aberrations so that the patient can provide instant feedback as to the accuracy of the aberrations estimated by said wavefront sensor.

10. The ophthalmic instrument of claim 9, wherein said phase compensator further comprises a liquid crystal device that compensates for other higher order components of the aberrations estimated by the wavefront sensor.

11. The ophthalmic instrument of claim 9, further comprising optical elements that enable a user to examine or treat the eye.

12. The ophthalmic instrument of claim 9, further comprising a display device that displays a graphical representation of aberrations of the eye, wherein said graphical representation is based upon said aberrations estimated by said wavefront sensor.

* * * * *